(12) United States Patent
Bresson

(10) Patent No.: US 10,781,260 B2
(45) Date of Patent: Sep. 22, 2020

(54) ANTI-OX40 BINDING PROTEINS

(71) Applicant: Sorrento Therapeutics, Inc., San Diego, CA (US)

(72) Inventor: Damien Bresson, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/323,968

(22) PCT Filed: Aug. 7, 2017

(86) PCT No.: PCT/US2017/045788
§ 371 (c)(1),
(2) Date: Feb. 7, 2019

(87) PCT Pub. No.: WO2018/031490
PCT Pub. Date: Feb. 15, 2018

(65) Prior Publication Data
US 2019/0177422 A1    Jun. 13, 2019

Related U.S. Application Data

(60) Provisional application No. 62/371,993, filed on Aug. 8, 2016.

(51) Int. Cl.
| | | |
|---|---|---|
| *C07K 16/00* | (2006.01) | |
| *C07K 16/46* | (2006.01) | |
| *C07K 16/28* | (2006.01) | |
| *A61P 31/12* | (2006.01) | |
| *A61P 35/02* | (2006.01) | |
| *A61P 29/00* | (2006.01) | |

(52) U.S. Cl.
CPC .......... *C07K 16/2878* (2013.01); *A61P 29/00* (2018.01); *A61P 31/12* (2018.01); *A61P 35/02* (2018.01); *C07K 2317/51* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | |
|---|---|---|
| 2005/0049402 A1 | 3/2005 | Babcook et al. |
| 2008/0233133 A1 | 9/2008 | Watkins et al. |
| 2010/0254982 A1 | 10/2010 | Glover et al. |
| 2014/0004121 A1 | 1/2014 | Fanslow, III et al. |
| 2016/0200799 A1 | 7/2016 | Kurosawa et al. |

FOREIGN PATENT DOCUMENTS

WO    2015153513 A1    10/2015

OTHER PUBLICATIONS

International Search Report and the Written Opinion of corresponding International Application No. PCT/US20171045788; completed on Dec. 10, 2017; dated Jan. 29, 2018.

*Primary Examiner* — Maher M Haddad
(74) *Attorney, Agent, or Firm* — Baker Botts L.L.P.

(57) ABSTRACT

The present disclosure provides anti-OX40 antibodies, and antigen-binding portions thereof. In certain embodiments, the antibodies or fragments thereof, are used for the treatment of cancer.

8 Claims, 7 Drawing Sheets
Specification includes a Sequence Listing.

SEQUENCE LISTING

<160> NUMBER OF SEQ ID NOS: 219

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Tyr Gly Met Asp Val Trp Gly Gln Gly Thr
            100                 105                 110

```
Thr Val Thr Val Ser Ser
        115
```

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Asp Val Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu His Trp Tyr Gln Gln Arg Pro Gly Lys Ala Pro Asn Leu Leu Ile
        35                  40                  45

Tyr Ala Ala Ser Ser Leu His Ser Gly Val Pro Ser Arg Phe Ser Gly
50                  55                  60

Ser Gly Ser Gly Thr Asp Phe Thr Leu Thr Ile Asp Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105
```

<210> SEQ ID NO 3
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp Pro Tyr Ser Ser Ser Trp Tyr Gly Ala Glu Tyr Phe Gln
            100                 105                 110

His Trp Gly Gln Gly Thr Leu Val Thr Val Ser Ser
        115                 120
```

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Leu Val Phe Gly Gly Gly Thr Lys Leu Thr Val Leu
            100                 105                 110

<210> SEQ ID NO 5
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Asp Ser Ser Gly Tyr Ser Asp Tyr Gly Met Asp
            100                 105                 110

Val Trp Gly Gln Gly Thr Thr Val Thr Val Ser Ser
        115                 120

<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Asn Tyr Asn Thr Arg Gln
                85                  90                  95

Val Thr Phe Gly Gln Gly Thr Arg Leu Glu Ile Lys
                100                 105

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
                20                  25                  30

Tyr Leu His Trp Val Arg Gln Ala Pro Gly Gln Gly Leu Glu Trp Met
            35                  40                  45

Gly Ile Ile Asn Pro Ser Asp Gly Gly Thr Arg Tyr Ala Gln Lys Phe
        50                  55                  60

Gln Asp Arg Val Thr Met Thr Arg Asp Met Ser Thr Ser Thr Val Tyr
65                  70                  75                  80

Met Glu Leu Ser Ser Leu Arg Pro Glu Asp Thr Ala Val Tyr Tyr Cys
                85                  90                  95

Ala Arg Asp Leu Glu Tyr Ile Gly Ser Gly Ser Leu Ser Trp Phe Asp
                100                 105                 110

Pro Trp Gly Gln Gly Thr Leu Val Thr Val Ser Ser
            115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Val Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Leu
                85                  90                  95

Thr Phe Gly Gly Gly Thr Lys Val Glu Ile Lys
                100                 105
```

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Tyr Leu His Trp Val Arg Gln Ala Pro Gly Gln Gly Leu Glu Trp Met
        35                  40                  45

Gly Ile Ile Asn Pro Gly Asp Gly Ser Thr Arg Asn Ala Gln Lys Phe
    50                  55                  60

Glu Gly Arg Val Thr Met Thr Arg Asp Thr Ser Thr Ser Thr Val Tyr
65                  70                  75                  80

Met Glu Leu Ser Ser Leu Ser Pro Glu Asp Thr Ala Val Tyr Tyr Cys
                85                  90                  95

Ala Arg Asp Leu Glu Tyr Ile Gly Ser Gly Ser Leu Ser Trp Phe Asp
            100                 105                 110

Pro Trp Gly Gln Gly Thr Leu Val Thr Val Ser Ser
        115                 120

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Pro Val Leu Thr Gln Pro Ala Ser Val Ser Gly Ser Pro Gly Gln
1               5                   10                  15

Ser Ile Thr Ile Ser Cys Ser Gly Thr Ser Ser Asp Phe Leu Thr Tyr
            20                  25                  30

Asp Leu Val Ser Trp Tyr Lys Gln Gln Pro Gly Lys Ala Pro Lys Leu
        35                  40                  45

Met Ile Tyr Asp Val Asn Lys Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Ala Asp Glu Ala Asp Tyr Tyr Cys Ser Ser Tyr Thr Ser Ser
                85                  90                  95

Ser Thr Pro Tyr Val Phe Gly Thr Gly Thr Lys Val Thr Val Leu
            100                 105                 110

<210> SEQ ID NO 11
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ala

-continued

```
                1               5                  10                     15
Ser Val Lys Val Ser Cys Lys Ala Ser Gly Tyr Thr Phe Thr Ser Tyr
                    20                  25                     30

Tyr Met His Trp Val Arg Gln Ala Pro Gly Gln Gly Leu Glu Trp Met
            35                  40                  45

Gly Ile Ile Asn Pro Ser Gly Ser Thr Ser Tyr Ala Gln Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Pro Tyr Ser Ser Trp Tyr Gly Ala Glu Tyr Phe Gln
                100                 105                 110

His Trp Gly Gln Gly Thr Leu Val Thr Val Ser Ser
                115                 120
```

<210> SEQ ID NO 12
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Ser Val Leu Thr Gln Pro Arg Ser Val Ser Gly Ser Pro Gly Gln
1               5                  10                     15

Ser Val Thr Ile Ser Cys Thr Gly Thr Ser Ser Asp Gly Gly Asp Tyr
                20                  25                  30

Asn Tyr Val Ser Trp Tyr Gln Gln His Pro Gly Gln Ala Pro Lys Leu
            35                  40                  45

Leu Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
                100                 105                 110
```

<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Val Gln Ser Gly Ala Glu Val Lys Lys Pro Gly Ala
1               5                  10                     15

Ser Val Lys Val Ser Cys Lys Ala Ser Gly Tyr Thr Phe Thr Ser Tyr
                20                  25                  30

Gly Ile Ser Trp Val Arg Gln Ala Leu Gly Gln Arg Leu Glu Trp Leu
            35                  40                  45

Gly Trp Ile Asn Ala Gly Asp Gly Glu Thr Lys Tyr Ser Pro Lys Phe
        50                  55                  60

Gln Gly Arg Val Thr Ile Thr Arg Asp Thr Ser Ala Ser Thr Ala Tyr
```

```
              65                  70                  75                  80
Met Asp Leu Ser Gly Leu Thr Ser Glu Asp Thr Ala Val Tyr Tyr Cys
                85                  90                  95

Ala Arg Asp Phe Leu Ser Thr Met Asp Tyr Trp Gly Gln Gly Thr Leu
            100                 105                 110

Val Thr Val Ser Ser
            115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Gly Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asp Asn Leu Pro Tyr
                85                  90                  95

Thr Phe Gly Gln Gly Thr Lys Val Glu Ile Lys
            100                 105

<210> SEQ ID NO 15
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Tyr Leu His Trp Val Arg Gln Ala Pro Gly Gln Gly Leu Gln Trp Met
        35                  40                  45

Gly Trp Ile Asn Pro Thr Ser Gly Asp Thr Asn Tyr Ala Pro Glu Tyr
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly His Asp Tyr Ser Arg Thr Pro Val Gly Ala Glu Ala Leu
            100                 105                 110

Asp Tyr Trp Gly Gln Gly Thr Leu Val Thr Val Ser Ser
        115                 120                 125
```

<210> SEQ ID NO 16
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Pro Val Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Leu Ile Tyr Glu Val Ser Lys Arg Pro Ser Gly Val Pro Ala Arg Phe
    50                  55                  60

Ala Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn His Val Phe Gly Thr Gly Thr Lys Leu Thr Val Leu
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Ser Val Leu Thr Gln Pro Ala Ser Val Ser Gly Ser Pro Gly Gln
1               5                   10                  15

Ser Ile Thr Ile Pro Cys Thr Gly Thr Ser Asn Asp Ile Gly Thr Tyr
            20                  25                  30

Asn Leu Ala Ser Trp Tyr Gln His His Ala Gly Lys Ala Pro Lys Leu
        35                  40                  45

Ile Ile Tyr Asp Leu Asn His Arg Pro Ser Gly Val Ser Asn Arg Phe
    50                  55                  60

Ser Gly Tyr Lys Ser Asp Asn Thr Ala Phe Leu Thr Ile Ser Gly Leu
65                  70                  75                  80

Gln Pro Glu Asp Glu Ser Asn Tyr Tyr Cys Ser Ser Tyr Thr Met Asn
                85                  90                  95

Thr Thr Pro Ile Leu Phe Gly Gly Gly Thr Lys Leu Thr Val Leu
            100                 105                 110

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

```
Phe Val Tyr Trp Tyr Gln Gln Leu Pro Gly Met Ala Pro Lys Leu Leu
            35                  40                  45

Ile Tyr Lys Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr His Cys Ala Ala Trp Asp Asp Ser Leu
                 85                  90                  95

Ser Gly His Val Val Phe Gly Gly Thr Lys Leu Thr Val Leu
             100                 105                 110

<210> SEQ ID NO 19
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
             20                  25                  30

Tyr Leu His Trp Val Arg Gln Ala Pro Gly Gln Gly Leu Glu Trp Met
            35                  40                  45

Gly Ile Ile Asn Pro Ser Asp Gly Ser Thr Arg Asn Ala Gln Lys Phe
 50                  55                  60

Glu Gly Arg Val Thr Met Thr Arg Asp Thr Ser Thr Ser Thr Val Tyr
65                  70                  75                  80

Met Glu Leu Ser Ser Leu Ser Pro Glu Asp Thr Ala Val Tyr Tyr Cys
                 85                  90                  95

Ala Arg Asp Leu Glu Tyr Ile Gly Ser Gly Ser Leu Ser Trp Phe Asp
             100                 105                 110

Pro Trp Gly Gln Gly Thr Leu Val Thr Val Ser Ser
            115                 120

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ser Val Leu Thr Gln Pro Ala Ser Val Ser Gly Ser Pro Gly Gln
1               5                   10                  15

Ser Val Thr Val Ser Cys Thr Gly Thr Ser Ser Asp Ile Gly Ala Tyr
             20                  25                  30

Glu Ser Val Ser Trp Tyr Gln Gln His Pro Gly Lys Gly Pro Lys Leu
            35                  40                  45

Ile Ile Tyr Asp Val Ser Arg Pro Ser Gly Val Ser Ile Arg Phe
 50                  55                  60

Ser Gly Ser Lys Ser Gly Asn Ser Ala Ser Leu Thr Ile Ser Gly Leu
65                  70                  75                  80

Gln Ala Glu Asp Glu Ala Glu Tyr Phe Cys Ser Ser Phe Thr Arg Gly
                 85                  90                  95
```

```
Ser Thr Pro Tyr Val Phe Gly Thr Gly Thr Lys Val Thr Val Leu
            100                 105                 110

<210> SEQ ID NO 21
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
                20                  25                  30

Tyr Met His Trp Val Arg Gln Ala Pro Gly Gln Gly Leu Glu Trp Met
            35                  40                  45

Gly Leu Leu Asn Pro Ser Gly Gly Tyr Thr Thr Tyr Ala Gln Arg Phe
    50                  55                  60

Gln Gly Arg Val Thr Met Thr Trp Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Lys Asp Pro Tyr Ser Ser Ser Trp Tyr Gly Ala Glu Tyr Phe Gln
            100                 105                 110

His Trp Gly Gln Gly Thr Leu Val Thr Val Ser Ser
        115                 120

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
                20                  25                  30

Asn Tyr Val Ser Trp Tyr Gln Gln His Pro Gly Arg Ala Pro Lys Leu
            35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ser Leu Tyr Val Phe Gly Thr Gly Thr Lys Val Thr Val Leu
            100                 105                 110

<210> SEQ ID NO 23
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 23

Gln Ser Val Leu Thr Gln Pro Ala Ser Val Ser Gly Ser Pro Gly Gln
1               5                   10                  15

Ser Ile Thr Ile Ser Cys Thr Gly Ser Ser Asp Ile Gly Gly Tyr
            20                  25                  30

Asn Ser Val Ser Trp Tyr Gln Gln Tyr Pro Gly Lys Ala Pro Lys Leu
        35                  40                  45

Met Ile His Asp Val Asn Glu Arg Pro Ser Gly Ile Ser Asp Arg Phe
    50                  55                  60

Ser Gly Ser Lys Ser Gly Asn Thr Ala Ser Leu Thr Ile Ser Gly Leu
65              70                  75                  80

Gln Gly Glu Asp Glu Ala Glu Tyr Tyr Cys Ala Ser Tyr Ser Val Phe
                85                  90                  95

Ser Pro Phe Leu Phe Gly Arg Gly Thr Lys Leu Thr Val Leu
            100                 105                 110

<210> SEQ ID NO 24
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Met Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Tyr Leu His Trp Val Arg Gln Ala Pro Gly Gln Gly Leu Glu Trp Met
        35                  40                  45

Gly Ile Ile Asn Pro Ser Asp Gly Ser Thr Arg Asn Ala Gln Lys Phe
    50                  55                  60

Glu Gly Arg Val Thr Met Thr Arg Asp Thr Ser Thr Ser Thr Val Tyr
65              70                  75                  80

Met Glu Leu Ser Ser Leu Ser Pro Glu Asp Thr Ala Val Tyr Tyr Cys
                85                  90                  95

Ala Arg Asp Leu Glu Tyr Ile Gly Ser Gly Ser Leu Ser Trp Phe Asp
            100                 105                 110

Pro Trp Gly Gln Gly Thr Leu Val Thr Val Ser Ser
        115                 120

<210> SEQ ID NO 25
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Ala Tyr
            20                  25                  30

Asp Tyr Val Ser Trp Tyr Gln Gln Gln Pro Gly Gln Ala Pro Lys Leu
        35                  40                  45

```
Ile Ile Tyr Asp Val Asn Asn Arg Pro Ser Gly Val Ser Asn Arg Phe
        50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                     85                  90                  95

Ser Thr Leu Val Tyr Val Phe Gly Thr Gly Thr Lys Val Thr Val Leu
                100                 105                 110
```

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Leu Pro Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Tyr Tyr
                20                  25                  30

Asp Ser Val Ser Trp Tyr Gln Gln Tyr Pro Gly Lys Ala Pro Lys Leu
                 35                  40                  45

Leu Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
 65                  70                  75                  80

Gln Ala Asp Asp Glu Ala Glu Tyr His Cys Ser Ser Tyr Ser Asp Ser
                     85                  90                  95

Ser Pro Phe Val Phe Gly Thr Gly Thr Lys Val Thr Val Leu
                100                 105                 110
```

<210> SEQ ID NO 27
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Leu Pro Val Leu Thr Gln Pro Ala Ser Val Ser Gly Ser Pro Gly Gln
 1               5                  10                  15

Ser Ile Thr Ile Ser Cys Thr Gly Thr Ala Ser Ser Asp Val Gly Gly Tyr
                20                  25                  30

Asn Ser Val Ser Trp Tyr Gln Gln His Pro Gly Lys Ala Pro Lys Leu
                 35                  40                  45

Met Ile Tyr Asp Val Ser Asn Arg Pro Ser Gly Ile Ser Asn Arg Phe
        50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                     85                  90                  95

Asn Ile Val Tyr Val Phe Gly Thr Gly Thr Lys Val Thr Val Leu
                100                 105                 110
```

<210> SEQ ID NO 28
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Pro Val Leu Thr Gln Pro Ala Ser Val Ser Gly Ser Pro Gly Gln
1               5                   10                  15

Ser Ile Thr Ile Ser Cys Thr Gly Thr Thr Ser Asp Ile Gly Gly Tyr
            20                  25                  30

Asn Ser Val Ser Trp Tyr Gln Gln His Pro Gly Arg Ala Pro Lys Leu
        35                  40                  45

Ile Ile Tyr Asp Val Thr Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Asn Ser Val Tyr Val Phe Gly Thr Gly Thr Lys Leu Thr Val Leu
            100                 105                 110

<210> SEQ ID NO 29
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Phe Ser Ser Trp Tyr Ala Tyr Gly Met Asp Val Trp Gly
            100                 105                 110

Gln Gly Thr Thr Val Thr Val Ser Ser
        115                 120

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
```

Leu Ala Trp Tyr Gln Gln Lys Pro Gly Glu Pro Pro Asn Leu Leu Ile
            35                  40                  45

Tyr Asp Ala Ser Thr Leu Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Phe Arg Thr Tyr Pro Leu
                85                  90                  95

Thr Phe Gly Gly Gly Thr Lys Leu Glu Ile Lys
            100                 105

<210> SEQ ID NO 31
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Leu Trp Phe Ser Glu Phe Asp Tyr Trp Gly Gln Gly
            100                 105                 110

Thr Leu Val Thr Val Ser Ser
        115

<210> SEQ ID NO 32
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Pro Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Gly Ser Thr Ser Gly Thr Ser Ala Thr Leu Gly Ile Ala Gly Leu Gln
65                  70                  75                  80

Thr Gly Asp Glu Ala Asp Tyr Tyr Cys Gly Thr Trp Asp Ser Ser Leu

```
                    85                  90                  95

Gly Trp Val Phe Gly Gly Gly Thr Lys Leu Thr Val Leu
                100                 105

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ser Val Leu Thr Gln Pro Arg Ser Val Ser Gly Ser Pro Gly Gln
1               5                   10                  15

Ser Val Thr Ile Ser Cys Thr Gly Thr Ser Ser Asp Gly Gly Asp Tyr
                20                  25                  30

Asn Tyr Val Ser Trp Tyr Gln Gln His Pro Gly Gln Ala Pro Lys Leu
            35                  40                  45

Leu Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
                100                 105                 110

<210> SEQ ID NO 34
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Phe Ser Ser Trp Tyr Ala Tyr Gly Met Asp Val Trp Gly
                100                 105                 110

Gln Gly Thr Thr Val Thr Val Ser Ser
        115                 120

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 35

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Ala Trp Tyr Gln Gln Lys Pro Gly Glu Pro Pro Asn Leu Leu Ile
        35                  40                  45

Tyr Asp Ala Ser Thr Leu Glu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Phe Arg Thr Tyr Pro Leu
                85                  90                  95

Thr Phe Gly Gly Gly Thr Lys Leu Glu Ile Lys
            100                 105

<210> SEQ ID NO 36
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Ser Val Ser Trp Tyr Gln Gln Arg Pro Gly Lys Ala Pro Lys Leu
        35                  40                  45

Met Ile Tyr Asp Val Ile Gln Arg Pro Ser Glu Val Ser His Arg Phe
    50                  55                  60

Ser Gly Ser Lys Ser Gly Asn Thr Ala Ser Leu Thr Ile Ser Gly Leu
65                  70                  75                  80

Leu Pro Glu Asp Glu Ala Glu Tyr Phe Cys Gly Ser Tyr Ala Ala Ser
                85                  90                  95

Thr Thr Phe Val Phe Gly Gly Gly Thr Lys Leu Thr Val Leu
            100                 105                 110

<210> SEQ ID NO 37
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Tyr Ser Ser Ser Trp Tyr Gly Ala Glu Tyr Phe Gln
                100                 105                 110

His Trp Gly Gln Gly Thr Leu Val Thr Val Ser Ser
            115                 120

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ser Val Leu Thr Gln Pro Arg Ser Val Ser Gly Ser Pro Gly Gln
1               5                   10                  15

Ser Val Thr Ile Ser Cys Thr Gly Thr Ser Ser Asp Gly Gly Asp Tyr
                20                  25                  30

Asn Tyr Val Ser Trp Tyr Gln Gln His Pro Gly Gln Ala Pro Lys Leu
            35                  40                  45

Leu Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
                100                 105                 110

<210> SEQ ID NO 39
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
                20                  25                  30

Phe Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Leu Thr Met Thr Arg Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Tyr Ser Ser Ser Trp Tyr Gly Ala Glu Tyr Phe Gln
                100                 105                 110

His Trp Gly Gln Gly Thr Leu Val Thr Val Ser Ser
            115                 120

<210> SEQ ID NO 40
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Pro Val Leu Thr Gln Pro Pro Ser Ala Ser Gly Thr Pro Gly Gln
1               5                   10                  15

Arg Val Ser Ile Ser Cys Ser Gly Ser Ser Asn Ile Gly Thr Asn
            20                  25                  30

Thr Val Asn Trp Tyr Gln Gln Leu Pro Gly Thr Ala Pro Lys Leu Leu
        35                  40                  45

Val Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ser Ala Trp Asp Asp Ser Leu
                85                  90                  95

Asn Gly Gln Val Phe Gly Ala Gly Thr Lys Val Thr Val Leu
            100                 105                 110

<210> SEQ ID NO 41
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Tyr Tyr
            20                  25                  30

Asp Ser Val Ser Trp Tyr Gln Gln Tyr Pro Gly Lys Ala Pro Lys Leu
        35                  40                  45

Leu Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Glu Tyr His Cys Ser Ser Tyr Ser Asp Ser
                85                  90                  95

Ser Pro Phe Val Phe Gly Thr Gly Thr Lys Val Thr Val Leu
            100                 105                 110

<210> SEQ ID NO 42
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Ser Phe Ser Gly Tyr
            20                  25                  30

Asp Met Ser Trp Val Arg Gln Ala Pro Gly Lys Gly Leu Glu Trp Val
            35                  40                  45

Ser Ser Ile Ser Thr Ser Gly Gly Ser Thr Asn Tyr Ala Asp Ser Val
50                  55                  60

Asn Gly Arg Phe Ile Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Glu Gly Ser Gly Trp Tyr Asp Ala Gly Tyr Phe Asp Tyr Trp
            100                 105                 110

Gly Gln Gly Thr Leu Val Thr Val Ser Ser
            115                 120

<210> SEQ ID NO 43
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Ser
            20                  25                  30

Leu Asn Trp Tyr Gln Gln Lys Pro Gly Lys Ala Pro Asn Leu Leu Ile
            35                  40                  45

Tyr Asp Ala Ser Thr Leu Gln Arg Gly Val Pro Ser Arg Phe Ser Gly
50                  55                  60

Ser Gly Ser Gly Thr Lys Phe Thr Phe Thr Ile Ser Ser Leu Gln Pro
65                  70                  75                  80

Glu Asp Ile Ala Thr Tyr Tyr Cys Gln Gln Tyr Ala Asn Leu Pro Pro
                85                  90                  95

Ile Thr Phe Gly Gln Gly Thr Arg Leu Glu Ile Lys
            100                 105

<210> SEQ ID NO 44
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Tyr Leu His Trp Val Arg Gln Ala Pro Gly Gln Gly Leu Glu Trp Met
            35                  40                  45

Gly Ile Ile Asn Pro Ser Asp Gly Gly Thr Arg Tyr Ala Gln Lys Phe
50                  55                  60

Gln Asp Arg Val Thr Met Thr Arg Asp Met Ser Thr Ser Thr Val Tyr
65                  70                  75                  80

```
Met Glu Leu Ser Ser Leu Arg Pro Glu Asp Thr Ala Val Tyr Tyr Cys
                85                  90                  95

Ala Arg Asp Leu Glu Tyr Ile Gly Ser Gly Ser Leu Ser Trp Phe Asp
            100                 105                 110

Pro Trp Gly Gln Gly Thr Leu Val Thr Val Ser Ser
        115                 120
```

<210> SEQ ID NO 45
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Leu Pro Val Leu Thr Gln Pro Ala Ser Val Ser Gly Ser Pro Gly Gln
1               5                   10                  15

Ser Ile Thr Ile Ser Cys Thr Gly Thr Thr Ser Asp Ile Gly Gly Tyr
            20                  25                  30

Asn Ser Val Ser Trp Tyr Gln Gln His Pro Gly Arg Ala Pro Lys Leu
        35                  40                  45

Ile Ile Tyr Asp Val Thr Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Asn Ser Val Tyr Val Phe Gly Thr Gly Thr Lys Leu Thr Val Leu
            100                 105                 110
```

<210> SEQ ID NO 46
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Glu Val Gln Leu Val Gln Ser Gly Gly Gly Leu Val Gln Pro Gly Gln
1               5                   10                  15

Ser Leu Arg Leu Ser Cys Thr Pro Tyr Gly Phe Ser Phe Asn Asp Tyr
            20                  25                  30

Gly Met Ser Trp Val Arg Gln Ala Pro Gly Lys Gly Leu Glu Trp Leu
        35                  40                  45

Ala Phe Val Gly Ser Lys Ala Ser Gly Gly Ala Ser Glu Asn Val Ala
    50                  55                  60

Ala Val Gln Gly Arg Phe Ser Phe Ser Arg Asp Asp Ala Lys Gly Ile
65                  70                  75                  80

Ala Tyr Leu Gln Leu Asn Asn Leu Lys Pro Glu Asp Thr Gly Val Tyr
                85                  90                  95

Phe Cys Thr Arg Asp Leu Gly Thr Ser Gly Pro Tyr Phe Phe Asp Tyr
            100                 105                 110

Trp Gly Gln Gly Thr Leu Val Thr Val Ser Ser
        115                 120
```

<210> SEQ ID NO 47
<211> LENGTH: 106

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Leu Pro Val Leu Thr Gln Ser Pro Ser Val Ser Pro Gly Gln
1               5                   10                  15

Thr Gly Tyr Met Asn Cys Tyr Gly His Glu Leu Thr Asp Lys Tyr Val
                20                  25                  30

Ser Trp Tyr Gln Lys Lys Pro Gly Gln Ser Pro Val Leu Val Ile Tyr
            35                  40                  45

Glu Asp Thr Lys Arg Pro Ser Gly Ile Pro Asp Arg Phe Ser Gly Ser
50                  55                  60

Asn Ser Gly Asp Thr Ala Thr Leu Thr Ile Ser Gly Thr Gln Ala Leu
65                  70                  75                  80

Asp Glu Ala Asp Tyr Tyr Cys Gln Ala Trp Asp Ser Asn Thr Val Ile
                85                  90                  95

Phe Gly Gly Gly Thr Lys Leu Thr Val Leu
            100                 105

<210> SEQ ID NO 48
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Pro Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Glu Arg Pro Ser Gly Ile Pro Asp Arg Phe Ser
50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Tyr Thr Asp Arg Asp
                85                  90                  95

Thr Pro Tyr Val Phe Gly Gly Gly Thr Lys Val Thr Val Leu
            100                 105                 110

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Tyr Trp Met Ser
1               5

<210> SEQ ID NO 50
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 50

Asn Ile Lys Gln Asp Gly Ser Glu Lys Tyr Tyr Val Asp Ser Val Lys
1               5                   10                  15
Gly

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asp Tyr Tyr Tyr Gly Met Asp Val
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ala Ser Gln Gly Ile Arg Asn Asp Leu His
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ala Ser Ser Leu His Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Gln Ala Asn Ser Phe Pro Ile Thr
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55
```

```
Ser Tyr Tyr Met His
1               5

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Ile Asn Pro Ser Gly Gly Ser Thr Ser Tyr Ala Gln Lys Phe Gln
1               5                   10                  15

Gly

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Pro Tyr Ser Ser Ser Trp Tyr Gly Ala Glu Tyr Phe Gln His
1               5                   10                  15

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Gly Ser Ser Ser Asn Ile Gly Ser Asn Tyr Val Tyr
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Asn Asn Gln Arg Pro Ser
1               5

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Ala Trp Asp Asp Ser Leu Ser Gly Leu Val
1               5                   10

<210> SEQ ID NO 61
<211> LENGTH: 5
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 61

Ser Tyr Tyr Met His
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Ile Asn Pro Ser Gly Gly Ser Thr Ser Tyr Ala Gln Lys Phe Gln
1               5                   10                  15

Gly

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Tyr Tyr Asp Ser Ser Gly Tyr Ser Asp Tyr Gly Met Asp Val
1               5                   10                  15

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ala Ser Gln Ser Ile Ser Ser Tyr Leu Asn
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Ser Ser Leu Gln Ser
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Gln Gln Asn Tyr Asn Thr Arg Gln Val Thr
1               5                   10

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Tyr Tyr Leu His
1               5

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Ile Asn Pro Ser Asp Gly Gly Thr Arg Tyr Ala Gln Lys Phe Gln
1               5                   10                  15
Asp

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Leu Glu Tyr Ile Gly Ser Gly Ser Leu Ser Trp Phe Asp Pro
1               5                   10                  15

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Ala Ser Gln Gly Ile Ser Ser Ala Leu Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Ala Ser Ser Leu Glu Ser
1               5

<210> SEQ ID NO 72
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 72

Gln Gln Phe Asn Asn Tyr Pro Leu Thr
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Tyr Tyr Leu His
1               5

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Ile Asn Pro Gly Asp Gly Ser Thr Arg Asn Ala Gln Lys Phe Glu
1               5                   10                  15

Gly

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Leu Glu Tyr Ile Gly Ser Gly Ser Leu Ser Trp Phe Asp Pro
1               5                   10                  15

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Gly Thr Ser Ser Asp Phe Leu Thr Tyr Asp Leu Val Ser
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

Asp Val Asn Lys Arg Pro Ser
1               5

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Ser Tyr Thr Ser Ser Ser Thr Pro Tyr Val
1               5                   10

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Tyr Tyr Met His
1               5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Ile Asn Pro Ser Gly Gly Ser Thr Ser Tyr Ala Gln Lys Phe Gln
1               5                   10                  15

Gly

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Pro Tyr Ser Ser Ser Trp Tyr Gly Ala Glu Tyr Phe Gln His
1               5                   10                  15

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Gly Thr Ser Ser Asp Gly Gly Asp Tyr Asn Tyr Val Ser
1               5                   10

<210> SEQ ID NO 83
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 83

Glu Val Ser Asn Arg Pro Ser
1               5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Ser Tyr Thr Ser Ser Ser Thr Leu Val Val
1               5                   10

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Tyr Gly Ile Ser
1               5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Trp Ile Asn Ala Gly Asp Gly Glu Thr Lys Tyr Ser Pro Lys Phe Gln
1               5                   10                  15

Gly

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Phe Leu Ser Thr Met Asp Tyr
1               5

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88
```

```
Gln Ala Ser Gln Asp Ile Ser Asn Tyr Leu Asn
1               5                   10
```

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Asp Ala Ser Asn Leu Glu Thr
1               5
```

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Gln Gln Phe Asp Asn Leu Pro Tyr Thr
1               5
```

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Gly Tyr Tyr Leu His
1               5
```

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Trp Ile Asn Pro Thr Ser Gly Asp Thr Asn Tyr Ala Pro Glu Tyr Gln
1               5                   10                  15

Gly
```

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Gly His Asp Tyr Ser Arg Thr Pro Val Gly Ala Glu Ala Leu Asp Tyr
1               5                   10                  15
```

<210> SEQ ID NO 94
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 94

Thr Gly Thr Ser Ser Asp Ile Gly Gly Tyr Asn Tyr Val Ser
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Val Ser Lys Arg Pro Ser
1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Ser Tyr Ala Gly Asn Asn Asn His Val
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Gly Thr Ser Asn Asp Ile Gly Thr Tyr Asn Leu Ala Ser
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asp Leu Asn His Arg Pro Ser
1               5

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Ser Tyr Thr Met Asn Thr Thr Pro Ile Leu
1               5                   10
```

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Ser Ser Ser Asn Ile Gly Asn Asn Phe Val Tyr
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Asn Asn Gln Arg Pro Ser
1               5

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Ala Trp Asp Asp Ser Leu Ser Gly His Val Val
1               5                   10

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Tyr Tyr Leu His
1               5

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Ile Asn Pro Ser Asp Gly Ser Thr Arg Asn Ala Gln Lys Phe Glu
1               5                   10                  15

Gly

<210> SEQ ID NO 105
<211> LENGTH: 15
<212> TYPE: PRT
<213> ORGANISM: Artificial Sequence
<220> FEATURE:

<223> OTHER INFORMATION: Description of Artificial Sequence: Synthetic
       peptide

<400> SEQUENCE: 105

Asp Leu Glu Tyr Ile Gly Ser Gly Ser Leu Ser Trp Phe Asp Pro
1               5                   10                  15

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 106

Thr Gly Thr Ser Ser Asp Ile Gly Ala Tyr Glu Ser Val Ser
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 107

Asp Val Ser Ser Arg Pro Ser
1               5

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 108

Ser Ser Phe Thr Arg Gly Ser Thr Pro Tyr Val
1               5                   10

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 109

Asn Tyr Tyr Met His
1               5

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 110

Leu Leu Asn Pro Ser Gly Gly Tyr Thr Thr Tyr Ala Gln Arg Phe Gln
1               5                   10                  15

Gly

```
<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Pro Tyr Ser Ser Ser Trp Tyr Gly Ala Glu Tyr Phe Gln His
1               5                   10                  15

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Gly Thr Ser Ser Asp Val Gly Ala Tyr Asn Tyr Val Ser
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Val Ser Asp Arg Pro Ser
1               5

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Ser Tyr Thr Ser Ser Ser Ser Leu Tyr Val
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Gly Ser Ser Ser Asp Ile Gly Gly Tyr Asn Ser Val Ser
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 116

Asp Val Asn Glu Arg Pro Ser
1               5

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Ser Tyr Ser Val Phe Ser Pro Phe Leu
1               5                   10

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Tyr Tyr Leu His
1               5

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ile Ile Asn Pro Ser Asp Gly Ser Thr Arg Asn Ala Gln Lys Phe Glu
1               5                   10                  15

Gly

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Leu Glu Tyr Ile Gly Ser Gly Ser Leu Ser Trp Phe Asp Pro
1               5                   10                  15

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Thr Gly Thr Ser Ser Asp Leu Gly Ala Tyr Asp Tyr Val Ser
1               5                   10
```

```
<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Val Asn Asn Arg Pro Ser
1               5

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Ser Tyr Thr Ser Ser Ser Thr Leu Val Tyr Val
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Gly Thr Ser Ser Asp Val Gly Tyr Tyr Asp Ser Val Ser
1               5                   10

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asp Val Ser Lys Arg Pro Ser
1               5

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ser Ser Tyr Ser Asp Ser Ser Pro Phe Val
1               5                   10

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127
```

Thr Gly Ala Ser Ser Asp Val Gly Gly Tyr Asn Ser Val Ser
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asp Val Ser Asn Arg Pro Ser
1               5

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Ser Tyr Ala Gly Ser Asn Ile Val Tyr Val
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Thr Gly Thr Thr Ser Asp Ile Gly Gly Tyr Asn Ser Val Ser
1               5                   10

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Val Thr Tyr Arg Pro Ser
1               5

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Ser Tyr Thr Ser Gly Asn Ser Val Tyr Val
1               5                   10

<210> SEQ ID NO 133
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 133

Ser Tyr Tyr Met His
1               5

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Ile Asn Pro Ser Gly Gly Ser Thr Ser Tyr Ala Gln Lys Phe Gln
1               5                   10                  15

Gly

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Phe Ser Ser Trp Tyr Ala Tyr Gly Met Asp Val
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Ala Ser Gln Asp Ile Ser Ser Ala Leu Ala
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Ala Ser Thr Leu Glu Gly
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Gln Phe Arg Thr Tyr Pro Leu Thr
```

```
<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Tyr Tyr Met His
1               5

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Ile Asn Pro Ser Gly Gly Ser Thr Ser Tyr Ala Gln Lys Phe Gln
1               5                   10                  15

Gly

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Thr Leu Trp Phe Ser Glu Phe Asp Tyr
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Gly Ser Ser Ser Asn Ile Gly Asn Asn Tyr Val Ser
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Asn Asp Lys Arg Pro Ser
1               5

<210> SEQ ID NO 144
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 144

Gly Thr Trp Asp Ser Ser Leu Gly Trp Val
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Thr Gly Thr Ser Ser Asp Gly Gly Asp Tyr Asn Tyr Val Ser
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Glu Val Ser Asn Arg Pro Ser
1               5

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Ser Tyr Thr Ser Ser Ser Thr Leu Val Val
1               5                   10

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Tyr Tyr Met His
1               5

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Ile Asn Pro Ser Gly Gly Ser Thr Ser Tyr Ala Gln Lys Phe Gln
1               5                   10                  15
```

Gly

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Phe Ser Ser Trp Tyr Ala Tyr Gly Met Asp Val
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Arg Ala Ser Gln Asp Ile Ser Ser Ala Leu Ala
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Ala Ser Thr Leu Glu Gly
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Gln Phe Arg Thr Tyr Pro Leu Thr
1               5

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Thr Gly Thr Ser Ser Asp Val Gly Ala Tyr Asn Ser Val Ser
1               5                   10

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Asp Val Ile Gln Arg Pro Ser
1               5

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Ser Tyr Ala Ala Ser Thr Thr Phe Val
1               5                   10

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Tyr Tyr Met His
1               5

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ile Ile Asn Pro Ser Gly Gly Ser Thr Ser Tyr Ala Gln Lys Phe Gln
1               5                   10                  15

Gly

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Pro Tyr Ser Ser Ser Trp Tyr Gly Ala Glu Tyr Phe Gln His
1               5                   10                  15

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Gly Thr Ser Ser Asp Gly Gly Asp Tyr Asn Tyr Val Ser
1               5                   10

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Glu Val Ser Asn Arg Pro Ser
1               5

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Ser Tyr Thr Ser Ser Ser Thr Leu Val Val
1               5                   10

<210> SEQ ID NO 163
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Tyr Phe Met His
1

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Ile Asn Pro Ser Gly Gly Ser Thr Ser Tyr Ala Gln Lys Phe Gln
1               5                   10                  15

Gly

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asp Pro Tyr Ser Ser Ser Trp Tyr Gly Ala Glu Tyr Phe Gln His
1               5                   10                  15

<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Ser Gly Ser Ser Ser Asn Ile Gly Thr Asn Thr Val Asn
1               5                   10

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Asn Asn Gln Arg Pro Ser
1               5

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Ala Trp Asp Asp Ser Leu Asn Gly Gln Val
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Gly Thr Ser Ser Asp Val Gly Tyr Tyr Asp Ser Val Ser
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Val Ser Lys Arg Pro Ser
1               5

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Ser Tyr Ser Asp Ser Ser Pro Phe Val
1               5                   10

<210> SEQ ID NO 172

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Tyr Asp Met Ser
1               5

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Ile Ser Thr Ser Gly Gly Ser Thr Asn Tyr Ala Asp Ser Val Asn
1               5                   10                  15

Gly

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Glu Gly Ser Gly Trp Tyr Asp Ala Gly Tyr Phe Asp Tyr
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Ala Ser Gln Asp Ile Ser Asn Ser Leu Asn
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asp Ala Ser Thr Leu Gln Arg
1               5

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 177

Gln Gln Tyr Ala Asn Leu Pro Pro Ile Thr
1               5                   10

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Tyr Tyr Leu His
1               5

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ile Ile Asn Pro Ser Asp Gly Gly Thr Arg Tyr Ala Gln Lys Phe Gln
1               5                   10                  15

Asp

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Leu Glu Tyr Ile Gly Ser Gly Ser Leu Ser Trp Phe Asp Pro
1               5                   10                  15

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Thr Gly Thr Thr Ser Asp Ile Gly Gly Tyr Asn Ser Val Ser
1               5                   10

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Val Thr Tyr Arg Pro Ser
1               5

<210> SEQ ID NO 183
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Ser Tyr Thr Ser Gly Asn Ser Val Tyr Val
1               5                   10

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Asp Tyr Gly Met Ser
1               5

<210> SEQ ID NO 185
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Phe Val Gly Ser Lys Ala Ser Gly Gly Ala Ser Glu Asn Val Ala Ala
1               5                   10                  15

Val Gln Gly

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Leu Gly Thr Ser Gly Pro Tyr Phe Phe Asp Tyr
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Tyr Gly His Glu Leu Thr Asp Lys Tyr Val Ser
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 188

Glu Asp Thr Lys Arg Pro Ser
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Ala Trp Asp Ser Asn Thr Val Ile
1               5

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Gly Ser Ser Ser Asn Ile Gly Asn Asn Tyr Val Ser
1               5                   10

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Asp Asn Asn Glu Arg Pro Ser
1               5

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Ser Tyr Thr Asp Arg Asp Thr Pro Tyr Val
1               5                   10

<210> SEQ ID NO 193
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Phe Met His Trp Val Arg Gln Ala Pro Gly Gln Gly Leu Glu Trp Met
```

```
                35                  40                  45
Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Glu Leu Leu Trp Phe Gly Glu Leu Ser Gly Ala Phe
            100                 105                 110

Asp Ile Trp Gly Gln Gly Thr Met Val Thr Val Ser Ser
        115                 120                 125

<210> SEQ ID NO 194
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Ser Phe Thr Ile Ser Asn Leu Gln Pro
65                  70                  75                  80

Glu Asp Ile Ala Thr Tyr Tyr Cys Gln Gln Ser Ala Asn Leu Pro Ile
                85                  90                  95

Thr Phe Gly Gln Gly Thr Lys Val Glu Ile Lys
            100                 105

<210> SEQ ID NO 195
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Asn Phe Phe Met His
1               5

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ile Ile Asn Pro Ser Gly Gly Ser Thr Ser Tyr Ala Gln Lys Phe Gln
1               5                   10                  15

Gly
```

<210> SEQ ID NO 197
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Asp Arg Glu Leu Leu Trp Phe Gly Glu Leu Ser Gly Ala Phe Asp Ile
1               5                   10                  15

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gln Ala Ser Gln Asp Ile Ser Lys Tyr Leu Asn
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Asp Ala Ser Asn Leu Glu Thr
1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gln Gln Ser Ala Asn Leu Pro Ile Thr
1               5

<210> SEQ ID NO 201
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Gln Ser Gly Ala Glu Val Lys Lys Pro Gly Ala
1               5                   10                  15

Ser Val Thr Leu Ser Cys Lys Ala Ser Gly His Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Gly Gly Gly Thr Ser Tyr Ala Gln Lys Phe
    50                  55                  60

His Asp Arg Val Ala Met Thr Arg Asp Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Leu Tyr Ser Ala Tyr Asp Ser Pro Ser Asp Leu Trp Gly
            100                 105                 110

Gln Gly Thr Leu Val Thr Val Ser Ser
            115                 120

<210> SEQ ID NO 202
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gln Ser Val Leu Thr Gln Pro Ala Ser Val Ser Ala Ser Pro Gly Gln
1               5                   10                  15

Ser Ile Thr Ile Ser Cys Thr Gly Ala Ser Ser Asp Ile Gly Gly Tyr
                20                  25                  30

Asp Tyr Val Ser Trp Tyr Gln Gln His Ser Gly Lys Ala Pro Lys Leu
            35                  40                  45

Met Ile Tyr Glu Ala Ser Lys Arg Pro Ser Gly Val Ser His Arg Phe
        50                  55                  60

Ser Gly Ser Lys Ser Gly Asn Thr Ala Ser Leu Ile Ile Ser Gly Leu
65                  70                  75                  80

Gln Ala Glu Asp Glu Ala Asp Tyr Tyr Cys Ser Ser His Thr Thr Ser
                85                  90                  95

Ser Thr Trp Val Phe Gly Gly Gly Thr Lys Leu Thr Val Leu
            100                 105                 110

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Tyr Tyr Met His
1               5

<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ile Ile Asn Pro Gly Gly Gly Thr Ser Tyr Ala Gln Lys Phe His
1               5                   10                  15

Asp

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Leu Tyr Ser Ala Tyr Asp Ser Pro Ser Asp Leu
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Thr Gly Ala Ser Ser Asp Ile Gly Gly Tyr Asp Tyr Val Ser
1               5                   10

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Glu Ala Ser Lys Arg Pro Ser
1               5

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Ser His Thr Thr Ser Ser Thr Trp Val
1               5                   10

<210> SEQ ID NO 209
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Asp Ile Gln Met Thr Gln Ser Pro Ser Ser Leu Ser Ala Ser Leu Gly
1               5                   10                  15

Asp Arg Val Thr Ile Thr Cys Arg Ala Asn Gln Ser Ile Ser Arg Tyr
            20                  25                  30

Leu Asn Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Asn Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ser
                85                  90                  95

```
Ile Thr Phe Gly Gln Gly Thr Arg Leu Glu Ile Lys
            100                 105
```

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

```
Arg Ala Asn Gln Ser Ile Ser Arg Tyr Leu Asn
1               5                   10
```

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

```
Ala Ala Ser Ser Leu Gln Ser
1               5
```

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

```
Gln Gln Ser Tyr Ser Thr Pro Ser Ile Thr
1               5                   10
```

<210> SEQ ID NO 213
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

```
Asn Phe Met Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Gly Tyr
            20                  25                  30

Ser Ser Val Ser Trp Tyr Gln Gln His Pro Gly Lys Ala Pro Lys Leu
        35                  40                  45

Ile Ile Tyr Asp Val Thr Glu Arg Pro Ser Gly Val Pro Asp Arg Phe
    50                  55                  60

Ser Gly Ser Lys Ser Gly Asp Thr Ala Thr Leu Thr Ile Ser Gly Leu
65                  70                  75                  80

Gln Ala Glu Asp Glu Ala Asp Tyr Phe Cys Ser Ser Tyr Ala Gly Val
                85                  90                  95

Tyr Thr Tyr Val Phe Gly Thr Gly Thr Lys Val Thr Val Leu
            100                 105                 110
```

```
<210> SEQ ID NO 214
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Gly Thr Ser Ser Asp Ile Gly Gly Tyr Ser Ser Val Ser
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Asp Val Thr Glu Arg Pro Ser
1               5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Ser Tyr Ala Gly Val Tyr Thr Tyr Val
1               5                   10

<210> SEQ ID NO 217
<211> LENGTH: 249
<212> TYPE: PRT
<213> ORGANISM: Homo sapiens

<400> SEQUENCE: 217

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
                20                  25                  30

Asn Thr Val Cys Arg Pro Cys Gly Pro Gly Phe Tyr Asn Asp Val Val
            35                  40                  45

Ser Ser Lys Pro Cys Lys Pro Cys Thr Trp Cys Asn Leu Arg Ser Gly
        50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160
```

```
Val Gln Pro Thr Glu Ala Trp Pro Arg Thr Ser Gln Gly Pro Ser Thr
            165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245

<210> SEQ ID NO 218
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Cys Pro Ser Cys Pro
1               5

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Cys Pro Pro Cys Pro
1               5
```

ANTI-OX40 BINDING PROTEINS

CROSS-REFERENCE TO RELATED APPLICATIONS

This application is a National Stage Application of International Application No. PCT/US2017/045788, filed Aug. 7, 2017, which claims priority to U.S. Provisional Application No. 62/371,993, filed on Aug. 8, 2016, and entitled "Anti-OX40 Binding Proteins", the entire contents of each of which are incorporated herein by reference in their entirety.

SEQUENCE LISTING

The instant application contains a Sequence Listing which has been submitted electronically in ASCII format via EFS-Web and is hereby incorporated by reference in its entirety. Said ASCII copy, created on Feb. 7, 2019, is named Sequence_Listing_S103014_2040US.PCT.txt and is 100 kilobytes in size.

BACKGROUND

OX40 (also known as CD 134, TNFRSF4, ACT35 or TXGP1L) is a member of the TNF receptor superfamily, which includes 4-1BB, CD27, CD30 and CD40. The extracellular ligand binding domain of OX40 is composed of 3 full cysteine-rich domains (CRDs) and a partial, fourth C-terminal CRD (Bodmer et al, 2002, *Trends Biochem. Sci.*, 27, 19-26). The ligand for OX40, OX40L, is a member of the TNF family and is expressed on activated antigen presenting cells (APC), including B cells, macrophages, endothelial cells and dendritic cells (DC). OX40 is a membrane-bound receptor; however a soluble isoform has also been detected (Taylor and Schwarz, 2001, *J. Immunol. Methods*, 255, 67-72). OX40 is not expressed on resting T cells, but is transiently expressed on activated T cells after ligation of the T cell receptor (TCR).

OX40 is a major costimulatory receptor with sequential engagement of CD28 and OX40 resulting in optimal T cell proliferation and survival. Ligation of OX40 on activated T cells leads to enhanced cytokine production and proliferation of both CD4+ and CD8+ T cells (Gramaglia et al., 2000, *J. Immunol*, 165, 3043-3050, Bansal-Pakala et al., 2004, *J. Immunol.*, 172, 4821-425) and can contribute to both ongoing Th1 and Th2 responses (Gramaglia et al., 1998, *J. Immunol.*, 161, 6510-6517, Arestides et al, 2002, *Eur. J. Immunol.* 32, 2874-2880). OX40 costimulation prolongs T cell survival beyond the initial effector phase of the immune response and increases the number of memory T cells through inhibition of effector T cell death.

When immune activation is excessive or uncontrolled, pathological allergy, asthma, inflammation, autoimmune and other related diseases may occur.

Tumor cells commonly 'escape' the immune system by induction of an active immune tolerance largely mediated by regulatory T lymphocytes (Tregs et al. *Immunol Rev.* 2011; 241:104-118). Therefore, the balance between effector (i.e., direct or indirect eradication of tumor cells) T lymphocytes (Teffs) and tolerogenic (i.e., suppression of Teffs effector function and survival) Tregs appears to be important for effective anti-tumor immunotherapy. In other words, an effective anti-tumor immune response can be obtained by enhancing effector function of tumor-specific Teffs and/or by attenuating suppressive function of tumor-specific Tregs. A key receptor that has been shown to mediate these responses is OX40 (CD134). (Sugamura et al., *Nature Rev. Imm.* 2004; 4: 420-431).

In vivo ligation of mouse CD134 receptor (by either soluble mouse OX40 ligand (OX40L)-immunoglobulin fusion proteins or mouse OX40L mimetics, such as anti-mouse CD134-specific antibodies) in tumor-bearing mice enhances anti-tumor immunity, leads to tumor-free survival in mouse models of various murine malignant tumor cell lines, e.g., lymphoma, melanoma, sarcoma, colon cancer, breast cancer, and glioma (Sugamura et al. *Nature Rev. Imm.* 2004; 4:420631). Al-Shamkhani et al. (*Eur. J. Chem.* 1996; 26: 1695-1699) used an anti-OX40 antibody called OX86, which did not block OX40L-binding, in order to explore differential expression of OX40 on activated mouse T-cells; and Hirschhorn-Cymerman et al. (*J. Exp. Med.* 2009; 206: 1103-1116) used OX86 together with cyclophosphamide in a mouse model as a potential chemoimmunotherapy.

Thus, there remains a need in the art for effective treatments based on OX40, particularly anti-OX40 antibodies.

SUMMARY OF THE INVENTION

The invention provides antibodies that specifically bind to OX40, including human OX40.

In a first aspect, the invention features an isolated anti-OX40 antibody, or an antigen-binding fragment thereof, comprising a heavy chain variable domain comprising a heavy chain CDR set (CDR1, CDR2, and CDR3) selected from the group consisting of SEQ ID Nos: 49, 50 and 51; SEQ ID Nos: 55, 56 and 57; SEQ ID Nos: 61, 62 and 63; SEQ ID Nos: 67, 68 and 69; SEQ ID Nos: 73, 74 and 75; SEQ ID Nos: 79, 80 and 81; SEQ ID Nos: 85, 86 and 87; SEQ ID Nos: 91, 92 and 93; SEQ ID Nos: 103, 104 and 105; SEQ ID Nos: 109, 110 and 111; SEQ ID Nos: 118, 119 and 120; SEQ ID Nos: 133, 134 and 135; SEQ ID Nos: 139, 140 and 141; SEQ ID Nos: 148, 149, and 150; SEQ ID Nos: 157, 158 and 159; SEQ ID Nos: 163, 164 and 165; SEQ ID Nos: 172, 173 and 174; SEQ ID Nos: 178, 179 and 180; SEQ ID Nos: 184, 185 and 186; SEQ ID Nos. 195, 196 and 197; and SEQ ID Nos. 203, 204 and 205; and a light chain variable domain comprising a light chain CDR set (CDR1, CDR2, and CDR3) selected from the group consisting of SEQ ID Nos: 52, 53 and 54; SEQ ID Nos: 58, 59 and 60; SEQ ID Nos: 64, 65 and 66; SEQ ID Nos: 70, 71 and 72; SEQ ID Nos: 76, 77 and 78; SEQ ID Nos: 82, 83 and 84; SEQ ID Nos: 88, 89 and 90; SEQ ID Nos: 94, 95 and 96; SEQ ID Nos: 97, 98 and 99; SEQ ID Nos: 100, 101 and 102; SEQ ID Nos: 106, 107 and 108; SEQ ID Nos: 112, 113 and 114; SEQ ID Nos: 115, 116 and 117; SEQ ID Nos: 121, 122 and 123; SEQ ID Nos: 124, 125 and 126; SEQ ID Nos: 127, 128 and 129; SEQ ID Nos: 130, 131 and 132; SEQ ID Nos: 136, 137 and 138; SEQ ID Nos: 142, 143 and 144; SEQ ID Nos: 145, 146 and 147; SEQ ID Nos: 151, 152 and 153; SEQ ID Nos: 154, 155 and 156; SEQ ID Nos: 160, 161 and 162; SEQ ID Nos: 166, 167 and 168; SEQ ID Nos: 169, 170 and 171; SEQ ID Nos: 175, 176 and 177; SEQ ID Nos: 181, 182 and 183; SEQ ID Nos: 187, 188 and 189; SEQ ID Nos: 190, 191 and 192; SEQ ID Nos. 198, 199 and 200; SEQ ID Nos. 206, 207 and 208; SEQ ID Nos. 210, 211 and 212; and SEQ ID Nos. 214, 215 and 216. In one embodiment, the heavy chain variable domain comprises an amino acid sequence that is at least 95% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and a light chain variable domain comprising an amino acid sequence that is at least 95% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the heavy chain variable domain comprises an amino acid sequence that is at least 96% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and the light chain variable domain comprises an amino acid sequence that is at least 96% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the heavy chain variable domain comprises an amino acid sequence that is at least 97% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and the light chain variable domain comprises an amino acid sequence that is at least 97% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the heavy chain variable domain comprises an amino acid sequence that is at least 98% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprises a light chain variable domain comprising an amino acid sequence that is at least 98% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the heavy chain variable domain comprises an amino acid sequence that is at least 99% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprises a light chain variable domain comprising an amino acid sequence that is at least 99% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the heavy chain variable domain comprises an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprises a light chain variable domain comprising an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In a further embodiment, the invention provides an isolated anti-OX40 antibody, or an antigen-binding fragment thereof, comprising a heavy chain CDR set/light chain CDR set selected from the group consisting of SEQ ID Nos: 49, 50 and 51/SEQ ID Nos: 52, 53 and 54; SEQ ID Nos: 55, 56 and 57/SEQ ID Nos: 58, 59 and 60; SEQ ID Nos: 61, 62 and 63/SEQ ID Nos: 64, 65 and 66; SEQ ID Nos: 67, 68 and 69/SEQ ID Nos: 70, 71 and 72; SEQ ID Nos: 73, 74 and 75/SEQ ID Nos: 76, 77 and 78; SEQ ID Nos: 79, 80 and 81/SEQ ID Nos: 82, 83 and 84; SEQ ID Nos: 85, 86 and 87/SEQ ID Nos: 88, 89 and 90; SEQ ID Nos: 91, 92 and 93/SEQ ID Nos: SEQ ID Nos: 94, 95 and 96; SEQ ID Nos:

67, 68 and 69/SEQ ID Nos: 97, 98, and 99; SEQ ID Nos: 55, 56 and 57/SEQ ID Nos: 100, 101 and 102; SEQ ID Nos: 103, 104 and 105/SEQ ID Nos: 106, 107 and 108; SEQ ID Nos: 109, 110 and 111/SEQ ID Nos: 112, 113 and 114; SEQ ID Nos: 67, 68 and 69/SEQ ID Nos: 115, 116 and 117; SEQ ID Nos: 118, 119 and 120/SEQ ID Nos: 121, 122 and 123; SEQ ID Nos: 67, 68 and 69/SEQ ID Nos: 124, 125 and 126; SEQ ID Nos: 67, 68 and 69/SEQ ID Nos: 127, 128 and 129; SEQ ID Nos: 67, 68 and 69/SEQ ID Nos: 130, 131 and 132; SEQ ID Nos: 133, 134 and 135/SEQ ID Nos: 136, 137 and 138; SEQ ID Nos: 139, 140 and 141/SEQ ID Nos: 142, 143 and 144; SEQ ID Nos: 55, 56 and 57/SEQ ID Nos: 145, 146 and 147; SEQ ID Nos: 148, 149 and 150/SEQ ID Nos: 151, 152 and 153; SEQ ID Nos: 67, 68 and 69/SEQ ID Nos: 154, 155 and 156; SEQ ID Nos: 157, 158 and 159/SEQ ID Nos: 160, 161 and 162; SEQ ID Nos: 163, 164 and 165/SEQ ID Nos: 166, 167 and 168; SEQ ID Nos: 67, 68 and 69/SEQ ID Nos: 169, 170 and 171; SEQ ID Nos: 172, 173 and 174/SEQ ID Nos: 175, 176 and 177; SEQ ID Nos: 178, 179 and 180/SEQ ID Nos: 181, 182 and 183; SEQ ID Nos: 184, 185 and 186/SEQ ID Nos: 187, 188 and 189; SEQ ID Nos: 67, 68 and 69/SEQ ID Nos: 190, 191 and 192; SEQ ID Nos: 195, 196 and 197/SEQ ID Nos: 198, 199 and 200; SEQ ID Nos: 203, 204 and 205/SEQ ID Nos: 206, 207 and 208; SEQ ID Nos: 61, 62 and 63/SEQ ID Nos: 210, 211 and 212; SEQ ID Nos: 67, 68 and 69/SEQ ID Nos: 214, 215 and 216.

In another aspect, the invention features an anti-OX40 antibody, or an antigen-binding fragment thereof, comprising a heavy chain variable domain comprising an amino acid sequence that is at least 95% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprising a light chain variable domain comprising an amino acid sequence that is at least 95% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In another aspect, the invention features an anti-OX40 antibody, or an antigen-binding fragment thereof, comprising a heavy chain variable domain comprising an amino acid sequence that is at least 96% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprising a light chain variable domain comprising an amino acid sequence that is at least 96% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In another aspect, the invention features an anti-OX40 antibody, or an antigen-binding fragment thereof, comprising a heavy chain variable domain comprising an amino acid sequence that is at least 97% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprising a light chain variable domain comprising an amino acid sequence that is at least 97% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In another aspect, the invention features an anti-OX40 antibody, or an antigen-binding fragment thereof, comprising a heavy chain variable domain comprising an amino acid sequence that is at least 98% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprising a light chain variable domain comprising an amino acid sequence that is at least 98% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In another aspect, the invention features an anti-OX40 antibody, or an antigen-binding fragment thereof, comprising a heavy chain variable domain comprising an amino acid sequence that is at least 99% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprising a light chain variable domain comprising an amino acid sequence that is at least 99% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In another aspect, the invention features an anti-OX40 antibody, or an antigen-binding fragment thereof, comprising a heavy chain variable domain comprising an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201; and comprising a light chain variable domain comprising an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In one embodiment of any one of the above aspects or embodiments, the antibody, or antigen-binding fragment thereof, has a $K_D$ of at least $1 \times 10^{-6}$ M.

In another embodiment of any one of the above aspects or embodiments, the antibody, or antigen-binding fragment thereof, is an isolated human antibody.

In one embodiment of any one of the above aspects or embodiments, the anti-OX40 antibody is an IgG. In a further embodiment, the antibody is an IgG1, IgG2, IgG3 or an IgG4 isotype.

In one embodiment of any one of the above aspects or embodiments, the antigen-binding fragment is a Fab fragment or an scFv.

In another embodiment, the invention features a pharmaceutical composition comprising the anti-OX40 antibody, or antibody fragment thereof, of any one of the above aspects or embodiments, and a pharmaceutically acceptable carrier.

In one embodiment, the invention features a method for treating a subject having cancer, the method comprising administering an effective amount of the anti-OX40 antibody, or antigen-binding fragment thereof, of any one of the above aspects or embodiments to the subject. In one embodiment, the cancer is selected from the group consisting of prostate cancer, breast cancer, ovarian cancer, head and neck cancer, bladder cancer, melanoma, colorectal cancer, pancreatic cancer, lung cancer, leiomyoma, leiomyosarcoma, glioma, glioblastoma, esophageal cancer, liver cancer, kidney cancer, stomach cancer, colon cancer, cervical cancer, uterine cancer, liver cancer and a hematological cancer. In another further embodiment, the cancer is selected from the group consisting of B chronic lymphocytic leukemia (B-CLL), B and T acute lymphocytic leukemia (ALL), acute myeloid leukemia (AML), chronic lymphocytic leukemia (CLL), chronic myelogenous leukemia (CML), hairy cell leukemia (HCL), myeloproliferative disorder/neoplasm (MPDS), myelodysplasia syndrome, non-Hodgkin's lymphoma (NHL), including Burkitt's lymphoma (BL), Waldenstrom's Macroglobulinemia, mantle cell lymphoma, AIDS-related lymphoma, Hodgkin's Lymphoma (HL), T cell lymphoma (TCL), multiple myeloma (MM), plasma cell myeloma, plamocytoma, giant cell myeloma, heavy-chain myeloma, and light chain or Bence-Jones myeloma.

In one embodiment, the invention features a method for treating a subject having an inflammatory disease, the method comprising administering an effective amount of the anti-OX40 antibody, or antigen-binding fragment thereof, of any one of the above aspects or embodiments to the subject.

In a further embodiment, the inflammatory disease is selected from the group consisting of allergy, COPD, autoimmune disease, rheumatoid arthritis, asthma, graft versus host disease, Crohn's disease, ulcerative colitis, type-1 diabetes, multiple sclerosis, Systemic lupus erythematosis, lupus nephritis, Myasthenia Gravis, Grave's disease, transplant rejection, Wegener's granulomatosis, Henoch-Schonlein purpura, systemic sclerosis, and viral-induced lung inflammation.

In one embodiment, the invention features a method for treating a subject having an infection, the method comprising administering an effective amount of the anti-OX40 antibody, or antigen-binding fragment thereof, of any one of the above aspects or embodiments to the subject.

In one embodiment, the invention features a method for treating a disease requiring either stimulation of immune responses or suppression, the method comprising administering an effective amount of the anti-OX40 antibody, or antigen-binding fragment thereof, of any one of the above aspects or embodiments to the subject. In a further embodiment, the disease is selected from the group consisting of cancer, an inflammatory disease, and a viral infection.

Also included in the invention are nucleic acids encoding the amino acid sequences disclosed herein, as well as methods of making the antibodies and fragments of the invention.

DESCRIPTION OF THE DRAWINGS

As shown in FIG. 2A, unstimulated cells, isotype control FeH3 antibody (Ctrl FeH3) and polyclonal anti-OX40 antibody did not show an increase in RLUs, indicating that the NFkB pathway was not activated. The positive controls, soluble anti-Histidine+purified rhOX40L (rhOX40L+αHis) and soluble TNFα, showed higher RLUs, indicating an increase in NFkB activity.

As shown in FIG. 2B, all of the OX40 clones showed an increase in RLUs over the negative control values. Clones 1C4, 4D7 1D9 and 1B2 showed the strongest NFkB activation (>50% of signal observed with purified rhOX40L+ anti-His).

As shown in FIG. 3A, unstimulated cells, isotype control FeH3 antibody (Ctrl FeH3) did not show an increase in RLUs, indicating that the NFkB pathway was not activated. The positive controls, soluble anti-Histidine+purified rhOX40L (rhOX40L+αHis) and soluble TNFα, showed higher RLUs, indicating an increase in NFkB activity.

As shown in FIG. 3B, most of the OX40 clones showed an increase in RLUs over the negative control values. In particular clones 1A11, 1C4, 4D7, 1D9, 5C11, 2B4, 4D9, 3C10 and 1B2 were among the most active.

As shown in FIG. 4A and FIG. 4B, a number of anti-OX40 clones showed significant T cell co-stimulation. Among those clones showing T cell co-stimulation, clones 2B4, 4D7, 2B3, 4G9 and 1B1 showed the most robust agonist activity.

DETAILED DESCRIPTION

Definitions

Figure 1:
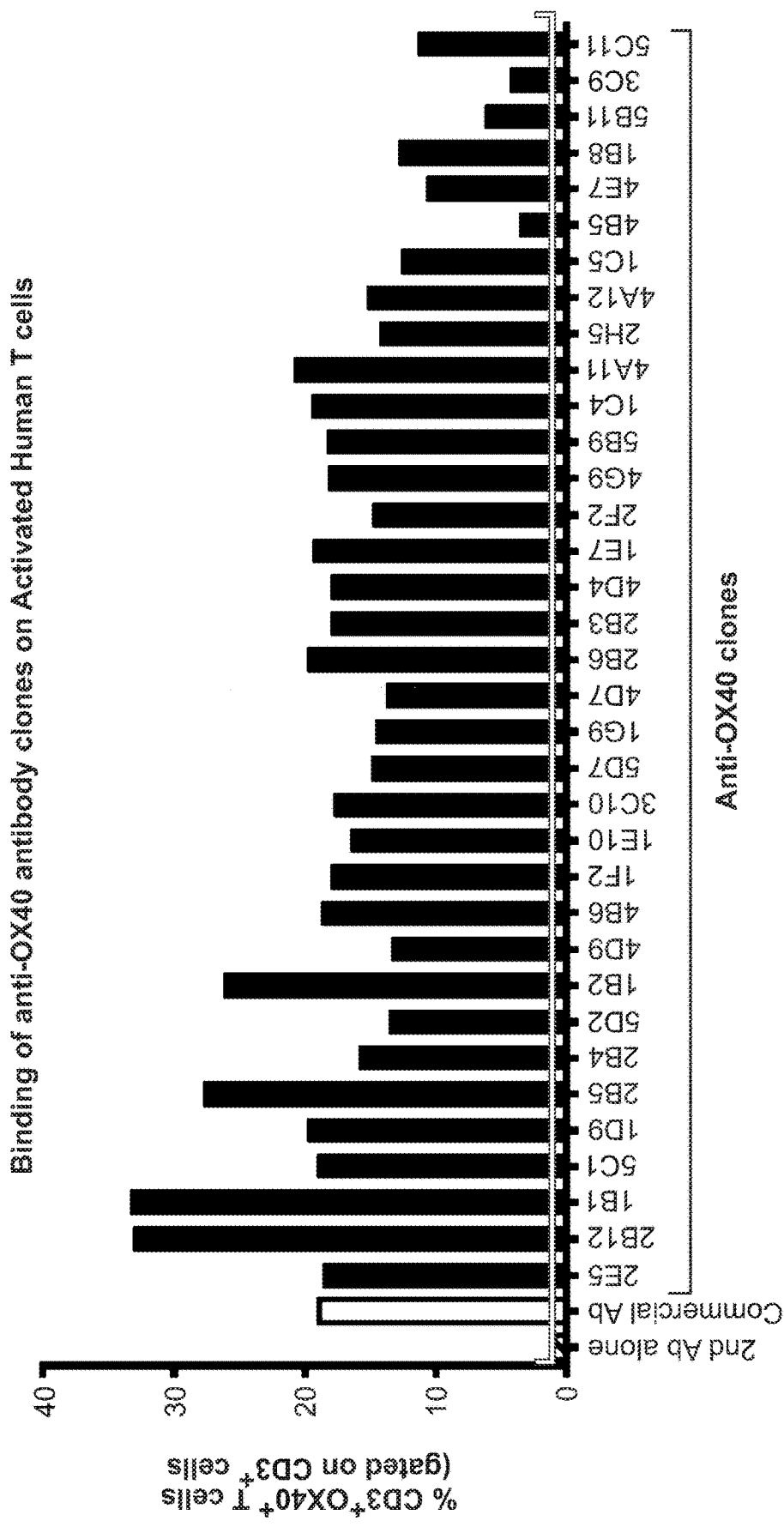
FIG. 1 is a graph that shows the binding of anti-OX40 antibody clones on activated human T-cells measured by the percent CD3+OX40+ T cells. The anti-OX40 clones that were tested are shown on the x-axis. Secondary antibody alone was used as a negative control. A commercially available APC-labelled anti-human OX40 (clone Ber-ACT35) was used as positive control.

An "antigen binding protein" is a protein comprising a portion that binds to an antigen and, optionally, a scaffold or framework portion that allows the antigen binding portion to adopt a confirmation that promotes binding of the antigen binding protein to the antigen. Examples of antigen binding proteins include antibodies, antibody fragments (e.g., an antigen binding fragment of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

The term "antibody" is synonymous with immunoglobulin and is to be understood as commonly known in the art. The basic antibody structural unit is a tetramer. Each tetramer is composed of two identical pairs of polypeptide chains, each pair having one "light" (about 25 kDa) and one "heavy" chain (about 50-70 kDa). Generally, the amino-terminal portion of each antibody chain includes a variable region that is primarily responsible for antigen recognition. The carboxy-terminal portion of each chain defines a constant region, e.g., responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 3 or more amino acids.

The variable regions of each heavy/light chain pair (VH/VL), respectively, form the antigen binding site. The variable regions of antibody heavy and light chains (VH/VL) exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is known in the art, including, for example, definitions as described in Kabat et al. in Sequences of Proteins of Immunological Interest, $5^{th}$ Ed., US Dept. of Health and Human Services, PHS, NIH, NIH Publication no. 91-3242, 1991 (herein referred to as "Kabat numbering"). For example, the CDR regions of an antibody can be determined according to Kabat numbering.

The terms "intact antibody" or "full length antibody" refer to an antibody composed of two identical antibody light chains and two identical antibody heavy chains that each contain an Fc region.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein). Generally the variable regions, particularly the CDRs, of an antibody interact with the epitope.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

The terms "anti-OX40 antibody" and "an antibody that binds to OX40" refer to an antibody that is capable of binding OX40 with sufficient affinity such that the antibody is useful as a diagnostic and/or therapeutic agent in targeting OX40, including human OX40.

The term "monospecific", as used herein, refers to an antibody, or antigen binding fragment thereof, that displays an affinity for one particular epitope. In contrast, a bispecific antibody, or antigen-binding fragment thereof, displays affinity for two different epitopes. In one embodiment, the methods and compositions described herein are useful for intracellular delivery of a monospecific antibody, or antigen-binding fragment thereof. In one embodiment, the anti-OX40 antibody, or antigen-binding fragment thereof, of the invention is monospecific.

A "multi-specific antibody" is an antibody that recognizes more than one epitope on one or more antigens. A subclass of this type of antibody is a "bispecific antibody" which recognizes two distinct epitopes on the same or different antigens.

The terms "specific binding", "specifically binds" or "specifically binding", as used herein in the context of an antibody, refer to non-covalent or covalent preferential binding of an antibody to an antigen relative to other molecules or moieties (e.g., an antibody specifically binds to a particular antigen relative to other available antigens). In one embodiment, an antibody specifically binds to an antigen (e.g., OX40) if it binds to the antigen with a dissociation constant $K_D$ of $10^{-5}$ M or less (e.g., $10^{-6}$ M or less, $10^{-7}$ M or less, $10^{-8}$ M or less, $10^{-9}$ M or less, or $10^{-10}$ M or less).

The term "human antibody", as used herein, refers to an antibody, or an antigen binding fragment of an antibody, comprising heavy and lights chains derived from human immunoglobulin sequences. Human antibodies may be identified in a variety of ways, examples of which are described below, including through the immunization with an antigen of interest of a mouse that is genetically modified to express antibodies derived from human heavy and/or light chain-encoding genes. In one embodiment, a human antibody is made using recombinant methods such that the glycosylation pattern of the antibody is different than an antibody having the same sequence if it were to exist in nature.

The term "chimeric antibody" refers to an antibody that contains one or more regions derived from a particular source or species, and one or more regions derived from a different source or species.

The term "humanized antibody" refers to antibodies which comprise heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody.

A "humanized antibody" refers to an antibody having a sequence that differs from the sequence of an antibody derived from a non-human species by one or more amino acid substitutions, deletions, and/or additions. Generally, a humanized antibody is less likely to induce an immune response, and/or induces a less severe immune response, as compared to the non-human species antibody, e.g., a murine or chimeric antibody, when it is administered to a human subject. In one embodiment, certain amino acids in the framework and constant domains of the heavy and/or light chains of the non-human species antibody are mutated to produce the humanized antibody. Examples of how to make humanized antibodies may be found in U.S. Pat. Nos. 6,054,297, 5,886,152 and 5,877,293.

An "antibody fragment", "antibody portion", "antigen-binding fragment of an antibody", or "antigen-binding portion of an antibody" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and In one embodiment, the antibody fragment is an scFv. A single-chain antibody (scFv) is an antibody in which a $V_L$ and a $V_H$ region are joined via a linker (e.g., a synthetic sequence of amino acid residues) to form a continuous protein chain (see e.g., Bird et al. (1988) Science 242:423-426; and Huston et al. (1988) Proc. Natl. Acad. Sci. USA 85:5879-5883)).

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App Pub 20/0202512; 2004/0202995; 2004/0038291; 2004/0009507; 2003/0039958, and Ward et al., Nature 341:544-546, 1989).

Diabodies are bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment thereof, as described herein.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell (or cell line) transfected with an expression vector (or possibly more than one expression vector) comprising the coding sequence of the antibody, or a portion thereof (e.g., a DNA sequence encoding a heavy chain or a light chain variable region as described herein). In one embodiment, said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof that binds OX40, which is sufficient to effect treatment of a disease associated with OX40 signaling, as described herein, when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art.

The term "isolated" refers to a protein (e.g., an antibody) that is substantially free of other cellular material. In one embodiment, an isolated antibody is substantially free of other proteins from the same species. In one embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

As used herein, the phrase "OX40 activation" refers to activation of the OX40 receptor. Generally, OX40 activation results in signal transduction.

The term "OX40," as used herein, refers to any native OX40 from any vertebrate source, including mammals such as primates (e.g., humans) and rodents (e.g., mice and rats), unless otherwise indicated. The term encompasses "full-length," unprocessed OX40 as well as any form of OX40 that results from processing in the cell. The term also encompasses naturally occurring variants of OX40, for example, splice variants or allelic variants. The amino acid sequence of an exemplary human OX40 lacking the signal peptide is shown in SEQ ID NO. 217 (LHCVGDTYPSN-DRCCHECRPGNGMVSRCSRSQNTVCRPCGPG-FYNDVVSSKPCKPC TWCNLRSGSERKQLCTATQDT-VCRCRAGTQPLDSYKPGVDCAPCPPGHFSPGDNQA CKPWTNCTLAGKHTLQPASNSSDAICEDRDP-PATQPQETQGPPARPITVQPTEAWPRT SQGP-STRPVEVPGGRAVAAILGLGLVLGLLGPLAILLALYL-LRRDQRLPPDAHKPPGG GSFRTPIQEEQADAHSTLAKI). In one embodiment, the antibody, or fragment, of the invention binds to OX40 as set forth in SEQ ID NO: 217.

OX40 Antigen Binding Proteins

The present invention pertains to OX40 binding proteins, particularly anti-OX40 antibodies, or antigen-binding portions thereof, and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human OX40, to stimulate OX40 activity, either in vitro or in vivo, and to prevent or treat disorders such as cancer are also encompassed by the invention.

As described in Table 1 below, included in the invention are novel human antibody heavy and light chain variable regions and CDRs that are specific to human OX40.

In one embodiment, the invention provides an anti-OX40 antibody, or an antigen-binding fragment thereof, that comprises a heavy chain having a variable domain comprising an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201. In one embodiment, the invention provides an anti-OX40 antibody, or an antigen-binding fragment thereof, that comprises a light chain having a variable domain comprising an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the invention provides an anti-OX40 antibody, or an antigen-binding fragment thereof, that comprises a light chain having a variable domain comprising an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213; and a heavy chain having a variable domain comprising an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201.

In one embodiment, the present disclosure provides a human antibody of an IgG class that binds to a human OX40 epitope with a binding affinity of at least $10^{-6}$M, where the antibody, or antigen-binding fragment, has a heavy chain variable domain sequence which is at least 95% identical, at least 96% identical, at least 97% identical, at least 98% identical, or at least 99% identical, or identical, to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and has a light chain variable domain sequence that is at least 95% identical, at least 96% identical, at least 97% identical, at least 98% identical, or at least 99% identical, or identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In one embodiment, the invention features an isolated anti-hOX40 human antibody comprising a heavy chain/light chain variable domain amino acid sequence selected from the group consisting of SEQ ID NO. 1/SEQ ID NO. 2 (called OX1A11 herein), SEQ ID NO. 3/SEQ ID NO. 4 (called OX1B1 herein), SEQ ID NO. 5/SEQ ID NO. 6 (called OX1B2 herein), SEQ ID NO. 7/SEQ ID NO. 8 (called OX1B3 herein), SEQ ID NO. 9/SEQ ID NO. 10 (called OX1C4 herein), SEQ ID NO. 11/SEQ ID NO. 12 (called OX1C5 herein), SEQ ID NO. 13/SEQ ID NO. 14 (called OX1D9 herein), SEQ ID NO. 15/SEQ ID NO. 16 (called OX1E10 herein), SEQ ID NO. 7/SEQ ID NO. 17 (called OX1E7 herein), SEQ ID NO. 3/SEQ ID NO. 18 (called OX1F2 herein), SEQ ID NO. 19/SEQ ID NO. 20 (called OX1G9), SEQ ID NO. 21/SEQ ID NO. 22 (called OX2B12 herein), SEQ ID NO. 7/SEQ ID NO. 23 (called OX2B3 herein), SEQ ID NO. 24/SEQ ID NO. 25 (called OX2B4 herein), SEQ ID NO. 7/SEQ ID NO. 26 (called OX2B6 herein), SEQ ID NO. 7/SEQ ID NO. 27 (called OX2F2 herein), SEQ ID NO. 7/SEQ ID NO. 28 (called OX2G2 herein), SEQ ID NO. 29/SEQ ID NO. 30 (called OX3C10 herein), SEQ ID NO. 31/SEQ ID NO. 32 (called OX4A11 herein), SEQ ID NO. 3/SEQ ID NO. 33 (called OX4A12 herein), SEQ ID NO. 34/SEQ ID NO. 35 (called OX4B6 herein), SEQ ID NO. 7/SEQ ID NO. 36 (called OX4D4 herein), SEQ ID NO. 37/SEQ ID NO. 38 (called OX4D7 herein), SEQ ID NO. 39/SEQ ID NO. 40 (called OX4D9 herein), SEQ ID NO. 7/SEQ ID NO. 41 (called OX4G9 herein), SEQ ID NO. 42/SEQ ID NO. 43 (called OX4H4 herein), SEQ ID NO. 44/SEQ ID NO. 45 (called OX5B9 herein), SEQ ID NO. 46/SEQ ID NO. 47 (called OX5C1 herein), SEQ ID NO. 7/SEQ ID NO. 48 (called OX5D7 herein), SEQ ID NO. 193/SEQ ID NO. 194 (called OX4B5 herein), SEQ ID NO. 201/SEQ ID NO. 202 (called OX2E5 herein), SEQ ID NO. 5/SEQ ID NO. 209 (called OX2B5 herein), and SEQ ID NO. 7/SEQ ID NO. 213 (called OX5C11 herein).

Complementarity determining regions (CDRs) are known as hypervariable regions both in the light chain and the heavy chain variable domains of an antibody. The more highly conserved portions of variable domains are called the framework (FR). Complementarity determining regions (CDRs) and framework regions (FR) of a given antibody may be identified using systems known in the art, such as those described by Kabat et al. supra; Lefranc et al., supra and/or Honegger and Pluckthun, supra. For example, the numbering system described in Kabat et al. (1991, NIH Publication 91-3242, National Technical Information Service, Springfield, Va.) is well known to those in the art. Kabat et al. defined a numbering system for variable domain sequences that is applicable to any antibody. One of ordinary skill in the art can unambiguously assign this system of "Kabat numbering" to any variable domain amino acid sequence, without reliance on any experimental data beyond the sequence itself.

In certain embodiments, the present invention provides an anti-OX40 antibody comprising the CDRs of the heavy and light chain variable domains described in Table 1 (SEQ ID Nos: 1 to 212). For example, the invention provides an anti-OX40 antibody, or antigen-binding fragment thereof, comprising a heavy chain variable region having the CDRs described in an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201. In one embodiment, the invention provides an anti-OX40 antibody, or antigen-binding fragment thereof, comprising a light chain variable region having the CDRs described in an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the invention provides an anti-OX40 antibody, or antigen-binding fragment thereof, comprising a light chain variable region having the CDRs described in an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213; and a heavy chain variable region having the CDRs described in an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201.

In one embodiment, the present invention features an isolated human anti-human OX40 (hOX40) antibody, or an antigen-binding fragment thereof, comprising a heavy chain variable domain comprising a heavy chain CDR set (CDR1, CDR2, and CDR3) selected from the group consisting of SEQ ID Nos: 49, 50 and 51; SEQ ID Nos: 55, 56 and 57; SEQ ID Nos: 61, 62 and 63; SEQ ID Nos: 67, 68, and 69; SEQ ID Nos: 73, 74, and 75; SEQ ID Nos: 79, 80, and 81; SEQ ID Nos: 85, 86, and 87; SEQ ID Nos: 91, 92, and 93; SEQ ID Nos: 103, 104 and 105; SEQ ID Nos: 109, 110 and 111; SEQ ID Nos: 118, 119 and 120; SEQ ID Nos: 133, 134 and 135; SEQ ID Nos: 139, 140, 141; SEQ ID Nos: 148, 149 and 150; SEQ ID Nos: 157, 158 and 159; SEQ ID Nos: 163, 164 and 165; SEQ ID Nos: 172, 173 and 174; SEQ ID Nos: 178, 179 and 180; SEQ ID Nos: 184, 185 and 186; SEQ ID Nos. 195, 196 and 197; and SEQ ID Nos. 203, 204 and 205; and a light chain variable domain comprising a light chain CDR set (CDR1, CDR2, and CDR3) selected from the group consisting of SEQ ID Nos: 52, 53 and 54; SEQ ID Nos: 58, 59 and 60; SEQ ID Nos: 64, 65 and 66; SEQ ID Nos: 70, 71 and 72; SEQ ID Nos: 76, 77 and 78; SEQ ID Nos: 82, 83 and 84; SEQ ID Nos: 88, 89 and 90; SEQ ID Nos: 94, 95 and 96; SEQ ID Nos: 97, 98 and 99; SEQ ID Nos: 100, 101 and 102; SEQ ID Nos: 106, 107 and 108; SEQ ID Nos: 112, 113 and 114; SEQ ID Nos: 115, 116 and 117; SEQ ID Nos: 121, 122 and 123; SEQ ID Nos: 124, 125 and 126; SEQ ID Nos: 127, 128 and 129; SEQ ID Nos: 130, 131 and 132; SEQ ID Nos: 136, 137 and 138; SEQ ID Nos: 142, 143 and 144; SEQ ID Nos: 145, 146 and 147; SEQ ID Nos: 151, 152 and 153; SEQ ID Nos: 154, 155 and 156; SEQ ID Nos: 160, 161 and 162; SEQ ID Nos: 166, 167 and 168; SEQ ID Nos: 169, 170 and 171; SEQ ID Nos: 175, 176 and 177; SEQ ID Nos: 181, 182 and 183; SEQ ID Nos: 187, 188 and 189; SEQ ID Nos: 190, 191 and 192; SEQ ID Nos. 198, 199 and 200; SEQ ID Nos. 206, 207 and 208; SEQ ID Nos. 210, 211 and 212; and SEQ ID Nos. 214, 215 and 216.

In one embodiment, the antibody of the invention comprises a heavy chain CDR set/light chain CDR set selected from the group consisting of the heavy chain variable domain CDR set of SEQ ID Nos: 49, 50 and 51/the light chain variable domain CDR set of 52, 53 and 54; the heavy chain variable domain CDR set of SEQ ID Nos: 55, 56 and 57/the light chain variable domain CDR set of 58, 59 and 60; the heavy chain variable domain CDR set of SEQ ID Nos: 61, 62, and 63/the light chain variable domain CDR set of 64, 65 and 66; the heavy chain variable domain CDR set of SEQ ID Nos: 67, 68 and 69/the light chain variable domain CDR set of 70, 71 and 72; the heavy chain variable domain CDR set of SEQ ID Nos: 73, 74 and 75/the light chain variable domain CDR set of 76, 77 and 78; the heavy chain variable domain CDR set of SEQ ID Nos: 79, 80 and 81/the light chain variable domain CDR set of 82, 83 and 84; the heavy chain variable domain CDR set of SEQ ID Nos: 85, 86 and 87/the light chain variable domain CDR set of 88, 89 and 90; the heavy chain variable domain CDR set of SEQ ID Nos: 91, 92 and 93/the light chain variable domain CDR set of 94, 95 and 96; the heavy chain variable domain CDR set of SEQ ID Nos: 67, 68 and 69/the light chain variable domain CDR set of 97, 98 and 99; the heavy chain variable domain CDR set of SEQ ID Nos: 55, 56 and 57/the light chain variable domain CDR set of 100, 101 and 102; the heavy chain variable domain CDR set of SEQ ID Nos: 103, 104 and 105/the light chain variable domain CDR set of 106, 107 and 108; the heavy chain variable domain CDR set of SEQ ID Nos: 109, 110 and 111/the light chain variable domain CDR set of 112, 113 and 114; the heavy chain variable domain CDR set of SEQ ID Nos: 67, 68 and 69/the light chain variable domain CDR set of 115, 116 and 117; the heavy chain variable domain CDR set of SEQ ID Nos: 118, 119 and 120/the light chain variable domain CDR set of 121, 122 and 123; the heavy chain variable domain CDR set of SEQ ID Nos: 67, 68 and 69/the light chain variable domain CDR set of 124, 125 and 126; the heavy chain variable domain CDR set of SEQ ID Nos: 67, 68 and 69/the light chain variable domain CDR set of 127, 128 and 129; the heavy chain variable domain CDR set of SEQ ID Nos: 67, 68 and 69/the light chain variable domain CDR set of 130, 131 and 132; the heavy chain variable domain CDR set of SEQ ID Nos: 133, 134 and 135/the light chain variable domain CDR set of 136, 137 and 138; the heavy chain variable domain CDR set of SEQ ID Nos: 139, 140 and 141/the light chain variable domain CDR set of 142, 143 and 144; the heavy chain variable domain CDR set of SEQ ID Nos: 55, 56 and 57/the light chain variable domain CDR set of 145, 146 and 147; the heavy chain variable domain CDR set of SEQ ID Nos: 148, 149 and 150/the light chain variable domain CDR set of 151, 152 and 153; the heavy chain variable domain CDR set of SEQ ID Nos: 67, 68 and 69/the light chain variable domain CDR set of 154, 155 and 156; the heavy chain variable domain CDR set of SEQ ID Nos: 157, 158 and 159/the light chain variable domain CDR set of 160, 161 and 162; the heavy chain variable domain CDR set of SEQ ID Nos: 163, 164 and 165/the light chain variable domain CDR set of 166, 167 and 168; the heavy chain variable domain CDR set of SEQ ID Nos: 67, 68 and 69/the light chain variable domain CDR set of 169, 170, 171; the heavy chain variable domain CDR set of SEQ ID Nos: 172, 173 and 174/the light chain variable domain CDR set of 175, 176 and 177; the heavy chain variable domain CDR set of SEQ ID Nos: 178, 179 and 180/the light chain variable domain CDR set of 181, 182 and 183; the heavy chain variable domain CDR set of SEQ ID Nos: 184, 185 and 186/the light chain variable domain CDR set of 187, 188 and 189; the heavy chain variable domain CDR set of SEQ ID Nos: 67, 68 and 69/the light chain variable domain CDR set of 190, 191 and 192; the heavy chain variable domain CDR set of SEQ ID Nos: 195, 196 and 197/the light chain variable domain CDR set of 198, 199 and 200; the heavy chain variable domain CDR set of SEQ ID Nos: 203, 204 and 205/the light chain variable domain CDR set of 206, 207 and 208; the heavy chain variable domain CDR set of SEQ ID Nos: 61, 62 and 63/the light chain variable domain CDR set of 210, 211 and 212; and the heavy chain variable domain CDR set of SEQ ID Nos: 67, 68 and 69/the light chain variable domain CDR set of 214, 215 and 216.

In one embodiment, the invention provides an anti-OX40 antibody, or an antigen-binding fragment thereof, comprising a heavy chain comprising a CDR3 domain as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and comprising a variable domain comprising an amino acid sequence that has at least 95%, at least 96%, at least 97%, at least 98%, at least 99%, or at least 100% identity to a sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201. In one embodiment, the invention provides an anti-OX40 antibody, or an antigen-binding fragment thereof, comprising a light chain comprising a CDR3 domain as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213, and having a light chain variable domain comprising an amino acid sequence that has at least 95%, at least 96%, at least 97%, at least 98%, at least 99%, or at least 100% identity to a sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to OX40 and retains the functional characteristics, e.g., binding affinity and/or the ability to activate T cells, of the parent.

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference.

Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or an antigen binding fragment thereof, having the antigen binding regions of any of the antibodies described in Table 1.

In one embodiment, the present invention is directed to an antibody, or an antigen binding fragment thereof, having antigen binding regions of antibody OX1A11. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 2. In one embodiment, the invention is directed to an antibody having a heavy chain variable domain comprising the CDRs of SEQ ID NO: 1, and a light chain variable domain comprising the CDRs of SEQ ID NO: 2. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 2. In one embodiment, the invention features an anti-OX40 antibody, or an antigen-binding portion thereof, comprising a heavy chain variable region comprising a CDR3 domain comprising the amino acid as set forth in SEQ ID NO: 51, a CDR2 domain comprising the amino acid sequence as set forth in SEQ ID NO: 50, and a CDR1 domain comprising the amino acid sequence as set forth in SEQ ID NO: 49; and comprising a light chain variable region comprising a CDR3 domain comprising the amino acid as set forth in SEQ ID NO: 54, a CDR2 domain comprising the amino acid sequence as set forth in SEQ ID NO: 53, and a CDR1 domain comprising the amino acid sequence as set forth in SEQ ID NO: 52. The antibody may further be an IgG1 or an IgG4 isotype.

In one embodiment, the present invention is directed to an antibody, or an antigen binding fragment thereof, having antigen binding regions of antibody OX2E5. In one embodiment, the invention provides an antibody, or antigen-binding fragment thereof, comprising a heavy chain variable domain sequence as set forth in SEQ ID NO: 201, and a light chain variable domain sequence as set forth in SEQ ID NO: 202. In one embodiment, the invention is directed to an antibody having a heavy chain variable domain comprising the CDRs of SEQ ID NO: 201, and a light chain variable domain comprising the CDRs of SEQ ID NO: 202. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 201, and comprises a light chain variable region having an amino acid sequence that is at least 95% identical, at least 96% identical, at least 97% identical, at least 98% identical, or at least 99% identical to the sequence set forth in SEQ ID NO: 202. In one embodiment, the invention features an anti-OX40 antibody, or an antigen-binding portion thereof, comprising a heavy chain variable region comprising a CDR3 domain comprising the amino acid as set forth in SEQ ID NO: 205, a CDR2 domain comprising the amino acid sequence as set forth in SEQ ID NO: 204, and a CDR1 domain comprising the amino acid sequence as set forth in SEQ ID NO: 203; and comprising a light chain variable region comprising a CDR3 domain comprising the amino acid as set forth in SEQ ID NO: 208, a CDR2 domain comprising the amino acid sequence as set forth in SEQ ID NO: 207, and a CDR1 domain comprising the amino acid sequence as set forth in SEQ ID NO: 206. The antibody may further be an IgG1 or an IgG4 isotype.

In one embodiment, the present invention is directed to an antibody, or an antigen binding fragment thereof, having antigen binding regions of antibody OX2B12. In one embodiment, the invention provides an antibody, or antigen-binding fragment thereof, comprising a heavy chain variable domain sequence as set forth in SEQ ID NO: 21, and a light chain variable domain sequence as set forth in SEQ ID NO: 22. In one embodiment, the invention is directed to an antibody having a heavy chain variable domain comprising the CDRs of SEQ ID NO: 21, and a light chain variable domain comprising the CDRs of SEQ ID NO: 22. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 21, and comprises a light chain variable region having an amino acid sequence that is at least 95% identical, at least 96% identical, at least 97% identical, at least 98% identical, or at least 99% identical to the sequence set forth in SEQ ID NO: 22. In one embodiment, the invention features an anti-OX40 antibody, or an antigen-binding portion thereof, comprising a heavy chain variable region comprising a CDR3 domain comprising the amino acid as set forth in SEQ ID NO: 111, a CDR2 domain comprising the amino acid sequence as set forth in SEQ ID NO: 110, and a CDR1 domain comprising the amino acid sequence as set forth in SEQ ID NO: 109; and comprising a light chain variable region comprising a CDR3 domain comprising the amino acid as set forth in SEQ ID NO: 114, a CDR2 domain comprising the amino acid sequence as set forth in SEQ ID NO: 113, and a CDR1 domain comprising the amino acid sequence as set forth in SEQ ID NO: 112. The antibody may further be an IgG1 or an IgG4 isotype.

In one embodiment, the present invention is directed to an antibody, or an antigen binding fragment thereof, having antigen binding regions of antibody OX1B1. In one embodiment, the invention provides an antibody, or antigen-binding fragment thereof, comprising a heavy chain variable domain sequence as set forth in SEQ ID NO: 3, and a light chain variable domain sequence as set forth in SEQ ID NO: 4. In one embodiment, the invention is directed to an antibody having a heavy chain variable domain comprising the CDRs of SEQ ID NO: 3, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 3, and comprises a light chain variable region having an amino acid sequence that is at least 95% identical, at least 96% identical, at least 97% identical, at least 98% identical, or at least 99% identical to the sequence set forth in SEQ ID NO: 4. In one embodiment, the invention features an anti-OX40 antibody, or an antigen-binding portion thereof, comprising a heavy chain variable region comprising a CDR3 domain comprising the amino acid as set forth in SEQ ID NO: 57, a CDR2 domain comprising the amino acid sequence as set forth in SEQ ID NO: 56, and a CDR1 domain comprising the amino acid sequence as set forth in SEQ ID NO: 55; and comprising a light chain variable region comprising a CDR3 domain comprising the amino acid as set forth in SEQ ID NO: 60, a CDR2 domain comprising the amino acid sequence as set forth in SEQ ID NO: 59, and a CDR1 domain comprising the amino acid sequence as set forth in SEQ ID NO: 58. The antibody may further be an IgG1 or an IgG4 isotype.

In one embodiment, the present invention is directed to an antibody, or an antigen binding fragment thereof, having antigen binding regions of antibody OX5C1. In one embodiment, the invention provides an antibody, or antigen-binding fragment thereof, comprising a heavy chain variable domain sequence as set forth in SEQ ID NO: 46, and a light chain variable domain sequence as set forth in SEQ ID NO: 47. In one embodiment, the invention is directed to an antibody having a heavy chain variable domain comprising the CDRs of SEQ ID NO: 46, and a light chain variable domain comprising the CDRs of SEQ ID NO: 47. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 46, and comprises a light chain variable region having an amino acid sequence that is at least 95% identical, at least 96% identical, at least 97% identical, at least 98% identical, or at least 99% identical to the sequence set forth in SEQ ID NO: 47. In one embodiment, the invention features an anti-OX40 antibody, or an antigen-binding portion thereof, comprising a heavy chain variable region comprising a CDR3 domain comprising the amino acid as set forth in SEQ ID NO: 186, a CDR2 domain comprising the amino acid sequence as set forth in SEQ ID NO: 185, and a CDR1 domain comprising the amino acid sequence as set forth in SEQ ID NO: 184; and comprising a light chain variable region comprising a CDR3 domain comprising the amino acid as set forth in SEQ ID NO: 189, a CDR2 domain comprising the amino acid sequence as set forth in SEQ ID NO: 188, and a CDR1 domain comprising the amino acid sequence as set forth in SEQ ID NO: 187. The antibody may further be an IgG1 or an IgG4 isotype.

In one embodiment, the present invention is directed to an antibody, or an antigen binding fragment thereof, having antigen binding regions of antibody OX4D7. In one embodiment, the invention provides an antibody, or antigen-binding fragment thereof, comprising a heavy chain variable domain sequence as set forth in SEQ ID NO: 37, and a light chain variable domain sequence as set forth in SEQ ID NO: 38. In one embodiment, the invention is directed to an antibody having a heavy chain variable domain comprising the CDRs of SEQ ID NO: 37, and a light chain variable domain comprising the CDRs of SEQ ID NO: 38. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 37, and comprises a light chain variable region having an amino acid sequence that is at least 95% identical, at least 96% identical, at least 97% identical, at least 98% identical, or at least 99% identical to the sequence set forth in SEQ ID NO: 38. In one embodiment, the invention features an anti-OX40 antibody, or an antigen-binding portion thereof, comprising a heavy chain variable region comprising a CDR3 domain comprising the amino acid as set forth in SEQ ID NO: 159, a CDR2 domain comprising the amino acid sequence as set forth in SEQ ID NO: 158, and a CDR1 domain comprising the amino acid sequence as set forth in SEQ ID NO: 157; and comprising a light chain variable region comprising a CDR3 domain comprising the amino acid as set forth in SEQ ID NO: 162, a CDR2 domain comprising the amino acid sequence as set forth in SEQ ID NO: 161, and a CDR1 domain comprising the amino acid sequence as set forth in SEQ ID NO: 160. The antibody may further be an IgG1 or an IgG4 isotype.

In one embodiment, the present invention is directed to an antibody, or an antigen binding fragment thereof, having antigen binding regions of antibody OX5B9. In one embodiment, the invention provides an antibody, or antigen-binding fragment thereof, comprising a heavy chain variable domain sequence as set forth in SEQ ID NO: 44, and a light chain variable domain sequence as set forth in SEQ ID NO: 45. In one embodiment, the invention is directed to an antibody having a heavy chain variable domain comprising the CDRs of SEQ ID NO: 44, and a light chain variable domain comprising the CDRs of SEQ ID NO: 45. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 44, and comprises a light chain variable region having an amino acid sequence that is at least 95% identical, at least 96% identical, at least 97% identical, at least 98% identical, or at least 99% identical to the sequence set forth in SEQ ID NO: 45. In one embodiment, the invention features an anti-OX40 antibody, or an antigen-binding portion thereof, comprising a heavy chain variable region comprising a CDR3 domain comprising the amino acid as set forth in SEQ ID NO: 180, a CDR2 domain comprising the amino acid sequence as set forth in SEQ ID NO: 179, and a CDR1 domain comprising the amino acid sequence as set forth in SEQ ID NO: 178; and comprising a light chain variable region comprising a CDR3 domain comprising the amino acid as set forth in SEQ ID NO: 183, a CDR2 domain comprising the amino acid sequence as set forth in SEQ ID NO: 182, and a CDR1 domain comprising the amino acid sequence as set forth in SEQ ID NO: 181. The antibody may further be an IgG1 or an IgG4 isotype.

In one embodiment, the present invention is directed to an antibody, or an antigen binding fragment thereof, having antigen binding regions of antibody OX1C4. In one embodiment, the invention provides an antibody, or antigen-binding fragment thereof, comprising a heavy chain variable domain sequence as set forth in SEQ ID NO: 9, and a light chain variable domain sequence as set forth in SEQ ID NO: 10. In one embodiment, the invention is directed to an antibody having a heavy chain variable domain comprising the CDRs of SEQ ID NO: 9, and a light chain variable domain comprising the CDRs of SEQ ID NO: 10. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 9, and comprises a light chain variable region having an amino acid sequence that is at least 95% identical, at least 96% identical, at least 97% identical, at least 98% identical, or at least 99% identical to the sequence set forth in SEQ ID NO: 10. In one embodiment, the invention features an anti-OX40 antibody, or an antigen-binding portion thereof, comprising a heavy chain variable region comprising a CDR3 domain comprising the amino acid as set forth in SEQ ID NO: 75, a CDR2 domain comprising the amino acid sequence as set forth in SEQ ID NO: 74, and a CDR1 domain comprising the amino acid sequence as set forth in SEQ ID NO: 73; and comprising a light chain variable region comprising a CDR3 domain comprising the amino acid as set forth in SEQ ID NO: 78, a CDR2 domain comprising the amino acid sequence as set forth in SEQ ID NO: 77, and a CDR1 domain comprising the amino acid sequence as set forth in SEQ ID NO: 76. The antibody may further be an IgG1 or an IgG4 isotype.

In one embodiment, the present invention is directed to an antibody, or an antigen binding fragment thereof, having antigen binding regions of antibody OX4B5. In one embodiment, the invention provides an antibody, or antigen-binding fragment thereof, comprising a heavy chain variable domain sequence as set forth in SEQ ID NO: 193, and a light chain variable domain sequence as set forth in SEQ ID NO: 194. In one embodiment, the invention is directed to an antibody having a heavy chain variable domain comprising the CDRs of SEQ ID NO: 193, and a light chain variable domain comprising the CDRs of SEQ ID NO: 194. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 193, and comprises a light chain variable region having an amino acid sequence that is at least 95% identical, at least 96% identical, at least 97% identical, at least 98% identical, or at least 99% identical to the sequence set forth in SEQ ID NO: 194. In one embodiment, the invention features an anti-OX40 antibody, or an antigen-binding portion thereof, comprising a heavy chain variable region comprising a CDR3 domain comprising the amino acid as set forth in SEQ ID NO: 197, a CDR2 domain comprising the amino acid sequence as set forth in SEQ ID NO: 195, and a CDR1 domain comprising the amino acid sequence as set forth in SEQ ID NO: 195; and comprising a light chain variable region comprising a CDR3 domain comprising the amino acid as set forth in SEQ ID NO: 200, a CDR2 domain comprising the amino acid sequence as set forth in SEQ ID NO: 199, and a CDR1 domain comprising the amino acid sequence as set forth in SEQ ID NO: 198.

In one embodiment, the present invention is directed to an antibody, or an antigen binding fragment thereof, having antigen binding regions of antibody OX2B5. In one embodiment, the invention provides an antibody, or antigen-binding fragment thereof, comprising a heavy chain variable domain sequence as set forth in SEQ ID NO: 5, and a light chain variable domain sequence as set forth in SEQ ID NO: 209. In one embodiment, the invention is directed to an antibody having a heavy chain variable domain comprising the CDRs of SEQ ID NO: 5, and a light chain variable domain comprising the CDRs of SEQ ID NO: 209. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 5, and comprises a light chain variable region having an amino acid sequence that is at least 95% identical, at least 96% identical, at least 97% identical, at least 98% identical, or at least 99% identical to the sequence set forth in SEQ ID NO: 209. In one embodiment, the invention features an anti-OX40 antibody, or an antigen-binding portion thereof, comprising a heavy chain variable region comprising a CDR3 domain comprising the amino acid as set forth in SEQ ID NO: 63, a CDR2 domain comprising the amino acid sequence as set forth in SEQ ID NO: 62, and a CDR1 domain comprising the amino acid sequence as set forth in SEQ ID NO: 61; and comprising a light chain variable region comprising a CDR3 domain comprising the amino acid as set forth in SEQ ID NO: 212, a CDR2 domain comprising the amino acid sequence as set forth in SEQ ID NO: 211, and a CDR1 domain comprising the amino acid sequence as set forth in SEQ ID NO: 210.

In one embodiment, the present invention is directed to an antibody, or an antigen binding fragment thereof, having antigen binding regions of antibody OX2B4. In one embodiment, the invention provides an antibody, or antigen-binding fragment thereof, comprising a heavy chain variable domain sequence as set forth in SEQ ID NO: 24, and a light chain variable domain sequence as set forth in SEQ ID NO: 25. In one embodiment, the invention is directed to an antibody having a heavy chain variable domain comprising the CDRs of SEQ ID NO: 24, and a light chain variable domain comprising the CDRs of SEQ ID NO: 25. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 24, and comprises a light chain variable region having an amino acid sequence that is at least 95% identical, at least 96% identical, at least 97% identical, at least 98% identical, or at least 99% identical to the sequence set forth in SEQ ID NO: 25. In one embodiment, the invention features an anti-OX40 antibody, or an antigen-binding portion thereof, comprising a heavy chain variable region comprising a CDR3 domain comprising the amino acid as set forth in SEQ ID NO: 120, a CDR2 domain comprising the amino acid sequence as set forth in SEQ ID NO: 119, and a CDR1 domain comprising the amino acid sequence as set forth in SEQ ID NO: 118; and comprising a light chain variable region comprising a CDR3 domain comprising the amino acid as set forth in SEQ ID NO: 123, a CDR2 domain comprising the amino acid sequence as set forth in SEQ ID NO: 122, and a CDR1 domain comprising the amino acid sequence as set forth in SEQ ID NO: 121.

In one embodiment, the present invention is directed to an antibody, or an antigen binding fragment thereof, having antigen binding regions of antibody OX2B3. In one embodiment, the invention provides an antibody, or antigen-binding fragment thereof, comprising a heavy chain variable domain sequence as set forth in SEQ ID NO: 7, and a light chain variable domain sequence as set forth in SEQ ID NO: 23. In one embodiment, the invention is directed to an antibody having a heavy chain variable domain comprising the CDRs of SEQ ID NO: 7, and a light chain variable domain comprising the CDRs of SEQ ID NO: 23. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 7, and comprises a light chain variable region having an amino acid sequence that is at least 95% identical, at least 96% identical, at least 97% identical, at least 98% identical, or at least 99% identical to the sequence set forth in SEQ ID NO: 23. In one embodiment, the invention features an anti-OX40 antibody, or an antigen-binding portion thereof, comprising a heavy chain variable region comprising a CDR3 domain comprising the amino acid as set forth in SEQ ID NO: 69, a CDR2 domain comprising the amino acid sequence as set forth in SEQ ID NO: 68, and a CDR1 domain comprising the amino acid sequence as set forth in SEQ ID NO: 67; and comprising a light chain variable region comprising a CDR3 domain comprising the amino acid as set forth in SEQ ID NO: 117, a CDR2 domain comprising the amino acid sequence as set forth in SEQ ID NO: 116, and a CDR1 domain comprising the amino acid sequence as set forth in SEQ ID NO: 115.

The antibody of the invention may further be an IgG1 or an IgG4 isotype.

As described in Table 1, antibodies OX1B3, OX1E7, OX2B3, OX2B6, OX2F2, OX2G2, OX4D4, OX4G9, OX5D7 and OX5C11 have a heavy chain variable region having an amino acid sequence as set forth in SEQ ID NO. 7. As also described in Table 1, antibodies OX1B1, OX1F2 and OX4A12 have a heavy chain variable region having an amino acid sequence as set forth in SEQ ID NO. 3.

Antigen-binding fragments of antigen binding proteins of the invention may be produced by conventional techniques. Examples of such fragments include, but are not limited to, Fab and F(ab')2 fragments.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different VL and VH-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

In certain embodiments, the present disclosure provides a Fab fragment, having a variable domain region from a heavy chain and a variable domain region from a light chain, wherein the heavy chain variable domain sequence that is at least 95% identical, at least 96% identical, at least 97% identical, at least 98% identical, at least 99%, or 100% identical, to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and that has a light chain variable domain sequence that is at least 95% identical, at least 96% identical, at least 97% identical, at least 98% identical, at least 99%, or 100% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. Preferably, the human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 7/SEQ ID NO. 17, SEQ ID NO. 3/SEQ ID NO. 18, SEQ ID NO. 19/SEQ ID NO. 20, SEQ ID NO. 21/SEQ ID NO. 22, SEQ ID NO. 7/SEQ ID NO. 23, SEQ ID NO. 24/SEQ ID NO. 25, SEQ ID NO. 7/SEQ ID NO. 26, SEQ ID NO. 7/SEQ ID NO. 27, SEQ ID NO. 7/SEQ ID NO. 28, SEQ ID NO. 29/SEQ ID NO. 30, SEQ ID NO. 31/SEQ ID NO. 32, SEQ ID NO. 3/SEQ ID NO. 33, SEQ ID NO. 34/SEQ ID NO. 35, SEQ ID NO. 7/SEQ ID NO. 36, SEQ ID NO. 37/SEQ ID NO. 38, SEQ ID NO. 39/SEQ ID NO. 40, SEQ ID NO. 7/SEQ ID NO. 41, SEQ ID NO. 42/SEQ ID NO. 43), SEQ ID NO. 44/SEQ ID NO. 45, SEQ ID NO. 46/SEQ ID NO. 47 and SEQ ID NO. 7/SEQ ID NO. 48, SEQ ID NO. 193/SEQ ID NO. 194, SEQ ID NO. 201/SEQ ID NO. 202, SEQ ID NO. 5/SEQ ID NO. 209 and SEQ ID NO. 7/SEQ ID NO. 213.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, at least 99% identical, or 100% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and that has a light chain variable domain sequence that is at least 95% identical, at least 96% identical, at least 97% identical, at least 98% identical, at least 99%, or 100% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. Preferably, the human single chain antibody has both a heavy chain variable domain region and a light chain variable domain region, wherein the single chain human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 7/SEQ ID NO. 17, SEQ ID NO. 3/SEQ ID NO. 18, SEQ ID NO. 19/SEQ ID NO. 20, SEQ ID NO. 21/SEQ ID NO. 22, SEQ ID NO. 7/SEQ ID NO. 23, SEQ ID NO. 24/SEQ ID NO. 25, SEQ ID NO. 7/SEQ ID NO. 26, SEQ ID NO. 7/SEQ ID NO. 27, SEQ ID NO. 7/SEQ ID NO. 28, SEQ ID NO. 29/SEQ ID NO. 30, SEQ ID NO. 31/SEQ ID NO. 32, SEQ ID NO. 3/SEQ ID NO. 33, SEQ ID NO. 34/SEQ ID NO. 35, SEQ ID NO. 7/SEQ ID NO. 36, SEQ ID NO. 37/SEQ ID NO. 38, SEQ ID NO. 39/SEQ ID NO. 40, SEQ ID NO. 7/SEQ ID NO. 41, SEQ ID NO. 42/SEQ ID NO. 43), SEQ ID NO. 44/SEQ ID NO. 45, SEQ ID NO. 46/SEQ ID NO. 47 and SEQ ID NO. 7/SEQ ID NO. 48, SEQ ID NO. 193/SEQ ID NO. 194, SEQ ID NO. 201/SEQ ID NO. 202, SEQ ID NO. 5/SEQ ID NO. 209 and SEQ ID NO. 7/SEQ ID NO. 213.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, Methods Mol. Biol. 178:303-16). Moreover, if an IgG4 is desired, it may also be desired to introduce a point mutation (CPSCP→CPPCP) in the hinge region (Bloom et al., 1997, Protein Science 6:407) to alleviate a tendency to form intra-H chain disulfide bonds that can lead to heterogeneity in the IgG4 antibodies. Thus, in one embodiment, the antibody of the invention is a human IgG1 antibody. Thus, in one embodiment, the antibody of the invention is a human IgG4 antibody.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., Biochem. 32: 1180-1187 (1993); Kobayashi et al. Protein Eng. 12(10):879-884 (1999); and Burks et al. Proc. Natl. Acad. Sci. USA 94:412-417 (1997)). Near et al. Mol. Immunol. 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2).

In certain embodiments, an antibody, or antigen-binding fragment thereof, of the invention has a dissociation constant ($K_D$) of $1 \times 10^{-6}$ M or less; $5 \times 10^{-7}$ M or less; $1 \times 10^{-7}$ M or less; $5 \times 10^{-8}$ M or less; $1 \times 10^{-8}$ M or less; $5 \times 10^{-9}$ M or less; or $1 \times 10^{-9}$ M or less. In one embodiment, the antibody, or antigen-binding fragment thereof, of the invention as a $K_D$ from $1 \times 10^{-7}$ M to $1 \times 10^{-10}$ M. In one embodiment, the antibody, or antigen-binding fragment thereof, of the invention as a $K_D$ from $1 \times 10^{-8}$ M to $1 \times 10^{-10}$ M.

Those of ordinary skill in the art will appreciate standard methods known for determining the $K_D$ of an antibody, or fragment thereof. For example, in one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)).

According to another embodiment, $K_D$ is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.). Surface plasmon resonance can also be used to determine $K_{off}$ and $K_a$ values.

In particular embodiments, antigen binding proteins of the present invention have a binding affinity ($K_a$) for OX40 of at least $10^3$ $M^{-1}$ $S^{-1}$. In other embodiments, the antigen binding proteins exhibit a $K_a$ of at least $10^3$ $M^{-1}$ $S^{-1}$, at least $10^4$ $M^{-1}$ $S^{-1}$, at least $10^5$ $M^{-1}$ $S^{-1}$, or at least $10^6$ $M^{-1}$ $S^{-1}$. In other further embodiments, the antigen binding proteins exhibit a $K_a$ of at least $10^7$ $M^{-1}$ $S^{-1}$. In other further embodiments, the antigen binding proteins exhibit a $K_a$ of at least $10^7$ $M^{-1}$ $S^{-1}$ or at least $10^8$ $M^{-1}$ $S^{-1}$. In one embodiment, the anti-OX40 antibody, or fragment thereof, of the invention has a $K_a$ of at least $10^3$-$10^7$ $M^{-1}$ $S^{-1}$. In another embodiment, the antigen binding protein exhibits a $K_a$ substantially the same as that of an antibody described herein in the Examples. $K_a$ can be determined by Biacore testing, for example with Biacore 3000 or T200.

In another embodiment, the present disclosure provides an antigen binding protein that has a low dissociation rate from OX40. In one embodiment, the antigen binding protein has a $K_{off}$ of $1 \times 10^{-4}$ to $10^{-1}$ $sec^{-1}$ or lower. In another embodiment, the $K_{off}$ is $5 \times 10^{-5}$ to $10^{-1}$ $sec^{-1}$ or lower. In another embodiment, the $K_{off}$ is $5 \times 10^{-6}$ to $10^{-1}$ $sec^{-1}$ or lower. In another embodiment, the $K_{off}$ is substantially the same as an antibody described herein. In another embodiment, the antigen binding protein binds to OX40 with substantially the same $K_{off}$ as an antibody described herein.

In another aspect, the present disclosure provides an antigen binding protein that inhibits an activity of OX40. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of OX40 with substantially the same $IC_{50}$ as an antibody described herein.

In another aspect, the present disclosure provides an antigen binding protein that binds to OX40 expressed on the surface of a cell and, when so bound, inhibits OX40 signaling activity in the cell without causing a significant reduction in the amount of OX40 on the surface of the cell. Any method for determining or estimating the amount of OX40 on the surface and/or in the interior of the cell can be used. In other embodiments, binding of the antigen binding protein to the OX40-expressing cell causes less than about 75%, 50%, 40%, 30%, 20%, 15%, 10%, 5%, 1%, or 0.1% of the cell-surface OX40 to be internalized. In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of OX40, or to an epitope of OX40 and an epitope of another molecule, via two different antigen binding sites or regions. Moreover, bispecific antigen binding protein as disclosed herein can comprise a OX40 binding site from one of the herein-described antibodies and a second OX40 binding region from another of the herein-described antibodies, including those described herein by reference to other publications. Alternatively, a bispecific antigen binding protein may comprise an antigen binding site from one of the herein described antibodies and a second antigen binding site from another OX40 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, Nature 305:537, and chemical coupling of antibody fragments (Brennan et al., 1985, Science 229:81; Glennie et al., 1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Oligomers that contain one or more antigen binding proteins may be employed as OX40 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have OX40 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, Proc. Natl. Acad. Sci. USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, FEBS Letters 344:191. The use of a modified leucine zipper that allows for stable trimerization of a heterologous protein fused thereto is described in Fanslow et al., 1994, Semin. Immunol. 6:267-

78. In one approach, recombinant fusion proteins comprising an anti-OX40 antibody fragment or derivative fused to a leucine zipper peptide are expressed in suitable host cells, and the soluble oligomeric anti-OX40 antibody fragments or derivatives that form are recovered from the culture supernatant.

Antigen binding proteins directed against OX40 can be used, for example, in assays to detect the presence of OX40 polypeptides, either in vitro or in vivo. The antigen binding proteins also may be employed in purifying OX40 proteins by immunoaffinity chromatography. Blocking antigen binding proteins can be used in the methods disclosed herein. Such antigen binding proteins that function as OX40 antagonists may be employed in treating any OX40-induced condition, including but not limited to various cancers.

Antigen binding proteins may be employed in an in vitro procedure, or administered in vivo to inhibit OX40-induced biological activity. Disorders caused or exacerbated (directly or indirectly) by the proteolytic of OX40, examples of which are provided herein, thus may be treated. In one embodiment, the present invention provides a therapeutic method comprising in vivo administration of a OX40 blocking antigen binding protein to a mammal in need thereof in an amount effective for reducing a OX40-induced biological activity.

In certain embodiments of the invention, antigen binding proteins include human monoclonal antibodies that inhibit a biological activity of OX40.

Antigen binding proteins, including antibodies and antibody fragments described herein, may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides, including antibodies and antibody fragments described herein, of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of OX40 bound thereto. Polypeptides contemplated for use herein include substantially homogeneous recombinant mammalian anti-OX40 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-OX40 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Antibodies and fragments thereof of the present disclosure can be produced using any standard methods known in the art. In one example, the polypeptides are produced by recombinant DNA methods by inserting a nucleic acid sequence (a cDNA) encoding the polypeptide into a recombinant expression vector and expressing the DNA sequence under conditions promoting expression. The invention includes nucleic acids encoding any of the polypeptide sequences described in SEQ ID Nos: 1 to 216, as well as vectors comprising said nucleic acid sequences.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

OX40-binding polypeptides can also be produced by chemical synthesis (such as by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to OX40. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$—CH$_2$CH$_2$OH (1), where n is 20 to 2300 and X is H or a terminal modification, e.g., a $C_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life (t$_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half-life, such as the half-life of the protein in the serum or other bodily fluid of an animal.

Therapeutic Methods, Formulations and Modes of Administration

Any of the anti-OX40 antibodies or antigen binding fragments disclosed herein may be used in such therapeutic methods. Examples of anti-OX40 antibodies and antigen binding fragments that may be used in the therapeutic methods and compositions of the invention are described above.

In one embodiment, the anti-OX40 antibodies and antibody fragments of the invention are used to treat a disease requiring either stimulation of immune responses or suppression. OX40 stimulation (with agonists) is useful in treating a disease where the immune response (preferentially T cells) needs to be boosted. For example, in treating cancer. On the contrary OX40/OX40L blockade is useful in treating a disease in which inflammation needs to be reduced, for example during autoimmunity or allergy. OX40/OX40L blockade is usually done by using OX40L blocking antibodies.

In certain embodiments, the disease is selected from the group consisting of cancers, autoimmune diseases and infections.

In certain embodiments, anti-OX40 antibodies and antibody fragments of the invention may be used to treat cancer.

In other embodiments, anti-OX40 antibodies and antibody fragments of the invention may be used in treating infection (e.g., infection with a bacteria or virus or other pathogen). In some embodiments, the infection is with a virus and/or a bacteria. In some embodiments, the infection is with a pathogen.

In other embodiments, anti-OX40 antibodies and antibody fragments of the invention may be used to enhance immune function (e.g., by upregulating cell-mediated immune responses), e.g., in an individual having cancer.

The present disclosure further provides a method for treating a broad spectrum of mammalian cancers, infectious diseases, or autoimmune reactions, comprising administering an anti-OX40 polypeptide using the antibodies, and antibody fragments, disclosed herein. In one embodiment, the invention provides a method of treating cancer by administering an anti-human OX40 antibody to a subject in need thereof. Examples of antibodies, and fragments thereof, that may be used in the therapeutics methods disclosed herein include an anti-human OX40 human antibody of an IgG class having a binding affinity of at least $10^{-6}$M, or an anti-human OX40 Fab antibody fragment comprising a heavy chain variable region and a light chain variable region from the antibody sequences described in SEQ ID Nos. 1-48, 193, 194, 201, 202, 209 and 213 or comprising the CDRs described in any of the antibody sequences of SEQ ID Nos: 1-48, 193, 194, 201, 202, 209 and 213. In one embodiment, the methods disclosed herein comprise administering an isolated human antibody comprising a heavy chain variable domain sequence that is at least 95% identical, at least 96% identical, at least 97% identical, at least 98% identical, or at least 99% identical, to an amino acid sequence selected from the group consisting of heavy chain and a variable domain region from a light chain, wherein the heavy chain variable domain sequence that is at least 95% identical, at least 96% identical, at least 97% identical, at least 98% identical, at least 99%, or 100% identical, to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and having a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the methods disclosed herein comprise administering an IgG human anti-hOX40 antibody comprising a heavy chain variable domain sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and having a light chain variable domain sequence selected form the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In one embodiment, the methods described herein include the use of a Fab fragment comprising a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and comprising a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the methods described herein include the use of a human Fab antibody fragment comprising a heavy chain variable domain sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and comprising a light chain variable domain sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In one embodiment, the methods described herein include the use of a single chain human antibody, e.g., scFv, comprising a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and comprising a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213. In one embodiment, the methods described herein include the use of a single chain human antibody comprising a heavy chain variable domain having an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 19, SEQ ID NO. 21, SEQ ID NO. 24, SEQ ID NO. 29, SEQ ID NO. 31, SEQ ID NO. 34, SEQ ID NO. 37, SEQ ID NO. 39, SEQ ID NO. 42, SEQ ID NO. 44, SEQ ID NO. 46, SEQ ID NO. 193 and SEQ ID NO. 201, and comprising a light chain variable domain having an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 17, SEQ ID NO. 18, SEQ ID NO. 20, SEQ ID NO. 22, SEQ ID NO. 23, SEQ ID NO. 25, SEQ ID NO. 26, SEQ ID NO. 27, SEQ ID NO. 28, SEQ ID NO. 30, SEQ ID NO. 32, SEQ ID NO. 33, SEQ ID NO. 35, SEQ ID NO. 36, SEQ ID NO. 38, SEQ ID NO. 40, SEQ ID NO. 41, SEQ ID NO. 43, SEQ ID NO. 45, SEQ ID NO. 47, SEQ ID NO. 48, SEQ ID NO. 194, SEQ ID NO. 202, SEQ ID NO. 209 and SEQ ID NO. 213.

In one embodiment, the isolated anti-OX40 human antibody used in the methods of the invention comprises a heavy chain and a light chain wherein the antibody has a heavy chain/light chain variable domain sequence selected from the group consisting of SEQ ID NO. 1/SEQ ID NO. 2 (called OX1A11 herein), SEQ ID NO. 3/SEQ ID NO. 4 (called OX1B1 herein), SEQ ID NO. 5/SEQ ID NO. 6 (called OX1B2 herein), SEQ ID NO. 7/SEQ ID NO. 8 (called OX1B3 herein), SEQ ID NO. 9/SEQ ID NO. 10 (called OX1C4 herein), SEQ ID NO. 11/SEQ ID NO. 12 (called OX1C5 herein), SEQ ID NO. 13/SEQ ID NO. 14 (called OX1D9 herein), SEQ ID NO. 15/SEQ ID NO. 16 (called OX1E10 herein), SEQ ID NO. 7/SEQ ID NO. 17 (called OX1E7 herein), SEQ ID NO. 3/SEQ ID NO. 18 (called OX1F2 herein), SEQ ID NO. 19/SEQ ID NO. 20 (called OX1G9), SEQ ID NO. 21/SEQ ID NO. 22 (called OX2B12 herein), SEQ ID NO. 7/SEQ ID NO. 23 (called OX2B3 herein), SEQ ID NO. 24/SEQ ID NO. 25 (called OX2B4 herein), SEQ ID NO. 7/SEQ ID NO. 26 (called OX2B6 herein), SEQ ID NO. 7/SEQ ID NO. 27 (called OX2F2 herein), SEQ ID NO. 7/SEQ ID NO. 28 (called OX2G2 herein), SEQ ID NO. 29/SEQ ID NO. 30 (called OX3C10 herein), SEQ ID NO. 31/SEQ ID NO. 32 (called OX4A11 herein), SEQ ID NO. 3/SEQ ID NO. 33 (called OX4Al2 herein), SEQ ID NO. 34/SEQ ID NO. 35 (called OX4B6 herein), SEQ ID NO. 7/SEQ ID NO. 36 (called OX4D4 herein), SEQ ID NO. 37/SEQ ID NO. 38 (called OX4D7 herein), SEQ ID NO. 39/SEQ ID NO. 40 (called OX4D9 herein), SEQ ID NO. 7/SEQ ID NO. 41 (called OX4G9 herein), SEQ ID NO. 42/SEQ ID NO. 43 (called OX4H4 herein), SEQ ID NO. 44/SEQ ID NO. 45 (called OX5B9 herein), SEQ ID NO. 46/SEQ ID NO. 47 (called OX5C1 herein), SEQ ID NO. 7/SEQ ID NO. 48 (called OX5D7 herein), SEQ ID NO. 193/SEQ ID NO. 194 (called OX4B5 herein), SEQ ID NO. 201/SEQ ID NO. 202 (called OX2E5 herein), SEQ ID NO. 5/SEQ ID NO. 209 (called OX2B5 herein) and SEQ ID NO.7/SEQ ID NO. 213 (called OX5C11 herein).

In one embodiment, a Fab fragment used in the methods of the invention has both a heavy chain variable domain region and a light chain variable domain region wherein the antibody has a heavy chain/light chain variable domain sequence selected from the group consisting of SEQ ID NO. 1/SEQ ID NO. 2 (called OX1A11 herein), SEQ ID NO. 3/SEQ ID NO. 4 (called OX1B1 herein), SEQ ID NO. 5/SEQ ID NO. 6 (called OX1B2 herein), SEQ ID NO. 7/SEQ ID NO. 8 (called OX1B3 herein), SEQ ID NO. 9/SEQ ID NO. 10 (called OX1C4 herein), SEQ ID NO. 11/SEQ ID NO. 12 (called OX1C5 herein), SEQ ID NO. 13/SEQ ID NO. 14 (called OX1D9 herein), SEQ ID NO. 15/SEQ ID NO. 16 (called OX1E10 herein), SEQ ID NO. 7/SEQ ID NO. 17 (called OX1E7 herein), SEQ ID NO. 3/SEQ ID NO. 18 (called OX1F2 herein), SEQ ID NO. 19/SEQ ID NO. 20 (called OX1G9), SEQ ID NO. 21/SEQ ID NO. 22 (called OX2B12 herein), SEQ ID NO. 7/SEQ ID NO. 23 (called OX2B3 herein), SEQ ID NO. 24/SEQ ID NO. 25 (called OX2B4 herein), SEQ ID NO. 7/SEQ ID NO. 26 (called OX2B6 herein), SEQ ID NO. 7/SEQ ID NO. 27 (called OX2F2 herein), SEQ ID NO. 7/SEQ ID NO. 28 (called OX2G2 herein), SEQ ID NO. 29/SEQ ID NO. 30 (called OX3C10 herein), SEQ ID NO. 31/SEQ ID NO. 32 (called OX4A11 herein), SEQ ID NO. 3/SEQ ID NO. 33 (called OX4Al2 herein), SEQ ID NO. 34/SEQ ID NO. 35 (called OX4B6 herein), SEQ ID NO. 7/SEQ ID NO. 36 (called OX4D4 herein), SEQ ID NO. 37/SEQ ID NO. 38 (called OX4D7 herein), SEQ ID NO. 39/SEQ ID NO. 40 (called OX4D9 herein), SEQ ID NO. 7/SEQ ID NO. 41

(called OX4G9 herein), SEQ ID NO. 42/SEQ ID NO. 43 (called OX4H4 herein), SEQ ID NO. 44/SEQ ID NO. 45 (called OX5B9 herein), SEQ ID NO. 46/SEQ ID NO. 47 (called OX5C1 herein), SEQ ID NO. 7/SEQ ID NO. 48 (called OX5D7 herein), SEQ ID NO. 193/SEQ ID NO. 194 (called OX4B5 herein), SEQ ID NO. 201/SEQ ID NO. 202 (called OX2E5 herein), SEQ ID NO. 5/SEQ ID NO. 209 (called OX2B5 herein), and SEQ ID NO. 7/SEQ ID NO. 213 (called OX5C11 herein).

In one embodiment, a human single chain antibody has both a heavy chain variable domain region and a light chain variable domain region, wherein the single chain human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 7/SEQ ID NO. 17, SEQ ID NO. 3/SEQ ID NO. 18, SEQ ID NO. 19/SEQ ID NO. 20, SEQ ID NO. 21/SEQ ID NO. 22, SEQ ID NO. 7/SEQ ID NO. 23, SEQ ID NO. 24/SEQ ID NO. 25, SEQ ID NO. 7/SEQ ID NO. 26, SEQ ID NO. 7/SEQ ID NO. 27, SEQ ID NO. 7/SEQ ID NO. 28, SEQ ID NO. 29/SEQ ID NO. 30, SEQ ID NO. 31/SEQ ID NO. 32, SEQ ID NO. 3/SEQ ID NO. 33, SEQ ID NO. 34/SEQ ID NO. 35, SEQ ID NO. 7/SEQ ID NO. 36, SEQ ID NO. 37/SEQ ID NO. 38, SEQ ID NO. 39/SEQ ID NO. 40, SEQ ID NO. 7/SEQ ID NO. 41, SEQ ID NO. 42/SEQ ID NO. 43), SEQ ID NO. 44/SEQ ID NO. 45, SEQ ID NO. 46/SEQ ID NO. 47 and SEQ ID NO. 7/SEQ ID NO. 48, SEQ ID NO. 193/SEQ ID NO. 194, SEQ ID NO. 201/SEQ ID NO. 202, SEQ ID NO. 5/SEQ ID NO. 209 and SEQ ID NO. 7/SEQ ID NO. 213.

Cancer Indications

Anti-OX40 antibodies and antibody fragments of the invention may be used to treat a subject having cancer, including, for example, a solid tumor or leukemic cell that expresses OX40 on the cell surface.

In one embodiment, the OX40 antibodies and antibody fragments described herein are useful in treating, delaying the progression of, preventing relapse of or alleviating a symptom of a cancer or other neoplastic condition in a subject in need thereof.

In one embodiment, a cancer that may be treated using the antibodies and fragments of the invention, include, but are not limited to, prostate cancer, breast cancer, ovarian cancer, head and neck cancer, bladder cancer, melanoma, colorectal cancer, pancreatic cancer, lung cancer, leiomyoma, leiomyo sarcoma, glioma, glioblastoma, esophageal cancer, liver cancer, kidney cancer, stomach cancer, colon cancer, cervical cancer, uterine cancer, liver cancer and a hematological cancer.

As used herein, "hematological cancer" refers to a cancer of the blood, and includes leukemia, lymphoma and myeloma among others. "Leukemia" refers to a cancer of the blood in which too many white blood cells that are ineffective in fighting infection are made, thus crowding out the other parts that make up the blood, such as platelets and red blood cells. It is understood that cases of leukemia are classified as acute or chronic. "Lymphoma" refers to a group of blood cancers that develop in the lymphatic system. "Myeloma" refers to a cancer that forms in a type of white blood cell called a plasma cell.

Certain forms of leukemia that may be treated using the antibodies and fragments of the invention, include B chronic lymphocytic leukemia (B-CLL), B and T acute lymphocytic leukemia (ALL); acute myeloid leukemia (AML); chronic lymphocytic leukemia (CLL); chronic myelogenous leukemia (CML); hairy cell leukemia (HCL); Myeloproliferative disorder/neoplasm (MPDS); and myelodysplasia syndrome.

Certain forms of lymphoma that may be treated using the antibodies and fragments of the invention include B-cell lymphomas, including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; relapsed aggressive NHL, relapsed indolent NHL, refractory NHL, refractory indolent NHL, Burkitt's lymphoma, mantle cell lymphoma, AIDS-related lymphoma; and Waldenstrom's Macroglobulinemia, T cell lymphoma (TCL) and Hodgkin's Lymphoma (HL) among others.

Certain forms of myeloma that may be treated using the antibodies and fragments of the invention include multiple myeloma (MM), plasma cell myeloma, plamocytoma, giant cell myeloma, heavy-chain myeloma, and light chain or Bence-Jones myeloma.

Blockade of OX40 by antibodies can enhance an immune response against cancerous cells in the patient. An anti-OX40 antibody or antibody fragment disclosed herein can be used alone to inhibit the growth of cancerous tumors.

Alternatively, an anti-OX40 antibody or antibody fragment disclosed herein can be used in conjunction with other immunogenic agents, standard cancer treatments, or other antibodies. In one embodiment, the present disclosure provides a method of inhibiting growth of tumor cells in a subject, comprising administering to the subject a therapeutically effective amount of an anti-OX40 antibody, or antigen-binding fragment thereof. Preferably, the antibody or antibody fragment is a human anti-OX40 antibody or antibody fragment (such as any of the human anti-OX40 antibodies described herein).

In one embodiment, preferred cancers whose growth may be inhibited include cancers typically responsive to immunotherapy.

Optionally antibodies and antibody fragments to OX40 described herein can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas.

In certain embodiments, an anti-OX40 antibody or antibody fragment disclosed herein may be combined with a vaccination protocol. Many experimental strategies for vaccination against tumors have been devised. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. Many of these antigens can be shown to be the targets of tumor specific T cells found in the host. An anti-OX40 antibody or antibody fragment disclosed herein can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). (These somatic tissues may be protected from immune attack by various means). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with an anti-OX40 antibody or antibody fragment disclosed herein is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with OX40 blockade to activate more potent anti-tumor responses.

An anti-OX40 antibody or antibody fragment disclosed herein can also be combined with other cancer treatments. An anti-OX40 antibody or antibody fragment disclosed herein can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-OX40 antibody in combination with decarbazine for the treatment of melanoma. Another example of such a combination is an anti-OX40 antibody in combination with interleukin-2 (IL-2) for the treatment of melanoma. The scientific rationale behind the combined use of OX40 blockade and chemotherapy is that cell death, that is a consequence of the cytotoxic action of most chemotherapeutic compounds, should result in increased levels of tumor antigen in the antigen presentation pathway. Other combination therapies that may result in synergy with an anti-OX40 antibody or antibody fragment disclosed herein through cell death are radiation, surgery, and hormone deprivation. Each of these protocols creates a source of tumor antigen in the host. Angiogenesis inhibitors can also be combined with an anti-OX40 antibody or antibody fragment disclosed herein. Inhibition of angiogenesis often leads to tumor cell death which may feed tumor antigens into host antigen presentation pathways.

Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of an anti-OX40 antibody or antibody fragment disclosed herein. Alternatively, antigen may be delivered directly to DCs by the use of bispecific antibodies which bind to tumor antigen and a dendritic cell specific cell surface marker.

Bispecific antibodies can be used to target two separate tumor antigens. A variety of tumor targets may be considered, including, for example, Her2, cMet, EGFR and VEGFR expressing tumors. As such, in one embodiment, the invention provides a bispecific antibody comprising an anti-OX40 antibody (or antigen binding fragment) comprising a heavy and light chain variable region sequence as described herein or a heavy and light chain variable region comprising a set of CDR sequences as described herein and an anti-Her2, an anti-EGFR, an anti-VEGFR (see, for examples, antibodies described in U.S. Pat. No. 9,029,510, incorporated by reference herein), or an anti-cMet antibody (or antigen binding portion thereof). In one embodiment, the invention includes a bispecific antibody specific to OX40 and EGFR, wherein the antibody comprises an anti-OX40 antibody or fragment as disclosed herein and an anti-EGFR antibody or fragment as described in International Publication No. WO 2013/173255 or International Publication No. WO 2014/066530, both of which are incorporated by reference in their entireties herein. In one embodiment, the invention includes a bispecific antibody specific to OX40 and VEGFR, wherein the antibody comprises an anti-OX40 antibody or fragment as disclosed herein and an anti-VEGFR antibody or fragment as described in U.S. Pat. No. 9,029,510, incorporated by reference in its entirety herein. In one embodiment, the invention includes a bispecific antibody specific to OX40 and cMet, wherein the antibody comprises an anti-OX40 antibody or fragment as disclosed herein and an anti-cMet antibody or fragment as described in International Publication No. WO 2016/094455, incorporated by reference in its entirety herein.

Anti-OX40 antibodies or antibody fragments disclosed herein can also be used in combination with bispecific antibodies that target, for example, Fcα or Fcγ receptor-expressing effectors cells to tumor cells (U.S. Pat. Nos. 5,922,845 and 5,837,243).

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-OX40 antibodies and antibody fragments described herein to counteract the effects of the immunosuppressive agent and favor tumor immune responses by the host.

Other antibodies which activate host immune responsiveness can be used in combination with anti-OX40 antibodies and antibody fragments described herein. These include molecules on the surface of dendritic cells which activate DC function and antigen presentation. Anti-CD40 antibodies are able to substitute effectively for T cell helper activity (Ridge et al. (1998) Nature 393: 474-478) and can be used in conjunction with OX40 antibodies (Ito et al. (2000) *Immunobiology* 201 (5) 527-40). Activating antibodies to T cell costimulatory molecules such as CTLA-4, OX-40, 4-1BB, and ICOS may also provide for increased levels of T cell activation. OX40 blockade can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) Science 285: 546-51). These methods can also be used to activate T cell responses to infectious agents such as CMV. Ex vivo activation in the presence of anti-OX40 antibodies can increase the frequency and activity of the adoptively transferred T cells.

Additional methods for treating cancer using the anti-OX40 antibodies and fragments of the invention are disclosed below, for example, in the Combination Therapy section.

Infections

The present disclosure further provides a method of treating an infectious disease in a subject comprising administering to the subject an anti-OX40 antibody, or antigen-binding portion thereof, such that the subject is treated for the infectious disease. Preferably, the antibody is a human anti-human OX40 antibody or antibody fragment (such as any of the human anti-OX40 antibodies described herein).

In other embodiments, anti-OX40 antibodies and antibody fragments of the invention may be used in treating infection (e.g., infection with a bacteria or virus or other pathogen). In some embodiments, the infection is with a virus and/or a bacteria. In some embodiments, the infection is with a pathogen.

Some examples of pathogenic viruses causing infections treatable by the disclosed antibodies include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by the disclosed antibodies include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lymes disease bacteria.

Combination Therapy

In one embodiment, the anti-OX40 antibodies and antibody fragments of the invention can be administered alone or in combination with one or more additional therapies. Long-term therapy is equally possible as is adjuvant therapy in the context of other treatment strategies, as described above.

In some embodiments, the anti-OX40 antibodies and antibody fragments of the invention may be administered in conjunction with a chemotherapy or chemotherapeutic agent. In some embodiments, the anti-OX40 antibodies and antibody fragments of the invention may be administered in conjunction with a radiation therapy or radiotherapeutic agent. In some embodiments, the anti-OX40 antibodies and antibody fragments of the invention may be administered in conjunction with a targeted therapy or targeted therapeutic agent. In some embodiments, the anti-OX40 antibodies and antibody fragments of the invention may be administered in conjunction with an immunotherapy or immunotherapeutic agent, for example a monoclonal antibody.

In certain embodiments of such methods, one or more anti-OX40 antibodies and antibody fragments of the invention can be administered, together (simultaneously) or at different times (sequentially). In addition, anti-OX40 antibodies and antibody fragments of the invention can be administered with another type of compound(s) for treating cancer or for inhibiting angiogenesis.

The disclosed human anti-OX40 antibodies can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of the anti-OX40 antibodies and antibody fragments of the invention, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

OX40 is not constitutively expressed on naive T cells, but is induced after engagement of the T cell receptor (TCR). The ligand for OX40, OX40L, is predominantly expressed on antigen presenting cells. OX40 is highly expressed by activated CD4+ T cells, activated CD8+ T cells, memory T cells, and regulatory T cells. OX40 signaling can provide costimulatory signals to CD4 and CD8 T cells, leading to enhanced cell proliferation, survival, effector function and migration. OX40 signaling also enhances memory T cell development and function.

Accordingly, an anti-OX40 antibody or antibody fragment as described herein, may be co-administered with one or more additional antibodies that are effective in stimulating immune responses to thereby further enhance, stimulate or upregulate immune responses in a subject. For example, the invention provides a method for stimulating an immune response in a subject comprising administering to the subject an anti-OX40 antibody or antibody fragment and one or more additional immunostimulatory antibodies, such as an anti-PD-1 antibody, an anti-PD-L1 antibody and/or an anti-CTLA-4 antibody, such that an immune response is stimulated in the subject, for example to inhibit tumor growth or to stimulate an anti-viral response.

An important part of the immune system is its ability to distinguish between normal cells in the body and those it sees as "foreign." This lets the immune system attack the foreign cells while leaving the normal cells alone. To do this, it uses "checkpoints," which are molecules on certain immune cells that need to be activated (or inactivated) to start an immune response. Cancer cells sometimes find ways to use these checkpoints to avoid being attacked by the immune system. Accordingly, an immune checkpoint inhibitor includes a drug or agent, e.g., an antibody, that can activate T cells which are inactive in the absence of the drug or agent due, at least in part, to signaling from a cancer cell which can maintain the inactive state of the T cell.

Thus, in one embodiment, an anti-OX40 antibody or antigen binding antibody fragment of the invention is used in combination with an immune checkpoint inhibitor for the treatment of cancer. For example, in one embodiment, an anti-OX40 antibody, or antigen binding fragment, described herein is administered in combination with an antibody which is an immune checkpoint inhibitor, including, but not limited to, an anti-cytotoxic T-lymphocyte antigen 4 (CTLA-4) antibody, an anti-programmed death 1 (PD-1) antibody, or an anti-programmed death-ligand 1 (PD-L1) antibody. In one embodiment, an anti-OX40 antibody, or antigen binding fragment, described herein is administered in combination with trastuzumab (Herceptin).

In one embodiment, the subject is administered an anti-OX40 antibody or antibody fragment and an anti-PD-1 antibody. In one embodiment, the subject is administered an anti-OX40 antibody or antibody fragment selected from 1A11, 2E5, 2B12, 1B1, 5C1, 4D7, 5B9, 1C4, 4B5, and an anti-PD-1 antibody.

In another embodiment, the subject is administered an anti-OX40 antibody or antibody fragment and an anti-PD-L1 antibody. In one embodiment, the subject is administered an anti-OX40 antibody or antibody fragment selected from 1A11, 2E5, 2B12, 1B1, 5C1, 4D7, 5B9, 1C4, 4B5, and an anti-PD-L1 antibody.

In yet another embodiment, the subject is administered an anti-OX40 antibody or antibody fragment and an anti-CTLA-4 antibody. In one embodiment, the subject is administered an anti-OX40 antibody or antibody fragment selected from 1A11, 2E5, 2B12, 1B1, 5C1, 4D7, 5B9, 1C4, 4B5, and an anti-CTLA-4 antibody.

In one embodiment, the invention provides a method for treating a hyperproliferative disease (e.g., cancer), comprising administering a OX40 antibody and a CTLA-4 antibody to a subject. In further embodiments, the anti-OX40 antibody is administered at a subtherapeutic dose, the anti-CTLA-4 antibody is administered at a subtherapeutic dose, or both are administered at a subtherapeutic dose. Alternatively, a method for altering an adverse event associated with treatment of a hyperproliferative disease with an immunostimulatory agent, comprising administering an anti-OX40 antibody and a subtherapeutic dose of anti-CTLA-4 antibody to a subject.

In one embodiment, an anti-OX40 antibody, or antigen binding fragment (e.g. 1A11, 2E5, 2B12, 1B1, 5C1, 4D7, 5B9, 1C4, 4B5), described herein is administered in combination with an anti-cytotoxic T-lymphocyte antigen 4 (CTLA-4) antibody, for example ipilimumab (YERVOY) or tremelimumab (CP-675,206; MedImmune).

Another combination comprises administering a OX40 antibody or antibody fragment (e.g. 1A11, 2E5, 2B12, 1B1, 5C1, 4D7, 5B9, 1C4, 4B5) and a PD-1 or PD-L1 antibody to a subject. In one embodiment, an anti-OX40 antibody, or antigen binding fragment, described herein is administered in combination with an anti-programmed death 1 (PD-1) antibody, for example pembrolizumab (KEYTRUDA) or nivolumab (OPDIVO). In one embodiment, an anti-OX40 antibody, or antigen binding fragment, described herein (e.g. 1A11, 2E5, 2B12, 1B1, 5C1, 4D7, 5B9, 1C4, 4B5) is administered in combination with an anti-programmed death-ligand 1 (PD-L1) antibody, for example avelumab (MSB0010718C), atezolizumab (TECENTRIQ) or durvalumab (MEDI4736). In further embodiments, the anti-OX40 antibody is administered at a subtherapeutic dose, the anti-PD-1 or PD-L1 antibody is administered at a subtherapeutic dose, or both are administered at a subtherapeutic dose.

In one embodiment, an anti-OX40 antibody, or antigen binding fragment (e.g. 1A11, 2E5, 2B12, 1B1, 5C1, 4D7, 5B9, 1C4, 4B5), described herein is administered in conjunction with a PARP inhibitor (e.g., Olaparanib, Rucaparib, Niraparib, Cediranib, BMN673, Veliparib), Trabectedin, nab-paclitaxel (albumen-bound paclitaxel, ABRAXANE), Trebananib, Pazopanib, Cediranib, Palbociclib, everolimus, fluoropyrimidine (e.g., FOLFOX, FOLFIRI), IFL, regorafenib, Reolysin, Alimta, Zykadia, Sutent, Torisel (temsirolimus), Inlyta (axitinib, Pfizer), Afinitor (everolimus, Novartis), Nexavar (sorafenib, Onyx/Bayer), Votrient, Pazopanib, axitinib, IMA-901, AGS-003, cabozantinib, Vinflunine, Hsp90 inhibitor (e.g., apatorsin), Ad-GM-CSF (CT-0070), Temazolomide, IL-2, IFNa, vinblastine, Thalomid, dacarbazine, cyclophosphamide, lenalidomide, azacytidine, lenalidomide, bortezomid (VELCADE), amrubicine, carfilzomib, pralatrexate, and/or enzastaurin.

In one embodiment, an anti-OX40 antibody, or antigen binding fragment (e.g. 1A11, 2E5, 2B12, 1B1, 5C1, 4D7, 5B9, 1C4, 4B5), described herein is administered in conjunction with an agonist directed against an activating co-stimulatory molecule. In some embodiments, an activating co-stimulatory molecule may include CD40, CD226, CD28, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, an anti-human OX40 agonist antibody may be administered in conjunction with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3 (e.g., LAG-3-IgG fusion protein (IMP321)), B7-H3, B7-H4, IDO, TIGIT, MICA/B, or arginase.

In one embodiment, an anti-OX40 antibody, or antigen binding fragment (e.g. 1A11, 2E5, 2B12, 1B1, 5C1, 4D7, 5B9, 1C4, 4B5), described herein is administered in conjunction with an antagonist directed against CD19. In some embodiments, an anti-OX40 antibody, or antigen binding fragment (e.g. 1A11, 2E5, 2B12, 1B1, 5C1, 4D7, 5B9, 1C4, 4B5), described herein is administered in conjunction with MOR00208. In some embodiments, an anti-OX40 antibody, or antigen binding fragment (e.g. 1A11, 2E5, 2B12, 1B1, 5C1, 4D7, 5B9, 1C4, 4B5), described herein is administered in conjunction with an antagonist directed against CD38.

In one embodiment, an anti-OX40 antibody, or antigen binding fragment (e.g. 1A11, 2E5, 2B12, 1B1, 5C1, 4D7, 5B9, 1C4, 4B5), described herein is administered in conjunction with an angiogenesis inhibitor (e.g. bevacizumab, sorafenib, sunitinib, pazopanib) and everolimus.

Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-OX40 antibodies.

Therapeutic Methods and Compositions

Suitable routes of administering the antibody compositions described herein (e.g., human monoclonal antibodies, multispecific and bispecific molecules and immunoconjugates) are in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

Techniques and dosages for administration vary depending on the type of specific binding protein and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions comprising the antigen binding proteins of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

Thus, an anti-OX40 antibody, or antigen binding portion thereof, of the invention can be incorporated into a pharmaceutical composition suitable for parenteral administration. Preferably, the anti-OX40 antibody, or antigen binding portion thereof, will be prepared as an injectable solution containing 0.1-250 mg/ml antibody. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, an anti-OX40 antibody, or antigen binding portion thereof, described herein is administered by intravenous infusion or injection. In another preferred embodiment, an anti-OX40 antibody, or antigen binding portion thereof, is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The anti-OX40 antibody, or antigen binding portion thereof, of the present invention can be administered by a variety of methods known in the art, although for many therapeutic applications, the preferred route/mode of administration is subcutaneous injection, intravenous injection, or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., (Marcel Dekker, Inc., New York, 1978).

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

In certain embodiments, the disclosed antibodies are administered by inhalation, but aerosolization of full IgG antibodies may prove limiting due to their molecular size (~150 kDa). To maximize available commercial aerosolization devices, smaller Fab fragments may be required.

In certain embodiments, the subject anti-OX40 antibodies or antibody fragments of the invention can be used alone.

Diagnostics and Kits

In certain embodiments, any of the anti-OX40 antibodies provided herein is useful for detecting the presence of OX40 in a biological sample. In certain embodiments, a biological sample comprises a cell or tissue, such as a sample of a tumor (e.g., NSCLC or breast tumor).

In one embodiment, an anti-OX40 antibody for use in a method of diagnosis or detection is provided. In a further aspect, a method of detecting the presence of OX40 in a biological sample is provided. In certain embodiments, the method comprises contacting the biological sample with an anti-OX40 antibody as described herein under conditions permissive for binding of the anti-OX40 antibody to OX40, and detecting whether a complex is formed between the anti-OX40 antibody and OX40. Such method may be an in vitro or in vivo method. In one embodiment, an anti-OX40 antibody is used to select subjects eligible for therapy with an anti-OX40 antibody, e.g. where OX40 is a biomarker for selection of patients.

Exemplary disorders that may be diagnosed using an antibody of the invention include cancer.

In certain embodiments, the binding polypeptides of fragments thereof can be labeled or unlabeled for diagnostic purposes. Typically, diagnostic assays entail detecting the formation of a complex resulting from the binding of a binding polypeptide to OX40. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present disclosure can be utilized in enzyme immunoassays, wherein the subject polypeptides are conjugated to an enzyme. When a biological sample comprising an OX40 protein is combined with the subject binding polypeptides, binding occurs between the binding polypeptides and the OX40 protein. In one embodiment, a sample containing cells expressing an OX40 protein (e.g., endothelial cells) is combined with the subject antibodies, and binding occurs between the binding polypeptides and cells bearing an OX40 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of an OX40 protein in a biological sample using the antibodies or fragments thereof of the invention can also be prepared. Such kits will include an OX40 binding polypeptide, e.g., antibodies or fragments thereof, which binds to an OX40 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Other embodiments are described in the following non-limiting Examples.

Example 1

Experiments were performed to determine the binding capability of various anti-OX40 antibodies. Clones from the anti-OX40 antibody library were tested for binding on anti-CD3/anti-CD28 pre-activated human peripheral blood mononuclear cell (PBMC) for 3 days. Each clone was incubated at 5 μg/ml with $3\times10^5$ pre-activated human PBMCs. The binding of anti-OX40 antibodies to activated human T cells was revealed by flow cytometry using an APC-labelled anti-human Fc secondary antibody. A phycoerythrin (PE)-labelled anti-hCD3 antibody was also used to show that the fluorescence was detected on the T-cells. Secondary antibody alone was used as a negative control. A commercially available APC-labelled anti-human OX40 (clone Ber-ACT35) was used as positive control. The results are shown in FIG. 1. FIG. 1 shows the binding of anti-OX40 antibody clones on activated human T-cells measured by the percent CD3+OX40+ T cells. The anti-OX40 clones that were tested are shown on the x-axis. FIG. 1 shows that most of the tested anti-OX40 clones are bound on T cells.

Example 2

Experiments were performed to identify OX40 antibody clones with the ability to activate the NFkB signaling pathway. $OX40^+$ HEK293-NFkB-luciferase reporter stable cells were counted and re-suspended in RPMI-1640+5% FCS (complete medium). $6.7\times10^4$ cells/well (in 60 μl) were distributed in a white flat-bottom 96-well microplate. The cells were seeded in triplicate. Cells were stimulated by adding 60 μl of one of the following reagents: (1) Soluble TNFα (Biolegend; Ref. 570102; Lot. B204173) as a positive control; (2) Soluble anti-Histidine (Biolegend; Ref. 652502)

at 5 µg/ml+purified rhOX40L (Biolegend; Ref. 555704 or R&D systems; Ref. 1054-OX-010) at 1 µg/ml as a positive control; (3) Polyclonal anti-OX40 antibody, used to determine whether a mixture of antibodies recognizing various epitopes on the cognate antigen will be better agonists than the monoclonal antibodies; (4) Isotype Control FeH3 antibody at 20 µg/ml; (5) Anti-OX40 antibody clones at 20 µg/ml. Cells were then incubated at 37° C. in 5% $CO_2$.

After ~6 h stimulation the luciferase activity was revealed by the addition of 100 µl/well of BIO-GLO Luciferase Assay system from Promega (Cat. No. G7941; Lot. 0000168497). The plate was then incubated at room temperature in the dark for 5 min under slow shaking conditions. Luciferase activity was obtained by reading with the FlexStation3 from Molecular Devices (luminescence reading, 500 ms). Results are shown as relative light units (RLUs).

Figure 2A:
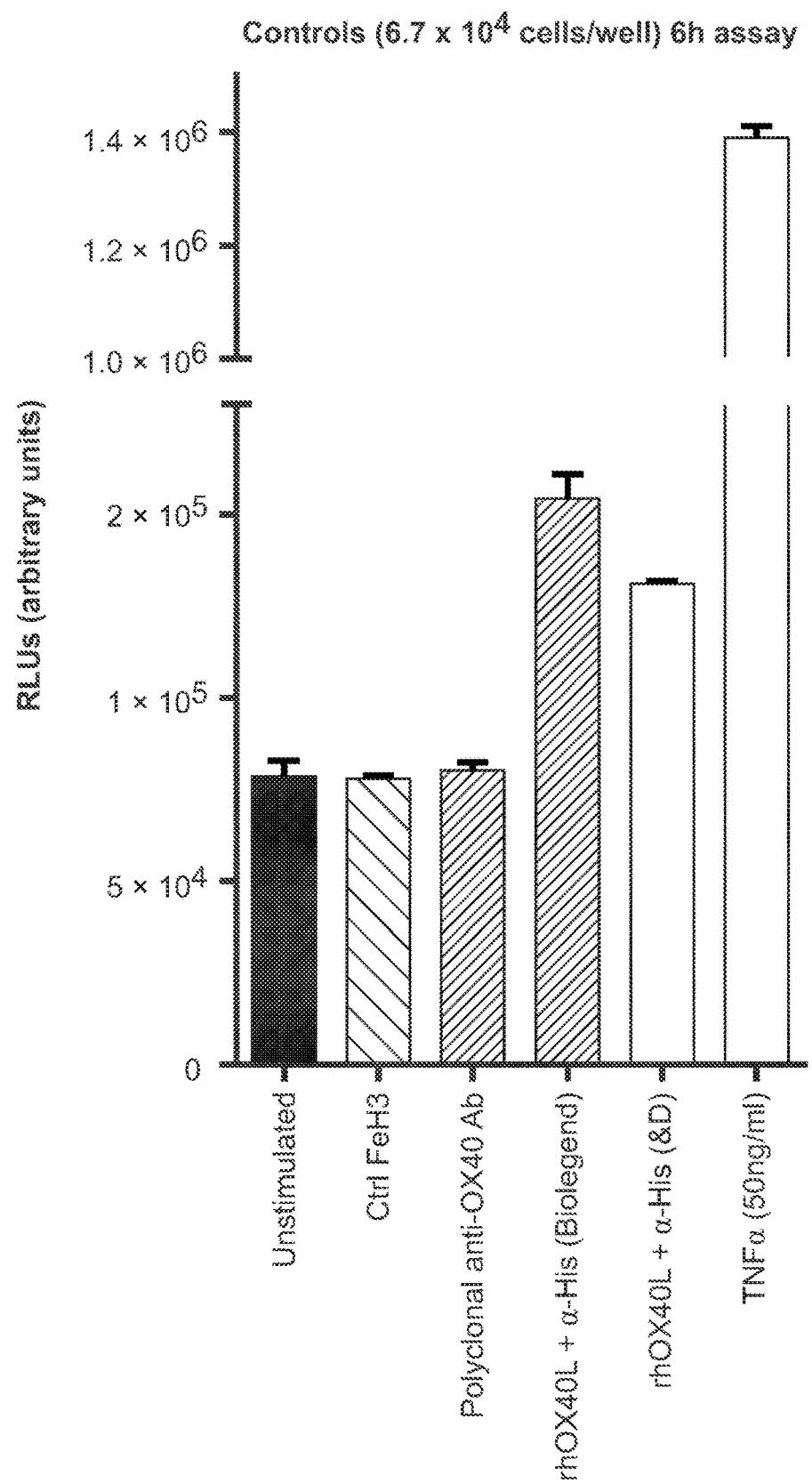
FIG. 2A is a graph that shows the luciferase activity measured by relative light units (RLUs) for the control experimental conditions after 6 hours of stimulation.
Figure 2B:
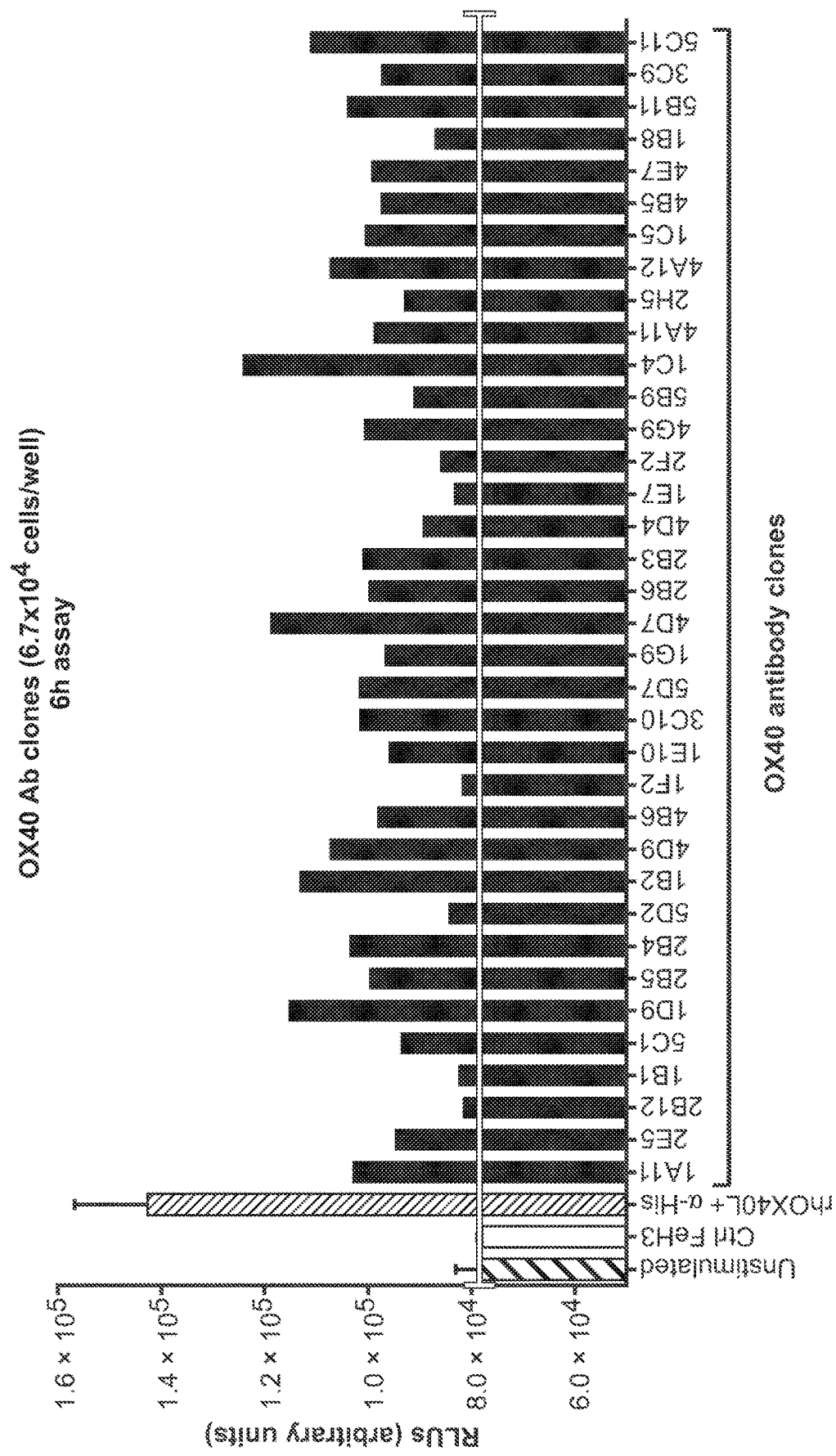
FIG. 2B is a graph that shows luciferase activity measured by RLUs for the anti-OX40 antibody clones tested after 6 hours of stimulation. Unstimulated cells and isotype control FeH3 antibody (Ctrl FeH3) are shown as negative controls. Soluble anti-Histidine+purified rhOX40L (rhOX40L+αHis) is shown as a positive control. The line bisecting the graph shows the negative control RLU levels as a reference.

FIG. 2A shows the luciferase activity measured by RLUs for the control experimental conditions after 6 hours of stimulation. As shown in FIG. 2A, unstimulated cells, isotype control FeH3 antibody (Ctrl FeH3) and polyclonal anti-OX40 antibody did not show an increase in RLUs, indicating that the NFkB pathway was not activated. The positive controls, soluble anti-Histidine+purified rhOX40L (rhOX40L+αHis) and soluble TNFα, showed higher RLUs, indicating an increase in NFkB activity, as expected. FIG. 2B shows luciferase activity measured by RLUs for the anti-OX40 antibody clones tested after 6 hours of stimulation. Unstimulated cells and isotype control FeH3 antibody (Ctrl FeH3) are shown as negative controls. Soluble anti-Histidine+purified rhOX40L (rhOX40L+αHis) is shown as a positive control. As shown in FIG. 2B, all of the OX40 clones showed an increase in RFUs over the negative control values. These results demonstrate that the OX40/HEK293-NFkB-Luc reporter assay worked properly based on internal controls. Clones 1C4, 4D7 1D9 and 1B2 showed the strongest NFkB activation (>50% of signal observed with purified rhOX40L+anti-His).

A similar set of experiments was carried out, where the stimulation time of the cells with the various reagents was increased from 6 hours to 15 hours. Similar to the first set of experiments, OX40+ HEK293-NFkB-luciferase reporter stable cells were counted and resuspended in RPMI-1640+ 5% FCS (complete medium). $5 \times 10^4$ cells/well (in 600) were distributed in a white flat-bottom 96-well plate. The cells were seeded in triplicate. Cells were stimulated by adding 60 µl of one of the following reagents: (1) Soluble TNFα (biolegend; Ref. 570102; Lot. B204173) as a positive control; (2) Soluble anti-Histidine (Biolegend; Ref. 652502) at 5 µg/ml+purified rhOX40L (Biolegend; Ref. 555704) at 1 µg/ml as a positive control; (3) Isotype Control FeH3 antibody at 20 µg/ml; (4) Anti-OX40 antibody clones at 20 µg/ml. Cells were then incubated at 37° C. in 5% $CO_2$.

After ~15 h stimulation the luciferase activity was reveal by adding 100 µl/well of BIOGLO Luciferase Assay system from Promega (Cat. No. G7941; Lot. 0000168497). The plate was incubated at room temperature in the dark for 5 min under slow shaking conditions. Luciferase activity was obtained by reading with the FlexStation3 from Molecular Devices (luminescence reading, 500 ms). Results are shown as relative light units (RLUs).

Figure 3A:
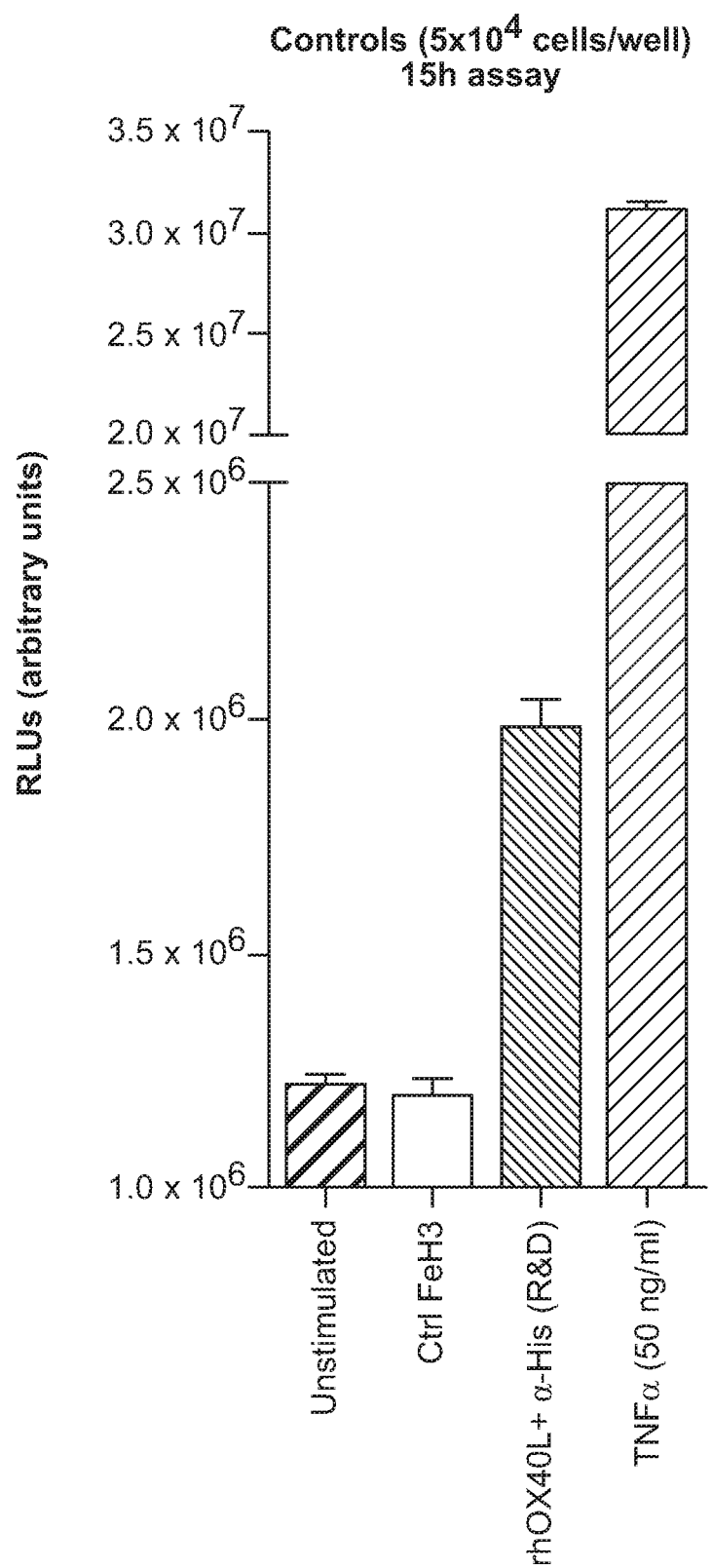
FIG. 3A is a graph that shows the luciferase activity measured by relative light units (RLUs) for the control experimental conditions after ~15 hours of stimulation.
Figure 3B:
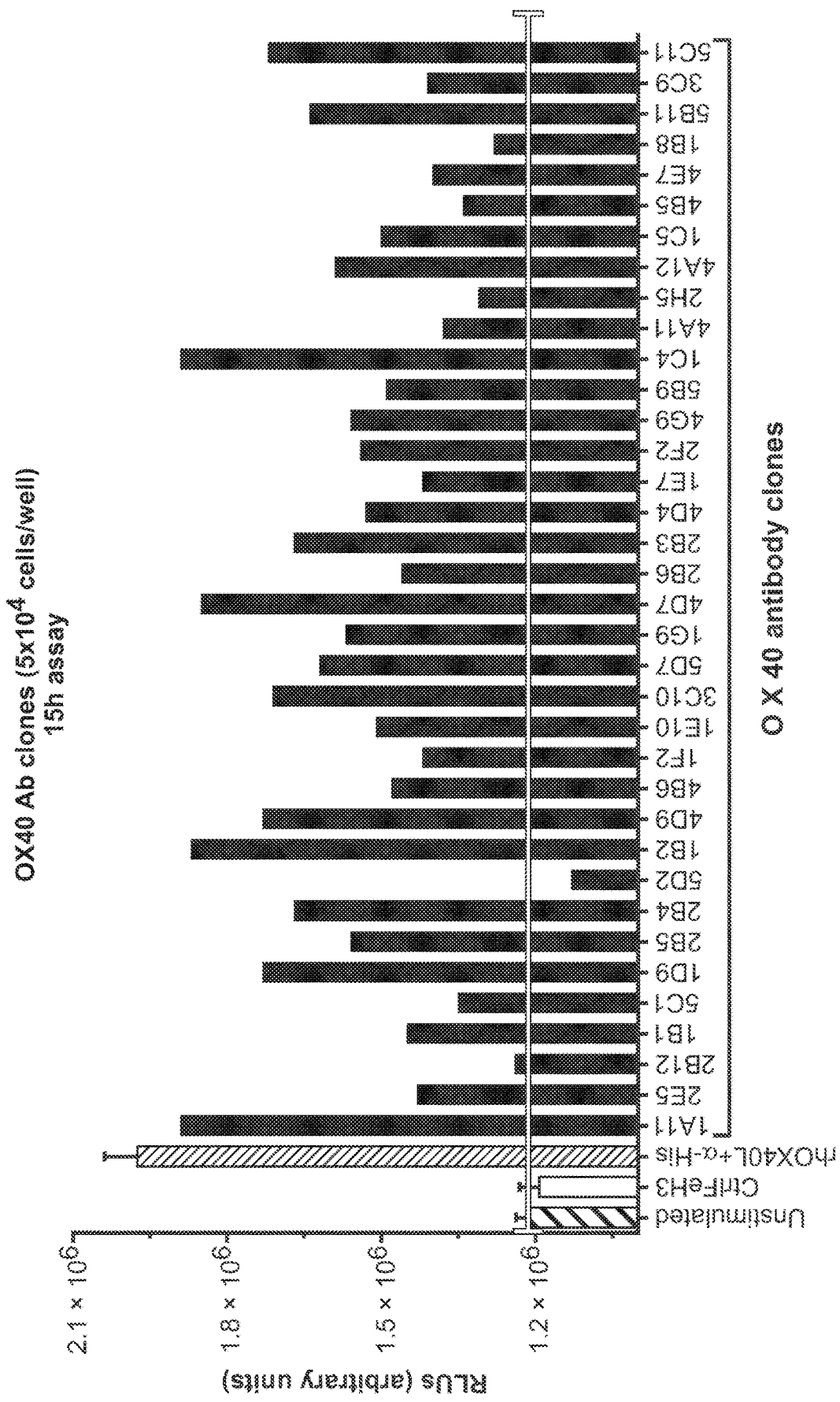
FIG. 3B is a graph that shows luciferase activity measured by RLUs for the anti-OX40 antibody clones tested after ~15 hours of stimulation. Unstimulated cells and isotype control FeH3 antibody (Ctrl FeH3) are shown as negative controls. Soluble anti-Histidine+purified rhOX40L (rhOX40L+αHis) is shown as a positive control. The line bisecting the graph shows the negative control RLU levels as a reference.

FIG. 3A shows the luciferase activity measured by RLUs for the control experimental conditions after ~15 hours of stimulation. As shown in FIG. 3A, unstimulated cells, isotype control FeH3 antibody (Ctrl FeH3) and polyclonal anti-OX40 antibody did not show an increase in RLUs, indicating that the NFkB pathway was not activated. The positive controls, soluble anti-Histidine+purified rhOX40L (rhOX40L+αHis) and soluble TNFα, showed higher RLUs, indicating an increase in NFkB activity, as expected. FIG. 3B shows luciferase activity measured by RLUs for the anti-OX40 antibody clones tested after ~15 hours of stimulation. Unstimulated cells and isotype control FeH3 antibody (Ctrl FeH3) are shown as negative controls. Soluble anti-Histidine+purified rhOX40L (rhOX40L+αHis) is shown as a positive control. As shown in FIG. 3B, all of the OX40 clones showed an increase in RFUs over the negative control values. These results demonstrate that the OX40/HEK293-NFkB-Luc reporter assay worked properly based on internal controls. A prolonged incubation time (15 h instead of 6 h) induced a stronger NFkB activity, suggesting that some clones take longer than 6 hours to stimulate NFkB activity. In particular clones 1A11, 1C4, 4D7, 1D9, 5C11, 2B4, 4D9, 3C10 and 1B2 were among the most active.

Example 3

A human T cell activation assay was used to identify OX40 clones with agonistic activity. A flat-bottom 96-well plate was coated with anti-CD3 (clone OKT3) at 1.5 µg/ml+ (anti-CD28 or anti-OX40 or anti-CD137 clones) at 10 µg/ml (100 µl/well final) in PBS 1×, overnight at 4° C. Anti-CD3 alone and FeD2, an isotype control antibody, were used as negative controls. Anti-CD28 was used as a positive control. The next day, the plate was washed three times with 150 µl of sterile complete medium per well (RPMI1640+10% FCS+Pen/Strep) under a sterile hood. Purified human T cells were plated at $4 \times 10^5$ cells/well in complete medium. The plate was incubated at 37° C. for 3 days in a humidified tissue culture incubator.

Figure 4A:
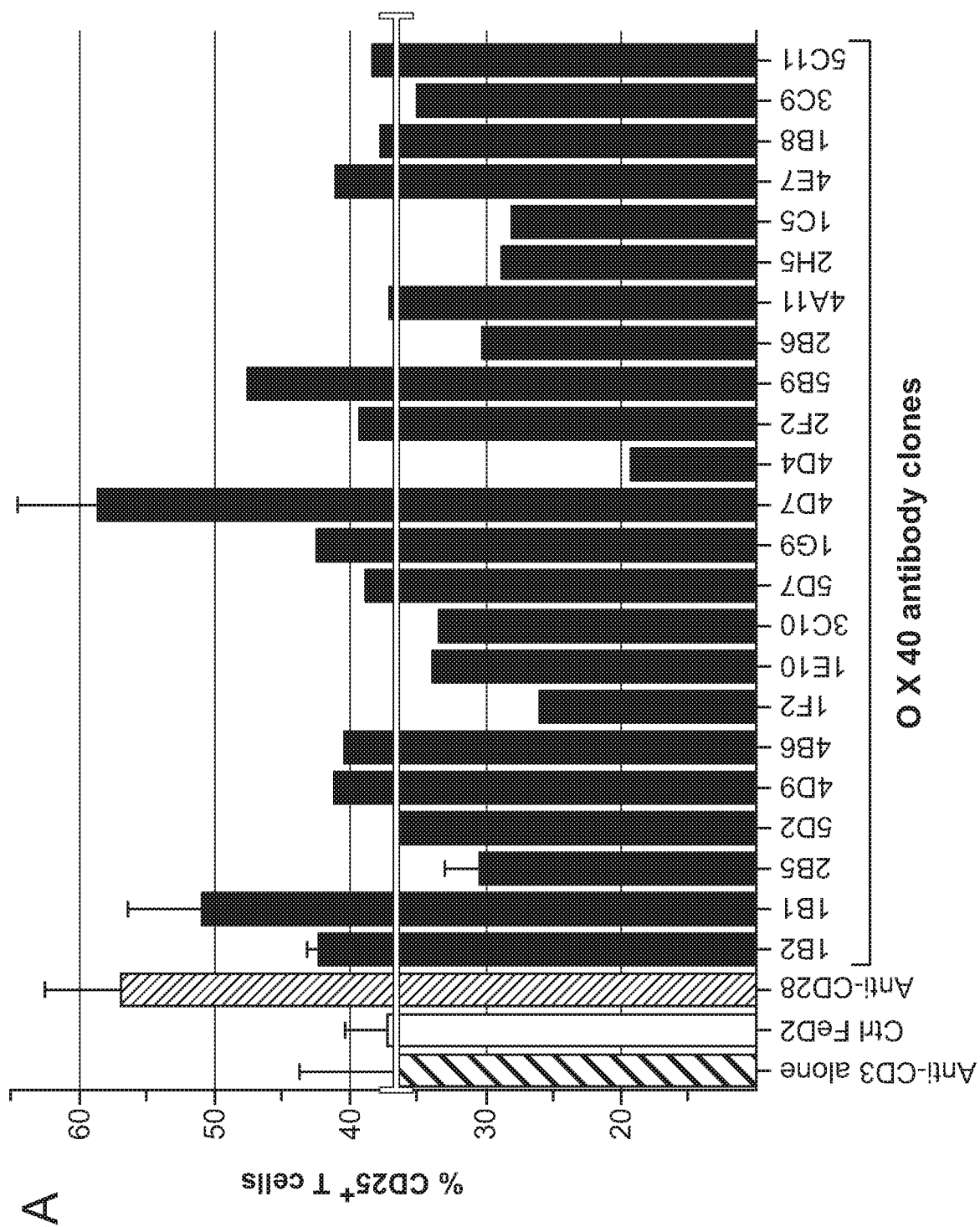
FIG. 4A is a graph that shows the percentage of CD3+ CD25+ activated T cells as measured by flow cytometry. Anti-CD3 alone and FeD2, an isotype control antibody, were used as negative controls. Anti-CD28 was used as a positive control. The line bisecting the graph shows the negative control levels of percentage of CD3+CD25+ activated T cells as a reference.
Figure 4B:
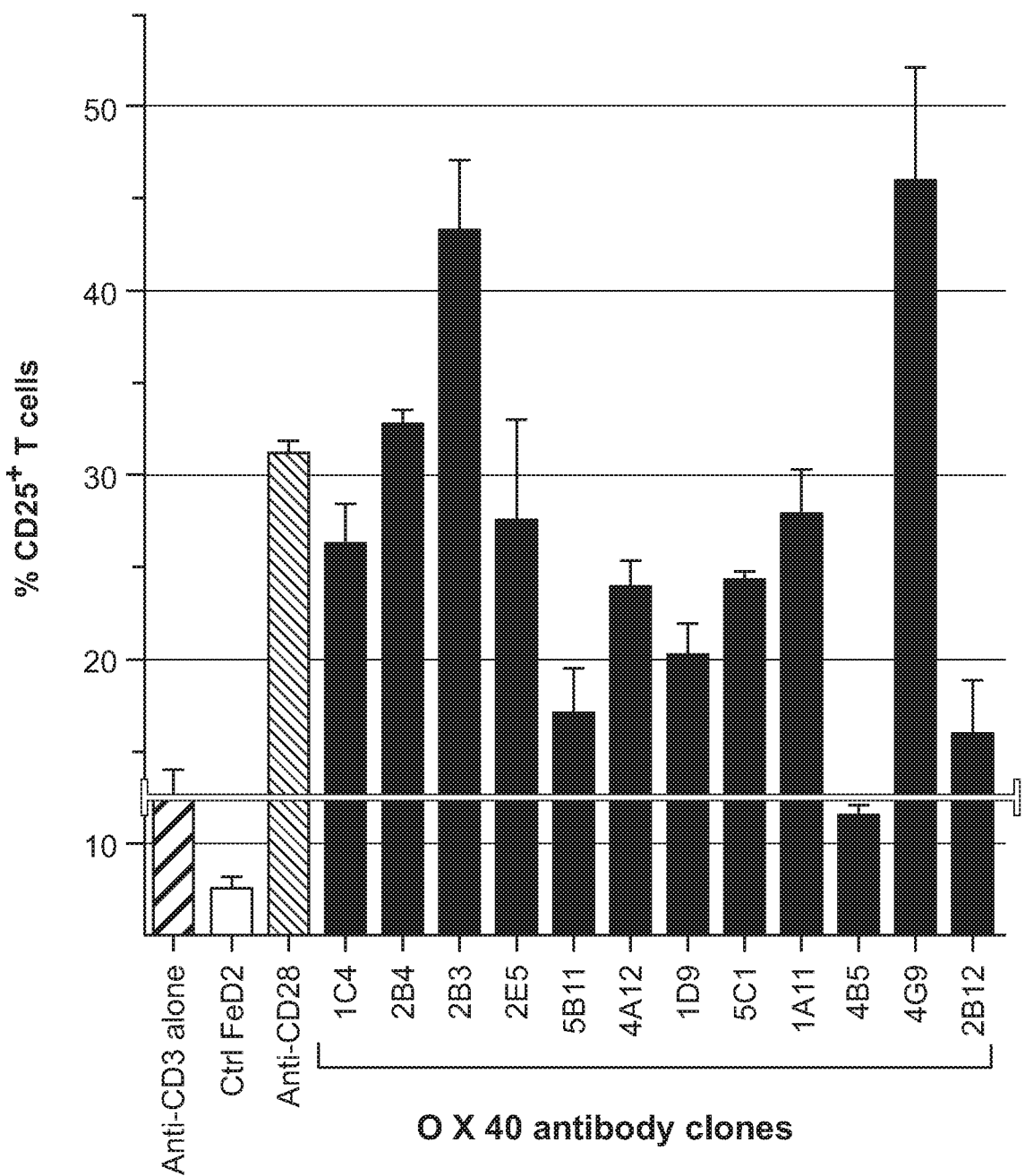
FIG. 4B is a graph that shows the percentage of CD3+ CD25+ activated T cells as measured by flow cytometry. Anti-CD3 alone and FeD2, an isotype control antibody, were used as negative controls. Anti-CD28 was used as a positive control. The line bisecting the graph shows the negative control levels of percentage of CD3+CD25+ activated T cells as a reference.

After 3 days the cells were transferred into a V-bottom 96-well plate and washed twice with cold FACS buffer (PBS1×+2% FCS), and then stained with PE-labelled anti-human CD25 (clone M-A251) at 5 µl/well in 70 µl of FACS buffer for 20 min at 4° C. The cells were spun at 1,500 rpm for 2 min and the supernatant was removed by quickly flipping the plate. Next, the cells were washed with 170 µl well of FACS buffer. The cells were spun at 1,500 rpm for 2 min and the supernatant was removed by quickly flipping the plate. The washing step was repeated twice. The percentage of CD3+CD25+ activated T cells was measured by flow cytometry. As shown in FIG. 4A and FIG. 4B, a number of anti-OX40 clones showed significant T cell co-stimulation. Among those clones showing T cell co-stimulation, clones 2B4, 4D7, 2B3, 4G9 and 1B1 showed the most robust agonist activity.

Taken together, the results from these experiments have identified particular candidate agonist clones, including 1A11, 2E5, 1B1, 4G9, 5C1, 4D7, 5B9, 1C4, 2B4 and 2B 3.

TABLE 1

Sequence Listing

| | Heavy chain variable domain regions | Light chain variable domain regions |
|---|---|---|
| Ox1A11 | EVQLVESGGGLVQTGGSLRLSCAASG FTFS<u>SYWMS</u>WVRQAPGKGLEWVA<u>NIK QDGSEKYYVDSVKG</u>RFTISRDNAKNS LYLQMNSLRAEDTAVYYCAR<u>DDYYYG MDV</u>WGQGTTVTSS SEQ ID NO. 1 | DVVMTQSPSSLSASVGDRVTITC<u>RAS QGIRNDLH</u>WYQQRPGKAPNLLIY<u>AAS SLHS</u>GVPSRFSGSGSGTDFTLTIDSL QPEDFATYYC<u>QQANSFPIT</u>FGQGTRL EIK SEQ ID NO. 2 |
| Ox1A11 | HC CDR1<br>SYWMS<br>SEQ ID NO. 49<br>HC CDR2<br>NIKQDGSEKYYVDSVKG<br>SEQ ID NO. 50<br>HC CDR3<br>DDYYYGMDV<br>SEQ ID NO. 51 | LC CDR1<br>RASQGIRNDLH<br>SEQ ID NO. 52<br>LC CDR2<br>AASSLHS<br>SEQ ID NO. 53<br>LC CDR3<br>QQANSFPIT<br>SEQ ID NO. 54 |
| Ox1B1 | QVQLVQSGAEVKKPGASVKVSCKASG YTFT<u>SYYMH</u>WVRQAPGQGLEWMG<u>IIN PSGGSTSYAQKFQG</u>RVTMTRDTSTST VYMELSSLRSDDTAVYYCAR<u>DPYSSS WYGAEYFQH</u>WGQGTLVTVSS SEQ ID NO. 3 | QSVLTQPPSASGTPGQRVTISC<u>SGSS SNIGSNYVY</u>WYQQLPGTAPKLLIY<u>RN NQRPS</u>GVPDRFSGSKSGTSASLAISG LRSEDEADYYC<u>AAWDDSLSGLV</u>FGGG TKLTVL SEQ ID NO. 4 |
| Ox1B1 | HC CDR1<br>SYYMH<br>SEQ ID NO. 55<br>HC CDR2<br>IINPSGGSTSYAQKFQG<br>SEQ ID NO. 56<br>HC CDR3<br>DPYSSSWYGAEYFQH<br>SEQ ID NO. 57 | LC CDR1<br>SGSSSNIGSNYVY<br>SEQ ID NO. 58<br>LC CDR2<br>RNNQRPS<br>SEQ ID NO. 59<br>LC CDR3<br>AAWDDSLSGLV<br>SEQ ID NO. 60 |
| Ox1B2 | QVQLVQSGAEVKKPGASVKVSCKASG YTFT<u>SYYMH</u>WVRQAPGQGLEWMG<u>IIN PSGGSTSYAQKFQG</u>RVTMTRDTSTST VYMELSSLRSEDTAVYYCAR<u>DYYDSS GYSDYGMDV</u>WGQGTTVTVSS SEQ ID NO. 5 | DIVMTQSPSSLSASVGDRVTITC<u>RAS QSISSYLN</u>WYQQKPGKAPKLLIY<u>AAS SLQS</u>GVPSRFSGSGSGTDFTLTISSL QPEDFAIYYC<u>QQNYNTRQVT</u>FGQGTR LEIK SEQ ID NO. 6 |
| Ox1B2 | HC CDR1<br>SYYMH<br>SEQ ID NO. 61<br>HC CDR2<br>IINPSGGSTSYAQKFQG<br>SEQ ID NO. 62<br>HC CDR3<br>DYYDSSGYSDYGMDV<br>SEQ ID NO. 63 | LC CDR1<br>RASQSISSYLN<br>SEQ ID NO. 64<br>LC CDR2<br>AASSLQS<br>SEQ ID NO. 65<br>LC CDR3<br>QQNYNTRQVT<br>SEQ ID NO. 66 |
| Ox1B3 | QVQLVQSGAEVKKPGASVKVSCKTSG YTFT<u>GYYLH</u>WVRQAPGQGLEWMG<u>IIN PSDGGTRYAQKFQD</u>RVTMTRDMSTST VYMELSSLRPEDTAVYYCAR<u>DLEYIG SGSLSWFDP</u>WGQGTLVTVSS SEQ ID NO. 7 | AIQLTQSPSSLSASVGDRVTITC<u>RAS QGISSALA</u>WYQQKPAKPKVLIY<u>DAS SLES</u>GVPSRFSGSGSGTDFTLTISSL QPEDFATYYC<u>QQFNNYPLT</u>FGGGTKV EIK SEQ ID NO. 8 |
| Ox1B3 | HC CDR1<br>GYYLH<br>SEQ ID NO. 67<br>HC CDR2<br>IINPSDGGTRYAQKFQD<br>SEQ ID NO. 68<br>HC CDR3<br>DLEYIGSGSLSWFDP<br>SEQ ID NO. 69 | LC CDR1<br>RASQGISSALA<br>SEQ ID NO. 70<br>LC CDR2<br>DASSLES<br>SEQ ID NO. 71<br>LC CDR3<br>QQFNNYPLT<br>SEQ ID NO. 72 |
| Ox1C4 | EVQLVESGAEVKKPGASVKVSCKTSG YTFT<u>GYYLH</u>WVRQAPGQGLEWMG<u>IIN PGDGSTRNAQKFEG</u>RVTMTRDTSTST VYMELSSLSPEDTAVYYCAR<u>DLEYIG SGSLSWFDP</u>WGQGTLVTVSS SEQ ID NO. 9 | LPVLTQPASVSGSPGQSITISC<u>SGTS SDFLTYDLVS</u>WYKQQPGKAPKLMIY<u>D VNKRPS</u>GVSDRFSGSKSGNTASLTIS GLQAADEADYYC<u>SSYTSSSTPYV</u>FGT GTKVTVL SEQ ID NO. 10 |

TABLE 1-continued

Sequence Listing

| | Heavy chain variable domain regions | Light chain variable domain regions |
|---|---|---|
| Ox1C4 | HC CDR1<br>GYYLH<br>SEQ ID NO. 73<br>HC CDR2<br>IINPGDGSTRNAQKFEG<br>SEQ ID NO. 74<br>HC CDR3<br>DLEYIGSGSLSWFDP<br>SEQ ID NO. 75 | LC CDR1<br>SGTSSDFLTYDLVS<br>SEQ ID NO. 76<br>LC CDR2<br>DVNKRPS<br>SEQ ID NO. 77<br>LC CDR3<br>SSYTSSSTPYV<br>SEQ ID NO. 78 |
| Ox1C5 | QVQLVQSGAEVKKPGASVKVSCKASG YTFT<u>SYYMH</u>WVRQAPGQGLEWMG<u>IIN PSGGSTSYAQKFQG</u>RVTMTTDTSTST AYMELRSLRSDDTAVYYCARD<u>PYSSS WYGAEYFQH</u>WGQGTLVTVSS SEQ ID NO. 11 | QSVLTQPRSVSGSPGQSVTISC<u>TGTS SDGGDYNYVS</u>WYQQKPGQAPKLLIYE <u>VSNRPS</u>GVSNRFSGSKSGNTASLTIS GLQAEDEADYYC<u>SSYTSSSTLVV</u>FGG GTKLTVL SEQ ID NO. 12 |
| Ox1C5 | HC CDR1<br>SYYMH<br>SEQ ID NO. 79<br>HC CDR2<br>IINPSGGSTSYAQKFQG<br>SEQ ID NO. 80<br>HC CDR3<br>DPYSSSWYGAEYFQH<br>SEQ ID NO. 81 | LC CDR1<br>TGTSSDGGDYNYVS<br>SEQ ID NO. 82<br>LC CDR2<br>EVSNRPS<br>SEQ ID NO. 83<br>LC CDR3<br>SSYTSSSTLVV<br>SEQ ID NO. 84 |
| Ox1D9 | QVQLVQSGAEVKKPGASVKVSCKASG YTFT<u>SYGIS</u>WVRQALGQRLEWLG<u>WIN AGDGETKYSPKFQG</u>RVTITRDTSAST AYMDLSGLTSEDTAVYYCARD<u>FLSTM DY</u>WGQGTLVTVSS SEQ ID NO. 13 | DVVMTQSPSSLSASVGDRVTITC<u>QAS QDISNYLN</u>WYQQKPGKAPKLLIY<u>DAS NLET</u>GVPSRFSGGGSGTDFTFTISSL QPEDIATYYC<u>QQFDNLPYT</u>FGQGTKV EIK SEQ ID NO. 14 |
| Ox1D9 | HC CDR1<br>SYGIS<br>SEQ ID NO. 85<br>HC CDR2<br>WINAGDGETKYSPKFQG<br>SEQ ID NO. 86<br>HC CDR3<br>DFLSTMDY<br>SEQ ID NO. 87 | LC CDR1<br>QASQDISNYLN<br>SEQ ID NO. 88<br>LC CDR2<br>DASNLET<br>SEQ ID NO. 89<br>LC CDR3<br>QQFDNLPYT<br>SEQ ID NO. 90 |
| Ox1E10 | EVQLVESGAEVKKPGASVKVSCKTSG YTFT<u>GYYLH</u>WVRQAPGQGLQWMG<u>WIN PTSGDTNYAPEYQG</u>RVTMTRDTSIST AYMELSSLRSDDTAVYYCAR<u>GHDYSR TPVGAEALDY</u>WGQGTLVTVSS SEQ ID NO. 15 | QPVLTQPPSASGSPGQSVTISC<u>TGTS SDIGGYNYVS</u>WYQQHPGKAPKLLIYE <u>VSKRPS</u>GVPARFAGSKSGNTASLTVS GLQAEDEADYYC<u>SSYAGNNNHV</u>FGTG TKLTVL SEQ ID NO. 16 |
| Ox1E10 | HC CDR1<br>GYYLH<br>SEQ ID NO. 91<br>HC CDR2<br>WINPTSGDTNYAPEYQG<br>SEQ ID NO. 92<br>HC CDR3<br>GHDYSRTPVGAEALDY<br>SEQ ID NO. 93 | LC CDR1<br>TGTSSDIGGYNYVS<br>SEQ ID NO. 94<br>LC CDR2<br>EVSKRPS<br>SEQ ID NO. 95<br>LC CDR3<br>SSYAGNNNHV<br>SEQ ID NO. 96 |
| Ox1E7 | QVQLVQSGAEVKKPGASVKVSCKTSG YTFT<u>GYYLH</u>WVRQAPGQGLEWMG<u>IIN PSDGGTRYAQKFQD</u>RVTMTRDMSTST VYMELSSLRPEDTAVYYCAR<u>DLEYIG SGSLSWFDP</u>WGQGTLVTVSS SEQ ID NO. 7 | QSVLTQPASVSGSPGQSITIPC<u>TGTS NDIGTYNLAS</u>WYQHHAGKAPKLIIY<u>D LNHRPS</u>GVSNRFSGYKSDNTAFLTIS GLQPEDESNYYC<u>SSYTMNTTPIL</u>FGG GTKLTVL SEQ ID NO. 17 |
| Ox1E7 | HC CDR1<br>GYYLH<br>SEQ ID NO. 67<br>HC CDR2<br>IINPSDGGTRYAQKFQD<br>SEQ ID NO. 68<br>HC CDR3 | LC CDR1<br>TGTSNDIGTYNLAS<br>SEQ ID NO. 97<br>LC CDR2<br>DLNHRPS<br>SEQ ID NO. 98<br>LC CDR3 |

TABLE 1-continued

Sequence Listing

| | Heavy chain variable domain regions | Light chain variable domain regions |
|---|---|---|
| | DLEYIGSGSLSWFDP<br>SEQ ID NO. 69 | SSYTMNTTPIL<br>SEQ ID NO. 99 |
| Ox1F2 | QVQLVQSGAEVKKPGASVKVSCKASG YTFTSYYMHWRQAPGQGLEWMGIIN PSGGSTSYAQKFQGRVTMTRDTSTST VYMELSSLRSDDTAVYYCARDPYSSS WYGAEYFQHWGQGTLVTVSS SEQ ID NO. 3 | QPVLTQPPSASGTPGQRVTISCSGSS SNIGNNFVYWYQQLPGMAPKLLIYKN NQRPSGVPDRFSGSKSGTSASLAISG LRSEDEADYHCAAWDDSLSGHVVFGG GTKLTVL SEQ ID NO. 18 |
| Ox1F2 | HC CDR1<br>SYYMH<br>SEQ ID NO. 55<br>HC CDR2<br>IINPSGGSTSYAQKFQG<br>SEQ ID NO. 56<br>HC CDR3<br>DPYSSSWYGAEYFQH<br>SEQ ID NO. 57 | LC CDR1<br>SGSSSNIGNNFVY<br>SEQ ID NO. 100<br>LC CDR2<br>KNNQRPS<br>SEQ ID NO. 101<br>LC CDR3<br>AAWDDSLSGHVV<br>SEQ ID NO. 102 |
| Ox1G9 | QVQLVQSGAEVKKPGASVKVSCKTSG YTFTGYYLHWRQAPGQGLEWMGIIN PSDGSTRNAQKFEGRVTMTRDTSTST VYMELSSLSPEDTAVYYCARDLEYIG SGSLSWFDPWGQGTLVTVSS SEQ ID NO. 19 | QSVLTQPASVSGSPGQSVTVSCTGTS SDIGAYESVSWYQQHPGKGPKLIIYD VSSRPSGVSIRFSGSKSGNSASLTIS GLQAEDEAEYFCSSFTRGSTPYVFGT GTKVTVL SEQ ID NO. 20 |
| Ox1G9 | HC CDR1<br>GYYLH<br>SEQ ID NO. 103<br>HC CDR2<br>IINPSDGSTRNAQKFEG<br>SEQ ID NO. 104<br>HC CDR3<br>DLEYIGSGSLSWFDP<br>SEQ ID NO. 105 | LC CDR1<br>TGTSSDIGAYESVS<br>SEQ ID NO. 106<br>LC CDR2<br>DVSSRPS<br>SEQ ID NO. 107<br>LC CDR3<br>SSFTRGSTPYV<br>SEQ ID NO. 108 |
| Ox2B12 | QVQLVQSGAEVKKPGASVKVSCKASG YTFSNYYMHWRQAPGQGLEWMGLLN PSGGYTTYAQRFQGRVTMTWDTSTST VYMELSSLTSEDTAVYYCAKDPYSSS WYGAEYFQHWGQGTLVTVSS SEQ ID NO. 21 | QSVLTQPASVSGSPGQSITISCTGTS SDVGAYNYVSWYQQHPGRAPKLMIYD VSDRPSGVSNRFSGSKSGNTASLTIS GLQAEDEADYYCSSYTSSSSLYVFGT GTKVTVL SEQ ID NO. 22 |
| Ox2B12 | HC CDR1<br>NYYMH<br>SEQ ID NO. 109<br>HC CDR2<br>LLNPSGGYTTYAQRFQG<br>SEQ ID NO. 110<br>HC CDR3<br>DPYSSSWYGAEYFQH<br>SEQ ID NO. 111 | LC CDR1<br>TGTSSDVGAYNYVS<br>SEQ ID NO. 112<br>LC CDR2<br>DVSDRPS<br>SEQ ID NO. 113<br>LC CDR3<br>SSYTSSSSLYV<br>SEQ ID NO. 114 |
| Ox2B3 | QVQLVQSGAEVKKPGASVKVSCKTSG YTFTGYYLHWRQAPGQGLEWMGIIN PSDGGTRYAQKFQDRVTMTRDMSTST VYMELSSLRPEDTAVYYCARDLEYIG SGSLSWFDPWGQGTLVTVSS SEQ ID NO. 7 | QSVLTQPASVSGSPGQSITISCTGSS SDIGGYNSVSWYQQYPGKAPKLMIHD VNERPSGISDRFSGSKSGNTASLTIS GLQEEDEAEYYCASYSVFSPFLFGRG TKLTVL SEQ ID NO. 23 |
| Ox2B3 | HC CDR1<br>GYYLH<br>SEQ ID NO. 67<br>HC CDR2<br>IINPSDGGTRYAQKFQD<br>SEQ ID NO. 68<br>HC CDR3<br>DLEYIGSGSLSWFDP<br>SEQ ID NO. 69 | LC CDR1<br>TGSSSDIGGYNSVS<br>SEQ ID NO. 115<br>LC CDR2<br>DVNERPS<br>SEQ ID NO. 116<br>LC CDR3<br>ASYSVFSPFL<br>SEQ ID NO. 117 |
| Ox2B4 | QMQLVQSGAEVKKPGASVKVSCKTSG YTFTGYYLHWRQAPGQGLEWMGIIN PSDGSTRNAQKFEGRVTMTRDTSTST VYMELSSLSPEDTAVYYCARDLEYIG | QPVLTQPASVSGSPGQSITISCTGTS SDLGAYDYVSWYQQQPGQAPKLIIYD VNNRPSGVSNRFSGSKSGNTASLTIS GLQAEDEADYYCSSYTSSSTLVYVFG |

TABLE 1-continued

Sequence Listing

| | Heavy chain variable domain regions | Light chain variable domain regions |
|---|---|---|
| | SGSLSWFDPWGQGTLVTVSS SEQ ID NO. 24 | TGTKVTVL SEQ ID NO. 25 |
| Ox2B4 | HC CDR1<br>GYYLH<br>SEQ ID NO. 118<br>HC CDR2<br>IINPSDGSTRNAQKFEG<br>SEQ ID NO. 119<br>HC CDR3<br>DLEYIGSGSLSWFDP<br>SEQ ID NO. 120 | LC CDR1<br>TGTSSDLGAYDYVS<br>SEQ ID NO. 121<br>LC CDR2<br>DVNNRPS<br>SEQ ID NO. 122<br>LC CDR3<br>SSYTSSSTLVYV<br>SEQ ID NO. 123 |
| Ox2B6 | QVQLVQSGAEVKKPGASVKVSCKTSG YTFTGYYLHWVRQAPGQGLEWMGIIN PSDGGTRYAQKFQDRVTMTRDMSTST VYMELSSLRPEDTAVYYCARDLEYIG SGSLSWFDPWGQGTLVTVSS SEQ ID NO. 7 | LPVLTQPASVSGSPGQSITISCTGTS SDVGYYDSVSWYQQYPGKAPKLLIYD VSKRPSGVSNRFSGSKSGNTASLTIS GLQADDEAEYHCSSYSDSSPFVFGTG TKVTVL SEQ ID NO. 26 |
| Ox2B6 | HC CDR1<br>GYYLH<br>SEQ ID NO. 67<br>HC CDR2<br>IINPSDGGTRYAQKFQD<br>SEQ ID NO. 68<br>HC CDR3<br>DLEYIGSGSLSWFDP<br>SEQ ID NO. 69 | LC CDR1<br>TGTSSDVGYYDSVS<br>SEQ ID NO. 124<br>LC CDR2<br>DVSKRPS<br>SEQ ID NO. 125<br>LC CDR3<br>SSYSDSSPFV<br>SEQ ID NO. 126 |
| Ox2F2 | QVQLVQSGAEVKKPGASVKVSCKTSG YTFTGYYLHWVRQAPGQGLEWMGIIN PSDGGTRYAQKFQDRVTMTRDMSTST VYMELSSLRPEDTAVYYCARDLEYIG SGSLSWFDPWGQGTLVTVSS SEQ ID NO. 7 | LPVLTQPASVSGSPGQSITISCTGAS SDVGGYNSVSWYQQHPGKAPKLMIYD VSNRPSGISNRFSGSKSGNTASLTVS GLQAEDEADYYCSSYAGSNIVYVFGT GTKVTVL SEQ ID NO. 27 |
| Ox2F2 | HC CDR1<br>GYYLH<br>SEQ ID NO. 67<br>HC CDR2<br>IINPSDGGTRYAQKFQD<br>SEQ ID NO. 68<br>HC CDR3<br>DLEYIGSGSLSWFDP<br>SEQ ID NO. 69 | LC CDR1<br>TGASSDVGGYNSVS<br>SEQ ID NO. 127<br>LC CDR2<br>DVSNRPS<br>SEQ ID NO. 128<br>LC CDR3<br>SSYAGSNIVYV<br>SEQ ID NO. 129 |
| Ox2G2 | QVQLVQSGAEVKKPGASVKVSCKTSG YTFTGYYLHWVRQAPGQGLEWMGIIN PSDGGTRYAQKFQDRVTMTRDMSTST VYMELSSLRPEDTAVYYCARDLEYIG SGSLSWFDPWGQGTLVTVSS SEQ ID NO. 7 | QPVLTQPASVSGSPGQSITISCTGTT SDIGGYNSVSWYQQHPGRAPKLIIYD VTYRPSGVSNRFSGSKSGNTASLTIS GLQAEDEADYYCSSYTSGNSVYVFGT GTKLTVL SEQ ID NO. 28 |
| Ox2G2 | HC CDR1<br>GYYLH<br>SEQ ID NO. 67<br>HC CDR2<br>IINPSDGGTRYAQKFQD<br>SEQ ID NO. 68<br>HC CDR3<br>DLEYIGSGSLSWFDP<br>SEQ ID NO. 69 | LC CDR1<br>TGTTSDIGGYNSVS<br>SEQ ID NO. 130<br>LC CDR2<br>DVTYRPS<br>SEQ ID NO. 131<br>LC CDR3<br>SSYTSGNSVYV<br>SEQ ID NO. 132 |
| Ox3C10 | EVQLVQSGAEVKKPGASVKVSCKASG YTFTSYYMHWVRQAPGQGLEWMGIIN PSGGSTSYAQKFQGRVTMTRDTSTST VYMELSSLRSEDTAVYYCARDFSSWY AYGMDVWGQGTTVTVSS SEQ ID NO. 29 | EIVLTQSPSSLSASVGDRVTITCRAS QDISSALAWYQQKPGEPPNLLIYDAS TLEGGVPSRFSGSGSGTDFTLTISSL QPEDFATYSCQQFRTYPLTFGGGTKL EIK SEQ ID NO. 30 |
| Ox3C10 | HC CDR1<br>SYYMH<br>SEQ ID NO. 133<br>HC CDR2 | LC CDR1<br>RASQDISSALA<br>SEQ ID NO. 136<br>LC CDR2 |

TABLE 1-continued

Sequence Listing

| | Heavy chain variable domain regions | Light chain variable domain regions |
|---|---|---|
| | IINPSGGSTSYAQKFQG<br>SEQ ID NO. 134<br>HC CDR3<br>DFSSWYAYGMDV<br>SEQ ID NO. 135 | DASTLEG<br>SEQ ID NO. 137<br>LC CDR3<br>QQFRTYPLT<br>SEQ ID NO. 138 |
| Ox4A11 | EVQLLESGAEVKKPGASVKVSCKASG YTFT<u>SYYMH</u>WVRQAPGQGLEWMG<u>IIN PSGGSTSYAQKFQG</u>RVTMTRDTSTST VYMELSSLRSEDTAVYYCAR<u>STLWFS EFDY</u>WGQGTLVTVSS SEQ ID NO. 31 | QPVLTQPPSVSAAPGQKVTISC<u>SGSS SNIGNNYVS</u>WYQQLPGTAPKLLIY<u>DN DKRPS</u>GIPDRFSGSTSGTSATLGIAG LQTGDEADYYC<u>GTWDSSLGWV</u>FGGGT KLTVL SEQ ID NO. 32 |
| Ox4A11 | HC CDR1<br>SYYMH<br>SEQ ID NO. 139<br>HC CDR2<br>IINPSGGSTSYAQKFQG<br>SEQ ID NO. 140<br>HC CDR3<br>STLWFSEFDY<br>SEQ ID NO. 141 | LC CDR1<br>SGSSSNIGNNYVS<br>SEQ ID NO. 142<br>LC CDR2<br>DNDKRPS<br>SEQ ID NO. 143<br>LC CDR3<br>GTWDSSLGWV<br>SEQ ID NO. 144 |
| Ox4A12 | QVQLVQSGAEVKKPGASVKVSCKASG YTFT<u>SYYMH</u>WVRQAPGQGLEWMG<u>IIN PSGGSTSYAQKFQG</u>RVTMTRDTSTST VYMELSSLRSDDTAVYYCAR<u>DPYSSS WYGAEYFQH</u>WGQGTLVTVSS SEQ ID NO. 3 | QSVLTQPRSVSGSPGQSVTISC<u>TGTS SDGGDYNYVS</u>WYQQHPGQAPKLLIYE <u>VSNRPS</u>GVSNRFSGSKSGNTASLTIS GLQAEDEADYYC<u>SSYTSSSTLVV</u>FGG GTKLTVL SEQ ID NO. 33 |
| Ox4A12 | HC CDR1<br>SYYMH<br>SEQ ID NO. 55<br>HC CDR2<br>IINPSGGSTSYAQKFQG<br>SEQ ID NO. 56<br>HC CDR3<br>DPYSSSWYGAEYFQH<br>SEQ ID NO. 57 | LC CDR1<br>TGTSSDGGDYNYVS<br>SEQ ID NO. 145<br>LC CDR2<br>EVSNRPS<br>SEQ ID NO. 146<br>LC CDR3<br>SSYTSSSTLVV<br>SEQ ID NO. 147 |
| Ox4B6 | EVQLVQSGAEVKKPGASVKVSCKASG YTFT<u>SYYMH</u>WVRQAPGQGLEWMG<u>IIN PSGGSTSYAQKFQG</u>RVTMTRDTSTST VYMELSSLRSEDTAVYYCAR<u>DFSSWY AYGMDV</u>WGQGTTVTVSS SEQ ID NO. 34 | EIVLTQSPSSLSASVGDRVTITC<u>RAS QDISSALA</u>WYQQKPGEPPNLLIY<u>DAS TLEG</u>GVPSRFSGSGSGTDFTLTISSL QPEDFATYC<u>QQFRTYPLT</u>FGGGTKL EIK SEQ ID NO. 35 |
| Ox4B6 | HC CDR1<br>SYYMH<br>SEQ ID NO. 148<br>HC CDR2<br>IINPSGGSTSYAQKFQG<br>SEQ ID NO. 149<br>HC CDR3<br>DFSSWYAYGMDV<br>SEQ ID NO. 150 | LC CDR1<br>RASQDISSALA<br>SEQ ID NO. 151<br>LC CDR2<br>DASTLEG<br>SEQ ID NO. 152<br>LC CDR3<br>QQFRTYPLT<br>SEQ ID NO. 153 |
| Ox4D4 | QVQLVQSGAEVKKPGASVKVSCKTSG YTFT<u>GYYLH</u>WVRQAPGQGLEWMG<u>IIN PSDGGTRYAQKFQD</u>RVTMTRDMSTST VYMELSSLRPEDTAVYYCAR<u>DLEYIG SGSLSWFDP</u>WGQGTLVTVSS SEQ ID NO. 7 | LPVLTQPASVSGSPGQSITISC<u>TGTS SDVGAYNSVS</u>WYQQRPGKAPKLMIY<u>D VIQRPS</u>EVSHRFSGSKSGNTASLTIS GLLPEDEAEYFC<u>GSYAASTTFV</u>FGGG TKLTVL SEQ ID NO. 36 |
| Ox4D4 | HC CDR1<br>GYYLH<br>SEQ ID NO. 67<br>HC CDR2<br>IINPSDGGTRYAQKFQD<br>SEQ ID NO. 68<br>HC CDR3<br>DLEYIGSGSLSWFDP<br>SEQ ID NO. 69 | LC CDR1<br>TGTSSDVGAYNSVS<br>SEQ ID NO. 154<br>LC CDR2<br>DVIQRPS<br>SEQ ID NO. 155<br>LC CDR3<br>GSYAASTTFV<br>SEQ ID NO. 156 |
| Ox4D7 | QVQLVQSGAEVKKPGASVKVSCKASG | QSVLTQPRSVSGSPGQSVTISC<u>TGTS</u> |

TABLE 1-continued

Sequence Listing

| | Heavy chain variable domain regions | Light chain variable domain regions |
|---|---|---|
| | YTFTSYYMHWVRQAPGQGLEWMGIIN PSGGSTSYAQKFQGRVTMTTDTSTST AYMELRSLRSDDTAVYYCARDPYSSS WYGAEYFQHWGQGTLVTVSS SEQ ID NO. 37 | SDGGDYNYVSWYQQHPGQAPKLLIYE VSNRPSGVSNRFSGSKSGNTASLTIS GLQAEDEADYYCSSYTSSSTLVVFGG GTKLTVL SEQ ID NO. 38 |
| 0x4D7 | HC CDR1<br>SYYMH<br>SEQ ID NO. 157<br>HC CDR2<br>IINPSGGSTSYAQKFQG<br>SEQ ID NO. 158<br>HC CDR3<br>DPYSSSWYGAEYFQH<br>SEQ ID NO. 159 | LC CDR1<br>TGTSSDGGDYNYVS<br>SEQ ID NO. 160<br>LC CDR2<br>EVSNRPS<br>SEQ ID NO. 161<br>LC CDR3<br>SSYTSSSTLVV<br>SEQ ID NO. 162 |
| 0x4D9 | EVQLVQSGAEVKKPGASVKLSCKASG YTFTSYFMHWVRQAPGQGLEWMGIIN PSGGSTSYAQKFQGRLTMTRDTSTST AYMELRSLRSDDTAVYYCARDPYSSS WYGAEYFQHWGQGTLVTVSS SEQ ID NO. 39 | QPVLTQPPSASGTPGQRVSISCSGSS SNIGTNTVNWYQQLPGTAPKLLVYSN NQRPSGVPDRFSGSKSGTSASLAISG LQSEDEADYFCSAWDDSLNGQVFGAG TKVTVL SEQ ID NO. 40 |
| 0x4D9 | HC CDR1<br>YFMH<br>SEQ ID NO. 163<br>HC CDR2<br>IINPSGGSTSYAQKFQG<br>SEQ ID NO. 164<br>HC CDR3<br>DPYSSSWYGAEYFQH<br>SEQ ID NO. 165 | LC CDR1<br>SGSSSNIGTNTVN<br>SEQ ID NO. 166<br>LC CDR2<br>SNNQRPS<br>SEQ ID NO. 167<br>LC CDR3<br>SAWDDSLNGQV<br>SEQ ID NO. 168 |
| 0x4G9 | QVQLVQSGAEVKKPGASVKVSCKTSG YTFTGYYLHWVRQAPGQGLEWMGIIN PSDGGTRYAQKFQDRVTMTRDMSTST VYMELSSLRPEDTAVYYCARDLEYIG SGSLSWFDPWGQGTLVTVSS SEQ ID NO. 7 | LPVLTQPASVSGSPGQSITISCTGTS SDVGYYDSVSWYQQYPGKAPKLLIYD VSKRPSGVSNRFSGSKSGNTASLTIS GLQADDEAEYHCSSYSDSSPFVFGTG TKVTVL SEQ ID NO. 41 |
| 0x4G9 | HC CDR1<br>GYYLH<br>SEQ ID NO. 67<br>CDR2<br>IINPSDGGTRYAQKFQD<br>SEQ ID NO. 68<br>HC CDR3<br>DLEYIGSGSLSWFDP<br>SEQ ID NO. 69 | LC CDR1<br>TGTSSDVGYYDSVS<br>SEQ ID NO. 169<br>LC CDR2<br>DVSKRPS<br>SEQ ID NO. 170<br>LC CDR3<br>SSYSDSSPFV<br>SEQ ID NO. 171 |
| 0x4H4 | EVQLVQSGGGLVQPGGSLRLSCAASG FSFSGYDMSWVRQAPGKGLEWVSSIS TSGGSTNYADSVNGRFIISRDNSKNT LYLQMNSLRTEDTAVYYCAREGSGWY DAGYFDYWGQGTLVTVSS SEQ ID NO. 42 | DIVMTQSPSSLSASVGDRVTITCQAS QDISNSLNWYQQKPGKAPNLLIYDAS TLQRGVPSRFSGSGSGTKFTFTISSL QPEDIATYYCQQYANLPPITFGQGTR LEIK SEQ ID NO. 43 |
| 0x4H4 | HC CDR1<br>GYDMS<br>SEQ ID NO. 172<br>HC CDR2<br>SISTSGGSTNYADSVNG<br>SEQ ID NO. 173<br>HC CDR3<br>EGSGWYDAGYFDY<br>SEQ ID NO. 174 | LC CDR1<br>QASQDISNSLN<br>SEQ ID NO. 175<br>LC CDR2<br>DASTLQR<br>SEQ ID NO. 176<br>LC CDR3<br>QQYANLPPIT<br>SEQ ID NO. 177 |
| 0x5B9 | QVQLVQSGAEVKKPGASVKVSCKTSG YTFTGYYLHWVRQAPGQGLEWMGIIN PSDGGTRYAQKFQDRVTMTRDMSTST VYMELSSLRPEDTAVYYCARDLEYIG SGSLSWFDPWGQGTLVTVSS SEQ ID NO. 44 | LPVLTQPASVSGSPGQSITISCTGTT SDIGGYNSVSWYQQHPGRAPKLIIYD VTYRPSGVSNRFSGSKSGNTASLTIS GLQAEDEADYYCSSYTSGNSVYVFGT GTKLTVL SEQ ID NO. 45 |
| 0x5B9 | HC CDR1 | LC CDR1 |

TABLE 1-continued

Sequence Listing

| | Heavy chain variable domain regions | Light chain variable domain regions |
|---|---|---|
| | GYYLH<br>SEQ ID NO. 178<br>HC CDR2<br>IINPSDGGTRYAQKFQD<br>SEQ ID NO. 179<br>HC CDR3<br>DLEYIGSGSLSWFDP<br>SEQ ID NO. 180 | TGTTSDIGGYNSVS<br>SEQ ID NO. 181<br>LC CDR2<br>DVTYRPS<br>SEQ ID NO. 182<br>LC CDR3<br>SSYTSGNSVYV<br>SEQ ID NO. 183 |
| Ox5C1 | EVQLVQSGGGLVQPGQSLRLSCTPYG<br>FSFNDYGMSWVRQAPGKGLEWLAFVG<br>SKASGGASENVAAVQGRFSFSRDDAK<br>GIAYLQLNNLKPEDTGVYFCTRDLGT<br>SGPYFFDYWGQGTLVTVSS SEQ<br>ID NO. 46 | LPVLTQSPSVSVSPGQTGYMNCYGHE<br>LTDKYVSWYQKKPGQSPVLVIYEDTK<br>RPSGIPDRFSGSNSGDTATLTISGTQ<br>ALDEADYYCQAWDSNTVIFGGGTKLT<br>VL SEQ ID NO. 47 |
| Ox5C1 | HC CDR1<br>DYGMS<br>SEQ ID NO. 184<br>HC CDR2<br>FVGSKASGGASENVAAVQG<br>SEQ ID NO. 185<br>HC CDR3<br>DLGTSGPYFFDY<br>SEQ ID NO. 186 | LC CDR1<br>YGHELTDKYVS<br>SEQ ID NO. 187<br>LC CDR2<br>EDTKRPS<br>SEQ ID NO. 188<br>LC CDR3<br>QAWDSNTVI<br>SEQ ID NO. 189 |
| Ox5D7 | QVQLVQSGAEVKKPGASVKVSCKTSG<br>YTFTGYYLHWVRQAPGQGLEWMGIIN<br>PSDGGTRYAQKFQDRVTMTRDMSTST<br>VYMELSSLRPEDTAVYYCARDLEYIG<br>SGSLSWFDPWGQGTLVTVSS SEQ<br>ID NO. 7 | LPVLTQPPSVSAAPGQKVTISCSGSS<br>SNIGNNYVSWYQQLPGTAPKLLIYDN<br>NERPSGIPDRFSGSKSGNTASLTISG<br>LQAEDEADYYCSSYTDRDTPYVFGGG<br>TKVTVL SEQ ID NO. 48 |
| Ox5D7 | HC CDR1<br>GYYLH<br>SEQ ID NO. 67<br>HC CDR2<br>IINPSDGGTRYAQKFQD<br>SEQ ID NO. 68<br>HC CDR3<br>DLEYIGSGSLSWFDP<br>SEQ ID NO. 69 | LC CDR1<br>SGSSSNIGNNYVS<br>SEQ ID NO. 190<br>LC CDR2<br>DNNERPS<br>SEQ ID NO. 191<br>LC CDR3<br>SSYTDRDTPYV<br>SEQ ID NO. 192 |
| Ox4B5 | QMQLVQSGAEVKKPGASVKVSCKASG<br>YTFTNFFMHWVRQAPGQGLEWMGIIN<br>PSGGSTSYAQKFQGRVTMTRDTSTST<br>VYMELSSLRSEDTAVYYCARDRELLW<br>FGELSGAFDIWGQGTMVTVSS<br>SEQ ID NO. 193 | DIVMTQSPSSLSASVGDRVTITCQAS<br>QDISKYLNWYQQKPGKAPKLLIYDAS<br>NLETGVPSRFSGSGSGTDFSFTISNL<br>QPEDIATYYCQQSANLPITFGQGTKV<br>EIK SEQ ID NO. 194 |
| Ox4B5 | HC CDR1<br>NFFMH<br>SEQ ID NO. 195<br>HC CDR2<br>IINPSGGSTSYAQKFQG<br>SEQ ID NO. 196<br>HC CDR3<br>DRELLWFGELSGAFDI<br>SEQ ID NO. 197 | LC CDR1<br>QASQDISKYLN<br>SEQ ID NO. 198<br>LC CDR2<br>DASNLET<br>SEQ ID NO. 199<br>LC CDR3<br>QQSANLPIT<br>SEQ ID NO. 200 |
| Ox2E5 | EVQLVQSGAEVKKPGASVTLSCKASG<br>HTFTNYYMHWVRQAPGQGLEWMGIIN<br>PGGGGTSYAQKFHDRVAMTRDTSTST<br>VYMELSSLRSEDTAVYYCTRGLYSAY<br>DSPSDLWGQGTLVTVSS SEQ ID<br>NO. 201 | QSVLTQPASVSASPGQSITISCTGAS<br>SDIGGYDYVSWYQQHSGKAPKLMIYE<br>ASKRPSGVSHRFSGSKSGNTASLIIS<br>GLQAEDEADYYCSSHTTSSTWVFGGG<br>TKLTVL SEQ ID NO. 202 |
| Ox2E5 | HC CDR1<br>NYYMH<br>SEQ ID NO. 203<br>HC CDR2<br>IINPGGGGTSYAQKFHD<br>SEQ ID NO. 204<br>HC CDR3<br>GLYSAYDSPSDL | LC CDR1<br>TGASSDIGGYDYVS<br>SEQ ID NO. 206<br>LC CDR2<br>EASKRPS<br>SEQ ID NO. 207<br>LC CDR3<br>SSHTTSSTWV |

TABLE 1-continued

Sequence Listing

| | Heavy chain variable domain regions | Light chain variable domain regions |
|---|---|---|
| | SEQ ID NO. 205 | SEQ ID NO. 208 |
| Ox2B5 | QVQLVQSGAEVKKPGASVKVSCKASG YTFT<u>SYYMH</u>WVRQAPGQGLEWMG<u>IIN PSGGSTSYAQKFQ</u>GRVTMTRDTSTST VYMELSSLRSEDTAVYYCAR<u>DYYDSS GYSDYGMDV</u>WGQGTTVTVSS SEQ ID NO. 5 | DIQMTQSPSSLSASLGDRVTITC<u>RAN QSISRYLN</u>WYQHKPGKAPKLLIY<u>AAS SLQS</u>GVPSRFSGNGSGTDFTLTISSL QPEDFATYYC<u>QQSYSTPSIT</u>FGQGTR LEIK SEQ ID NO. 209 |
| Ox2B5 | HC CDR1<br>SYYMH<br>SEQ ID NO. 61<br>HC CDR2<br>IINPSGGSTSYAQKFQG<br>SEQ ID NO. 62<br>HC CDR3<br>DYYDSSGYSDYGMDV<br>SEQ ID NO. 63 | LC CDR1<br>RANQSISRYLN<br>SEQ ID NO. 210<br>LC CDR2<br>AASSLQS<br>SEQ ID NO. 211<br>LC CDR3<br>QQSYSTPSIT<br>SEQ ID NO. 212 |
| Ox5C11 | QVQLVQSGAEVKKPGASVKVSCKTSG YTFT<u>GYYLH</u>WVRQAPGQGLEWMG<u>IIN PSDGGTRYAQKFQ</u>DRVTMTRDMSTST VYMELSSLRPEDTAVYYCAR<u>DLEYIG SGSLSWFDP</u>WGQGTLVTVSS SEQ ID NO. 7 | NFMLTQPRSVSGSPGQSVTISC<u>TGTS SDIGGYSSVS</u>WYQQHPGKAPKLIIY<u>D VTERPS</u>GVPDRFSGSKSGDTATLTIS GLQAEDEADYFC<u>SSYAGVYTYV</u>FGTG TKVTVL SEQ ID NO. 213 |
| Ox5C11 | HC CDR1<br>GYYLH<br>SEQ ID NO. 67<br>HC CDR2<br>IINPSDGGTRYAQKFQD<br>SEQ ID NO. 68<br>HC CDR3<br>DLYIGSGSLSWFDP<br>SEQ ID NO. 69 | LC CDR1<br>TGTSSDIGGYSSVS<br>SEQ ID NO. 214<br>LC CDR2<br>DVTERPS<br>SEQ ID NO. 215<br>LC CDR3<br>SSYAGVYTYV<br>SEQ ID NO. 216 |

I claim:

1. An isolated anti-OX40 antibody, or an antigen-binding fragment thereof, wherein the heavy chain variable domain comprises the amino acid sequence of SEQ ID NO: 24; and comprises a light chain variable domain comprising the amino acid sequence SEQ ID NO: 25.

2. The anti-OX40 antibody, or antigen-binding fragment thereof, of claim 1, wherein the antibody is a human antibody.

3. The anti-OX40 antibody of claim 1, which is an IgG.

4. The anti-OX40 antibody of claim 1, wherein the antibody is an IgG1, IgG2, IgG3 or an IgG4 isotype.

5. The anti-OX40 antibody, or antigen-binding fragment thereof, of claim 1, wherein the antigen-binding fragment is a Fab fragment or an scFv.

6. A pharmaceutical composition comprising the anti-OX40 antibody, or antibody fragment of claim 1, and a pharmaceutically acceptable carrier.

7. An isolated anti-OX40 antibody, comprising:
a heavy chain and a light chain, wherein
(i) the heavy chain comprises: a heavy chain complementarity determining region 1 (CDR1) having the amino acid sequence of SEQ ID NO:118, a heavy chain CDR2 having the amino acid sequence of SEQ ID NO:119, and a heavy chain CDR3 having the amino acid sequence of SEQ ID NO:120; and
(ii) the light chain comprises: a light chain CDR1 having the amino acid sequence of SEQ ID NO:121, a light chain CDR2 having the amino acid sequence of SEQ ID NO:122, and a light chain CDR3 having the amino acid sequence of SEQ ID NO:123.

8. The isolated anti-OX40 antibody of claim 7, wherein the antibody is a human antibody.

* * * * *